(12) United States Patent
Stauss et al.

(10) Patent No.: US 11,643,451 B2
(45) Date of Patent: May 9, 2023

(54) T CELL RECEPTOR

(71) Applicant: UCL Business LTD, London (GB)

(72) Inventors: Hans Stauss, London (GB); Sharyn Thomas, London (GB); Ben Willcox, Birmingham (GB); Fiyaz Mohammed, Birmingham (GB)

(73) Assignee: UCL Business LTD, London (GB)

( * ) Notice: Subject to any disclaimer, the term of this patent is extended or adjusted under 35 U.S.C. 154(b) by 943 days.

(21) Appl. No.: 16/343,252

(22) PCT Filed: Oct. 19, 2017

(86) PCT No.: PCT/GB2017/053167
§ 371 (c)(1),
(2) Date: Apr. 18, 2019

(87) PCT Pub. No.: WO2018/073595
PCT Pub. Date: Apr. 26, 2018

(65) Prior Publication Data
US 2019/0338012 A1    Nov. 7, 2019

(30) Foreign Application Priority Data
Oct. 19, 2016 (GB) .................................. 1617714

(51) Int. Cl.
*C07K 14/725* (2006.01)
*C07K 1/00* (2006.01)
*A61K 38/00* (2006.01)

(52) U.S. Cl.
CPC .......... *C07K 14/7051* (2013.01); *C07K 1/006* (2013.01); *A61K 38/00* (2013.01)

(58) Field of Classification Search
None
See application file for complete search history.

(56) References Cited

U.S. PATENT DOCUMENTS

| | | |
|---|---|---|
| 2008/0292549 A1 | 11/2008 | Jakobsen et al. |
| 2010/0297093 A1 | 11/2010 | Robbins et al. |
| 2012/0027739 A1 | 2/2012 | Jakobsen et al. |
| 2012/0128704 A1 | 5/2012 | Schendel et al. |
| 2014/0341809 A1 | 11/2014 | Pierce et al. |
| 2018/0251513 A1 | 9/2018 | Stauss et al. |
| 2019/0048085 A1 | 2/2019 | Dotti et al. |
| 2019/0336531 A1 | 11/2019 | Stauss et al. |
| 2021/0395331 A1 | 12/2021 | Stauss et al. |

FOREIGN PATENT DOCUMENTS

| | | | |
|---|---|---|---|
| EP | 3015477 A1 | 5/2016 | |
| WO | WO 2005/113595 A2 | 12/2005 | |
| WO | 2006029010 A2 | 3/2006 | |
| WO | 2011/001152 A1 | 1/2011 | |
| WO | 2012013913 A1 | 2/2012 | |
| WO | 2014160030 A2 | 10/2014 | |
| WO | 2014/206304 A1 | 12/2014 | |
| WO | 2016007570 A2 | 1/2016 | |
| WO | 2016170320 A1 | 10/2016 | |
| WO | 2018/073595 A1 | 4/2018 | |
| WO | 2018/073596 A2 | 4/2018 | |
| WO | WO-2021023996 A2 | 2/2021 | |

OTHER PUBLICATIONS

Aggen et al. (Protein Engineering, Design & Selection vol. 24 No. 4 pp. 361-372, 2011). (Year: 2011).*
Kieke et al. (Proc. Natl. Acad. Sci. USA vol. 96, pp. 5651-5656, May 1999). (Year: 1999).*
Shusta et al. (Nature Biotechnology vol. 18 Jul. 2000, 754-759). (Year: 2000).*
Coffin JM, et al., "Retroviruses" Cold Spring Harbor Laboratory Press, 758-763 (1997).
Donnelly M et al., "The 'cleavage' activities of foot-and-mouth disease virus 2A site-directed mutants and naturally occurring '2A-like' sequences," Journal of General Virology, vol. 82:1027-1041 (2001).
Fernandez C S et al., "Ex-vivo alpha-Galactosylceramide activation of NKT cells in humans and macaques," Journal of Immunological Methods, vol. 382:150-159 (2012).
Folch G & Lefranc M P, "The human T cell receptor beta variable (TRBV) genes," Exp Clin Immunogenet, vol. 17:42-54 (2000).
Godfrey D.I. et al., "Going both ways: Immune regulation via CD1d-dependent NKT cells," Journal of Clinical nvestigation, vol. 114(10):1379-1388 (2004).
Henel G et al., "Basic Theory and Clinical Applications of Flow Cytometry," Lab Medicine, vol. 38(7):428-436 (2007).
Henikoff S. et al., "Amino acid substitution matrices from protein blocks," Proc. Natl. Acad. Sci. USA, vol. 89:10915-10919 (1992).
Hodges E et al., "Diagnostic role of tests for T cell receptor (TCR) genes," J Clin Pathol., vol. 56(1):1-11 (2003).
International Preliminary Report on Patentability, PCT/GB2016/051084, dated Jul. 28, 2017, 68 pages.
International Preliminary Report on Patentability, PCT/GB2017/053167, dated Apr. 23, 2019, 11 pages.
International Preliminary Report on Patentability, PCT/GB2017/053168, dated Apr. 23, 2019, 11 pages.

(Continued)

*Primary Examiner* — Zachary S Skelding
(74) *Attorney, Agent, or Firm* — Cooley LLP

(57) ABSTRACT

TCR The present invention relates to an engineered T cell receptor (TCR). In particular, the present invention relates to methods for expression of a TCR when expressed as an exogenous TCR, to methods for selecting a TCR with high cell surface expression when expressed as an exogenous TCR and to methods for identifying residues which contribute to the cell surface expression level of a TCR. The present invention also relates to an engineered TCR which has a high level of cell surface expression when expressed as an exogenous TCR compared to the corresponding germline TCR sequence.

11 Claims, 50 Drawing Sheets

Specification includes a Sequence Listing.

(56) References Cited

OTHER PUBLICATIONS

International Search Report and Written Opinion, PCT/GB2016/051084, dated Jun. 7, 2016, 11 pages.
International Search Report and Written Opinion, PCT/GB2017/053167, dated Mar. 26, 2018, 17 pages.
International Search Report and Written Opinion, PCT/GB2017/053168, dated Apr. 16, 2018, 17 pages.
Jiang Z-M et al., "Development of genetically engineered iNKT cells expressing TCRs specific for the M. tuberculosis 38-kDa antigen", Journal of Translational Medicine, vol. 13 (141): 10 pages (2015).
Koop, B.F. et al., "The human T-cell receptor TCRAC/TCRDC (Calpha/Cdelta) region: Organization, sequence and evolution of 97.6 kb of DNA," Genomics, vol. 19:478-493(1994).
Lefranc M-P et al., "IMGT unique numbering for immunoglobulin and T cell receptor variable domains and Ig superfamily V-like domains," Developmental & Comparative Immunology, vol. 27 (Issue 1):55-77 (2003).
Lewis P. et al., "Human immunodeficiency virus infection of cells arrested in the cell cycle," EMBO J., vol. 11(8):3053-3058 (1992).
MacDonald H R, "NKTcells: In the beginning . . . ," Eur. J. Immunol., vol. 37: S111-115 (2007).
Papworth, C. et al., "Highly Efficient Double-Stranded, Site-Directed Mutagenesis with the Chameleon Kit" Strategies n Molecular Biology, vol. 7: 38-40 (1994).
Reinherz E.L. et al., "The Crystal Structure of a T Cell Receptor in Complex with Peptide and MHC Class II," Science, vol. 286 (Issue 5446): 1913-1921 (1999).
Reiser J-B et al., "Crystal structure of a T cell receptor bound to an allogenic MHC molecule," Nature Immunology, vol. 1: 291-297 (2000).
Richman, S.A. et al., "Structural features of T cell receptor variable regions that enhance domain stability and enable expression as single-chain ValphaVbeta fragments," Molecular Immunology, vol. 46(5):902-916 (2009).
Rowen L et al., "The complete 685-kilobase DNA sequence of the human beta T cell receptor locus," Science, vol. 272(5269):1755-1762 (1996).
Scaviner D. et al., "The Human T Cell Receptor AlphaVariable (TRAV) Genes," Exp Clin Immunogenet, vol. 17:83-96 (2000).
Sethi D K et al., "A highly tilted binding mode by a self-reactive T cell receptor results in altered engagement of peptide and MHC," J Exp Med., vol. 208(1): 91-102 (2011).
Shapiro H M., "Practical Flow Cytometry," John Wiley & Sons (2003).
Smith D J et al., "Genetic engineering of hematopoietic stem cells to generate invariant natural killer T Cells", Proceedings National Academy of Sciences, vol. 112 (5):1523-1528 (2015).
Zhou D et al., "High throughput analysis of TCR-Beta rearrangement and gene expression in single T cells," Laboratory Investigation, vol. 86:314-321 (2006).
U.S. Appl. No. 15/578,440, dated Jul. 21, 2020.
Govers, C. et al. (Feb. 1, 2010) "T cell receptor gene therapy: strategies for optimizing transgenic TCR pairing", Trends Mol Med, 16(2):77-87.
Okamoto, S. et al. (Dec. 1, 2009) "Improved expression and reactivity of transduced tumor-specific TCRs in human lymphocytes by specific silencing of endogenous TCR" AACR Annual Meeting, Apr. 14-18, 2018, Chicago, IL, Cancer Res, 69(23):9003-9011.
Okamoto, S. et al. (Dec. 18, 2012) "A Promising Vector for TCR Gene Therapy: Differential Effect of siRNA, 2A Peptide, and Disulfide Bond on the Introduced TCR Expression", Mol Ther Nucleic Acids, 1(12):e63, doi:10.1038/mtna.2012.52; 11 pages.
Pan, J. and Chuansen, S. (2006) Medical Immunology. Zhejian University Press; pp. 179-180 (Chinese); and English translation, 4 pages.
Robbins, P.F. et al. (May 1, 2008) "Single and dual amino acid substitutions in TCR CDRs can enhance antigen-specific T cell functions" J Immunol, 180(9):6116-6131.
Sommermeyer, D. et al. (Jun. 1, 2010) "Minimal Amino Acid Exchange in Human TCR Constant Regions Fosters Improved Function of TCR Gene-Modified TCells" J Immunol, 184(11):6223-6231.
U.S. Appl. No. 15/568,440, filed Oct. 20, 2017, Hans Stauss.
U.S. Appl. No. 16/343,262, filed Apr. 18, 2019, Hans Stauss.
U.S. Appl. No. 15/568,440, dated Dec. 27, 2019, Z. Skelding.
Declaration of Non-Establishment of International Search Report and Written Opinion, issued in International Patent Application No. PCT/GB2020/051881, dated Dec. 18, 2020, 9 pages.
Uddin, I. et al. (2019) An Economical, Quantitative, and Robust Protocol for High-Throughput T Cell Receptor Sequencing from Tumor or Blood. Methods Mol Biol, 1884:15-42. doi: 10.1007/978-1-4939-8885-3_2.
U.S. Appl. No. 15/568,440, by Stauss: Final Office Action, dated Feb. 24, 2021; 22 pages.
U.S. Appl. No. 15/568,440, by Stauss: Non-Final Office Action, dated Jul. 21, 2020; 17 pages.
U.S. Appl. No. 15/568,440, by Stauss: Restriction Requirement, dated Dec. 27, 2019; 8 pages.

\* cited by examiner

|  | Number of TCRs sequenced in the endogenous: | |
|---|---|---|
|  | Strong TCR Population | Weak TCR Population |
| Alpha chains | 294 | 286 |
| Beta chains | 151 | 153 |
| TRAV 38.1 | 20 | 2 |
| TRAV 38.2 | 48 | 11 |
| TRAV 9.2 | 13 | 3 |
| TRBV 5.1 | 42 | 21 |
| TRBV 7.8 | 7 | 0 |
| TRAV 13.2 | 6 | 21 |
| TRAV 23 | 3 | 10 |
| TRBV 7.3 | 2 | 8 |
| TRBV 7.9 | 1 | 11 |

Strong variable segments: TRAV 38.1, TRAV 38.2, TRAV 9.2, TRBV 5.1, TRBV 7.8

Weak variable segments: TRAV 13.2, TRAV 23, TRBV 7.3, TRBV 7.9

FIG. 3

|  | Jurkat cells | | |
|---|---|---|---|
| TCR | % | Myc MFI | V5 MFI |
| Strong TCR | 88 | 2840 | 1341 |
| Weak TCR | 61 | 1077 | 377 |
| Strong TCR / Weak Res | 0.4 | 62 | 138 |
| Weak TCR / Strong Res | 90 | 8582 | 1617 |
| T5α | 73 | 1529 | 479 |
| Q8α | 68 | 1699 | 527 |
| V19α | 80 | 3587 | 791 |
| T20α | 79 | 2340 | 562 |
| T24α | 86 | 2937 | 661 |
| L39α | 15 | 135 | 170 |
| M50α | 61 | 1159 | 378 |
| R55α | 1.5 | 89 | 141 |
| A66α | 60 | 826 | 366 |
| S86α | 67 | 1854 | 465 |
| L96α | 75 | 3738 | 770 |
| R9β, Y10β | 69 | 3951 | 599 |
| Q43β | 15 | 117 | 185 |
| V19α, R9β, Y10β | 83 | 6717 | 1064 |

FIG. 10 (Continued)

| | WT1 TCR Jurkat cells | | |
|---|---|---|---|
| TCR | % | Myc MFI | V5 MFI |
| Strong TCR | 41 | 217 | 224 |
| Weak TCR | 12 | 100 | 163 |
| Strong TCR / Weak Res | 1 | 62 | 149 |
| Weak TCR / Strong Res | 55 | 704 | 254 |
| T5α | 14 | 91 | 159 |
| Q8α | 14 | 96 | 163 |
| V19α | 19 | 121 | 164 |
| T20α | 18 | 109 | 167 |
| T24α | 19 | 114 | 168 |
| L39α | 1.8 | 82 | 145 |
| M50α | 17 | 114 | 164 |
| R55α | 1 | 64 | 141 |
| A66α | 12 | 96 | 154 |
| S86α | 13 | 101 | 156 |
| L96α | 29 | 162 | 180 |
| R9β, Y10β | 23 | 219 | 164 |
| Q43β | 2 | 65 | 149 |
| V19α, R9β, Y10β | 32 | 344 | 184 |

FIG. 11 (Continued)

CD19 gated

| MFI | Alpha mRNA | Beta mRNA |
|---|---|---|
| Strong TCR | 9847 | 1675 |
| Weak TCR | 8709 | 1045 |
| Strong TCR / Weak res | 9035 | 1480 |
| Weak TCR / Strong res | 9260 | 1487 |

FIG. 17 (Continued)

|     | Ala | Arg | Asn | Asp | Cys | Gln | Glu | Gly | His | Ile | Leu | Lys | Met | Phe | Pro | Ser | Thr | Trp | Tyr | Val |
| --- | --- | --- | --- | --- | --- | --- | --- | --- | --- | --- | --- | --- | --- | --- | --- | --- | --- | --- | --- | --- |
| Ala | 4   |     |     |     |     |     |     |     |     |     |     |     |     |     |     |     |     |     |     |     |
| Arg | -1  | 5   |     |     |     |     |     |     |     |     |     |     |     |     |     |     |     |     |     |     |
| Asn | -2  | 0   | 6   |     |     |     |     |     |     |     |     |     |     |     |     |     |     |     |     |     |
| Asp | -2  | -2  | 1   | 6   |     |     |     |     |     |     |     |     |     |     |     |     |     |     |     |     |
| Cys | 0   | -3  | -3  | -3  | 9   |     |     |     |     |     |     |     |     |     |     |     |     |     |     |     |
| Gln | -1  | 1   | 0   | 0   | -3  | 5   |     |     |     |     |     |     |     |     |     |     |     |     |     |     |
| Glu | -1  | 0   | 0   | 2   | -4  | 2   | 5   |     |     |     |     |     |     |     |     |     |     |     |     |     |
| Gly | 0   | -2  | 0   | -1  | -3  | -2  | -2  | 6   |     |     |     |     |     |     |     |     |     |     |     |     |
| His | -2  | 0   | 1   | -1  | -3  | 0   | 0   | -2  | 8   |     |     |     |     |     |     |     |     |     |     |     |
| Ile | -1  | -3  | -3  | -3  | -1  | -3  | -3  | -4  | -3  | 4   |     |     |     |     |     |     |     |     |     |     |
| Leu | -1  | -2  | -3  | -4  | -1  | -2  | -3  | -4  | -3  | 2   | 4   |     |     |     |     |     |     |     |     |     |
| Lys | -1  | 2   | 0   | -1  | -3  | 1   | 1   | -2  | -1  | -3  | -2  | 5   |     |     |     |     |     |     |     |     |
| Met | -1  | -1  | -2  | -3  | -1  | 0   | -2  | -3  | -2  | 1   | 2   | -1  | 5   |     |     |     |     |     |     |     |
| Phe | -2  | -3  | -3  | -3  | -2  | -3  | -3  | -3  | -1  | 0   | 0   | -3  | 0   | 6   |     |     |     |     |     |     |
| Pro | -1  | -2  | -2  | -1  | -3  | -1  | -1  | -2  | -2  | -3  | -3  | -1  | -2  | -4  | 7   |     |     |     |     |     |
| Ser | 1   | -1  | 1   | 0   | -1  | 0   | 0   | 0   | -1  | -2  | -2  | 0   | -1  | -2  | -1  | 4   |     |     |     |     |
| Thr | 0   | -1  | 0   | -1  | -1  | -1  | -1  | -2  | -2  | -1  | -1  | -1  | -1  | -2  | -1  | 1   | 5   |     |     |     |
| Trp | -3  | -3  | -4  | -4  | -2  | -2  | -3  | -2  | -2  | -3  | -2  | -3  | -1  | 1   | -4  | -3  | -2  | 11  |     |     |
| Tyr | -2  | -2  | -2  | -3  | -2  | -1  | -2  | -3  | 2   | -1  | -1  | -2  | -1  | 3   | -3  | -2  | -2  | 2   | 7   |     |
| Val | 0   | -3  | -3  | -3  | -1  | -2  | -2  | -3  | -3  | 3   | 1   | -2  | 1   | -1  | -2  | -2  | 0   | -3  | -1  | 4   |

```
                        SEQUENCE LISTING

<160> NUMBER OF SEQ ID NOS: 2

<210> SEQ ID NO 1
<211> LENGTH: 96
<212> TYPE: PRT
<213> ORGANISM: Artificial Sequence
<220> FEATURE:
<223> OTHER INFORMATION: T cell receptor (TCR) sequence

<400> SEQUENCE: 1

Ala Gln Thr Val Thr Gln Ser Gln Pro Glu Met Ser Val Gln Glu Ala
1               5                   10                  15

Glu Thr Val Thr Leu Ser Cys Thr Tyr Asp Thr Ser Glu Asn Asn Tyr
            20                  25                  30

Tyr Leu Phe Trp Tyr Lys Gln Pro Pro Ser Arg Gln Met Ile Leu Val
        35                  40                  45

Ile Arg Gln Glu Ala Tyr Lys Gln Gln Asn Ala Thr Glu Asn Arg Phe
    50                  55                  60

Ser Val Asn Phe Gln Lys Ala Ala Lys Ser Phe Ser Leu Lys Ile Ser
65                  70                  75                  80

Asp Ser Gln Leu Gly Asp Thr Ala Met Tyr Phe Cys Ala Phe Met Lys
                85                  90                  95

<210> SEQ ID NO 2
<211> LENGTH: 96
<212> TYPE: PRT
<213> ORGANISM: Artificial Sequence
<220> FEATURE:
<223> OTHER INFORMATION: T cell receptor (TCR) sequence

<400> SEQUENCE: 2

Gly Ala Gly Val Ser Gln Ser Pro Arg Tyr Lys Val Ala Lys Arg Gly
1               5                   10                  15

Gln Asp Val Ala Leu Arg Cys Asp Pro Ile Ser Gly His Val Ser Leu
            20                  25                  30

Phe Trp Tyr Gln Gln Ala Leu Gly Gln Gly Pro Glu Phe Leu Thr Tyr
        35                  40                  45

Phe Gln Asn Glu Ala Gln Leu Asp Lys Ser Gly Leu Pro Ser Asp Arg
    50                  55                  60

Phe Phe Ala Glu Arg Pro Glu Gly Ser Val Ser Thr Leu Lys Ile Gln
65                  70                  75                  80

Arg Thr Gln Gln Glu Asp Ser Ala Val Tyr Leu Cys Ala Ser Ser Leu
                85                  90                  95
```

T CELL RECEPTOR

RELATED APPLICATIONS

This application is a 35 U.S.C. § 371 national stage filing of PCT Application No. PCT/GB2017/053167, filed on Oct. 19, 2017, which claims the benefit of and the priority of United Kingdom Patent Application No. 1617714.9, which was on filed Oct. 19, 2016. The entire content of each of the above-referenced patent applications is hereby incorporated by reference in its entirety.

REFERENCE TO SEQUENCE LISTING

The instant application contains a Sequence Listing which has been submitted electronically in ASCII format and is hereby incorporated by reference in its entirety. Said ASCII copy, created Apr. 17, 2019, is named "DYN-004US_Sequence-Listing.txt" and is 2191 Kilobytes in size.

FIELD OF THE INVENTION

The present invention relates to a T cell receptor (TCR). In particular, the present invention relates to methods for increasing the dimerization of TCRs and/or methods for reducing mispairing of TCRs and/or methods for increasing cell surface expression of a TCR when it is expressed as an exogenous TCR, to methods for selecting such TCR and to methods for identifying residues which contribute to the dimerization of TCRs and/or for reducing mispairing of TCRs and/or increasing cell surface expression level of a TCR. The present invention also relates to an engineered TCR which has a high level of cell surface expression when expressed as an exogenous TCR compared to the corresponding germline TCR sequence.

BACKGROUND TO THE INVENTION

T cell receptor (TCR) gene therapy is the transfer of antigen-specific TCR chains into recipient T-cells, thus redirecting the specificity of T-lymphocytes to target antigens of interest.

Introduced TCRs differ greatly in their ability to be expressed on the cell surface. Introduced, strongly expressed TCRs are co-expressed with the endogenous TCR or can even out-compete the endogenous TCR for cell surface expression. Introduced, weakly expressed TCRs are absent from the cell surface when co-expressed with an endogenous strong TCR (FIG. 1).

High levels of expression of an antigen specific TCR on the T cell surface results in a greater avidity of the T cell, which is beneficial for the efficacy of therapeutic TCR therapy.

There is thus a need for methods and approaches which increase the cell surface expression of weakly expressed TCR.

SUMMARY OF ASPECTS OF THE INVENTION

The present inventors have determined that the amino acid residues present at a number of key amino acid positions within the TCR framework regions enhance TCR cell surface expression. The present inventors have further determined that the amino acid residues present at these key amino acid positions within the TCR framework region may enhance the dimerization of TCRs and/or reduce mispairing of TCRs, for example when they are expressed as an exogenous TCR.

It particular, the inventors have determined that the amino acid residues specified for the given position listed in Group (I), or amino acid residues with similar biochemical properties, enhance dimerization of TCRs and/or reduce mispairing of TCRs and/or enhance TCR cell surface expression. In particular, the amino acid residues present at a number of key amino acid positions within the TCR framework regions enhance TCR cell surface expression.

The amino acid residues and relevant positions of Group (I) are L96 of the α chain; R9 of the β chain; Y10 of the β chain; T24 of the α chain; V19 of the α chain; T20 of the α chain; M50 of the α chain; T5 of the α chain; Q8 of the α chain; S86 of the α chain; F39 of the α chain; D55 of the α chain; R43 of the β chain; A66 of the α chain; V19 of the β chain; L21 of the β chain; L103 of the β chain; T3 of the α chain; S7 of the α chain; P9 of the α chain; M11 of the α chain; A16 of the α chain; T18 of the α chain; L21 of the α chain; S22 of the α chain; D26 of the α chain; F40 of the α chain; S47 of the α chain; R48 of the α chain; Q49 of the α chain; I51 of the α chain; L52 of the α chain; V53 of the α chain; T67 of the α chain; E68 of the α chain; N74 of the α chain; F76 of the α chain; N79 of the α chain; Q81 of the α chain; A83 of the α chain; K90 of the α chain; S92 of the α chain; D93 of the α chain; and M101 of the α chain.

The identified residues affect structural features of the TCR. Hence, it is expected that conserved residues with similar properties will have similar structural effects. In particular, the residues found in homologous proteins with conserved function as defined by the Blosum62 score are expected to have similar effects on TCR strength. For example, conserved amino acids and respective amino acids with a Blosum62 score greater than 0 are therefore also expected to enhance TCR expression.

It has been demonstrated that substitution with these key amino acid residues in a weakly expressed TCR results in a greatly improved expression. It has also been demonstrated that single amino acid substitutions of individual key residues to replace 'weak' residues with 'strong' amino acid residues as defined by the present invention, as well as a range of amino-acid substitution combinations, increased TCR expression.

Advantageously the technology of the present disclosure is effective even where the constant domains of the TCR are fully human.

The changing of an amino acid can be achieved economically, quickly and efficiently by mutagenesis, for example PCR mutagenesis. This method of increasing TCR cell surface expression does not interfere with peptide/MHC recognition by the TCR and does not affect the TCR folding or structure. Thus TCR expression is increased with a minimal impact on TCR structure.

Accordingly, the present invention provides a method which comprises the steps of:
 (i) providing a TCR α chain and/or β chain sequence;
 (ii) determining an amino acid residue of the TCR α chain and/or β chain at one or more positions selected from: 96 of the α chain; 9 of the β chain; 10 of the β chain; 24 of the α chain; 19 of the α chain; 20 of the α chain; 50 of the α chain; 5 of the α chain; 8 of the α chain; 86 of the α chain; 39 of the α chain; 55 of the α chain; 43 of the β chain; 66 of the α chain; 19 of the β chain; 21 of the β chain; 103 of the β chain; 3 of the α chain; 7 of the α chain; 9 of the α chain; 11 of the α chain; 16 of the α chain; 18 of the α chain; 21 of the α chain; 22 of the α chain; 26 of the α chain; 40 of the α chain; 47 of the α chain; 48 of the α chain; 49 of the α chain; 51 of the α chain; 52 of the α chain; 53 of the α chain; 67 of the α chain; 68 of the α chain; 74 of the α chain; 76 of the α chain; 79 of the α chain; 81 of the α chain; 83 of the α chain; 90 of the α chain; 92 of the α chain; 93 of the α chain; and 101 of the α chain; and (iii) altering the amino acid residue at one or more of the positions listed in step (ii) to an amino acid residue selected from:

an aliphatic, non-polar amino acid or a methionine at position 96 of the α chain;
an aliphatic, polar charged amino acid or a glutamine at position 9 of the β chain;
an aromatic amino acid at position 10 of the β chain;
an aliphatic, polar uncharged amino acid at position 24 of the α chain;
an aliphatic, non-polar amino acid or a methionine at position 19 of the α chain;
an aliphatic, polar uncharged amino acid at position 20 of the α chain;
an aliphatic, polar uncharged amino acid or a isoleucine, leucine or valine at position 50 of the α chain;
an aliphatic, polar uncharged amino acid at position 5 of the α chain;
an aliphatic, polar uncharged amino acid, a glutamic acid, lysine or arginine at position 8 of the α chain;
an aliphatic, polar uncharged amino acid or alanine at position 86 of the α chain;
an aromatic amino acid at position 39 of the α chain;
an aliphatic, polar charged amino acid or asparagine at position 55 of the α chain;
an aliphatic, polar charged amino acid or a glutamine at position 43 of the β chain;
an aliphatic, non-polar amino acid or a serine at position 66 of the α chain;
an aliphatic, non-polar amino acid or a methionine at position 19 of the β chain;
an aliphatic, non-polar amino acid or a methionine at position 21 of the β chain;
an aliphatic, non-polar amino acid or a methionine at position 103 of the β chain;
an aliphatic, polar uncharged amino acid at position 3 of the α chain;
an aliphatic, polar uncharged amino acid or alanine at position 7 of the α chain;
an aliphatic, non-polar amino acid at position 9 of the α chain;
an aliphatic, non-polar amino acid or a isoleucine, leucine or valine at position 11 of the α chain;
an aliphatic, non-polar amino acid or a serine at position 16 of the α chain;
an aliphatic, polar uncharged amino acid at position 18 of the α chain;
an aliphatic, non-polar amino acid or a methionine at position 21 of the α chain;
an aliphatic, polar uncharged amino acid or alanine at position 22 of the α chain;
an aliphatic, polar charged amino acid or asparagine at position 26 of the α chain;
an aromatic amino acid at position 40 of the α chain;
an aliphatic, polar uncharged amino acid or alanine at position 47 of the α chain;
an aliphatic, polar charged amino acid or a glutamine at position 48 of the α chain;
an aliphatic, polar uncharged amino acid, glutamic acid, lysine or arginine at position 49 of the α chain;
an aliphatic, non-polar amino acid or a methionine at position 51 of the α chain;
an aliphatic, non-polar amino acid or a methionine at position 52 of the α chain;
an aliphatic, non-polar amino acid or a methionine at position 53 of the α chain;
an aliphatic, polar uncharged amino acid at position 67 of the α chain;
an aliphatic, polar charged amino acid or a glutamine at position 68 of the α chain;
an aliphatic, polar uncharged amino acid or an aspartic acid or histidine at position 74 of the α chain;
an aromatic amino acid at position 76 of the α chain;
an aliphatic, polar uncharged amino acid or an aspartic acid or histidine at position 79 of the α chain;
an aliphatic, polar uncharged amino acid, glutamic acid, lysine or arginine at position 81 of the α chain;
an aliphatic, non-polar amino acid or a serine at position 83 of the α chain;
an aliphatic, polar charged amino acid or a glutamine at position 90 of the α chain;
an aliphatic, polar uncharged amino acid or alanine at position 92 of the α chain;
an aliphatic, polar charged amino acid or asparagine at position 93 of the α chain;
an aliphatic, non-polar amino acid or a isoleucine, leucine or valine at position 101 of the α chain;

with the proviso that when only one amino acid is altered in step (iii) the altered amino acid generated does not consist of an amino acid residue specified for the given position selected from group (I):

(I) L96 of the α chain; R9 of the β chain; Y10 of the β chain; T24 of the α chain; V19 of the α chain; T20 of the α chain; M50 of the α chain; T5 of the α chain; Q8 of the α chain; S86 of the α chain; F39 of the α chain; D55 of the α chain; R43 of the β chain; A66 of the α chain; V19 of the β chain; L21 of the β chain; L103 of the β chain; T3 of the α chain; S7 of the α chain; P9 of the α chain; M11 of the α chain; A16 of the α chain; T18 of the α chain; L21 of the α chain; S22 of the α chain; D26 of the α chain; F40 of the α chain; S47 of the α chain; R48 of the α chain; Q49 of the α chain; I51 of the α chain; L52 of the α chain; V53 of the α chain; T67 of the α chain; E68 of the α chain; N74 of the α chain; F76 of the α chain; N79 of the α chain; Q81 of the α chain; A83 of the α chain; K90 of the α chain; S92 of the α chain; D93 of the α chain; and M101 of the α chain; and when two or more amino acid residues are altered in step (iii) at least one of the altered amino acid residues generated is not an amino acid residue specified for the given position selected from group (I).

In one embodiment, the method is a method for increasing the cell surface expression of a T cell receptor (TCR). In one embodiment, the method is a method for increasing dimerization of TCRs, in particular dimerization of TCR α and β chains. In one embodiment, the method is a method for reducing mispairing of TCRs, in particular dimerization of TCR α and β chains.

DESCRIPTION OF THE FIGURES

FIG. 19—BLOSUM62 Score Matrix.

FIG. 29—Analysis of the three TCRs with appropriate modifications in human Jurkat cells that do not express an endogenous TCR. Shown is level of TCR alpha chain expression (V-5 staining; y-axis) and TCR beta chain expression (myc staining; x-axis) of gated CD19-high cells.

FIG. 31—Analysis of the three TCRs with appropriate modifications in human Jurkat cells that do express an endogenous TCR. Shown is level of TCR alpha chain expression (V-5 staining; y-axis) and TCR beta chain expression (myc staining; x-axis) of gated CD19-high cells.

DETAILED DESCRIPTION

T Cell Receptor

During antigen processing, antigens are degraded inside cells and then carried to the cell surface by major histocompatability complex (MHC) molecules. T cells are able to recognise this peptide:MHC complex at the surface of the antigen presenting cell. There are two different classes of MHC molecules, MHC I and MHC II, that deliver peptides from different cellular compartments to the cell surface.

The T cell receptor or TCR is the molecule found on the surface of T cells that is responsible for recognizing antigens bound to MHC molecules. The TCR heterodimer consists of an α and β chain in 95% of T cells, whereas 5% of T cells have TCRs consisting of γ and δ chains.

Engagement of the TCR with antigen and MHC results in activation of its T lymphocyte through a series of biochemical events mediated by associated enzymes, co-receptors, and specialized accessory molecules.

Figure 1:
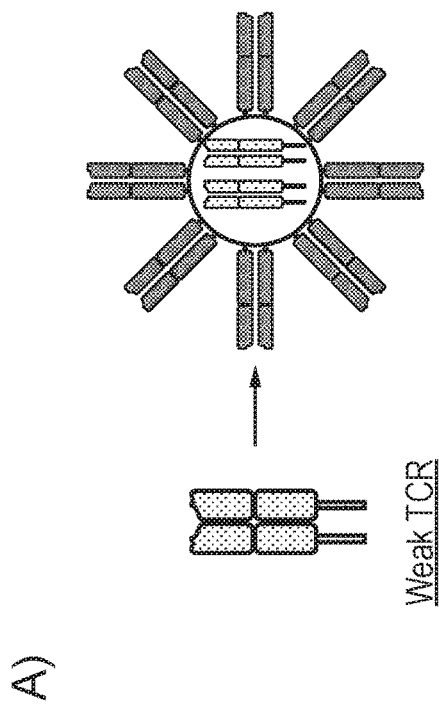
FIG. 1—A) Depiction of a weak exogenous TCR and a strong exogenous TCR in a cell which also expresses an endogenous TCR. B) Schematic Drawing of the TCRα and TCRβ chains—SP: Signal peptide; FR: Framework Region; CDR: Complementarity Determining Region; IG: Immunoglobulin like domain of the C-region; CP: Connecting Peptide; TM: Transmembrane domain; IC: Intracellular domain.
Figure 1:
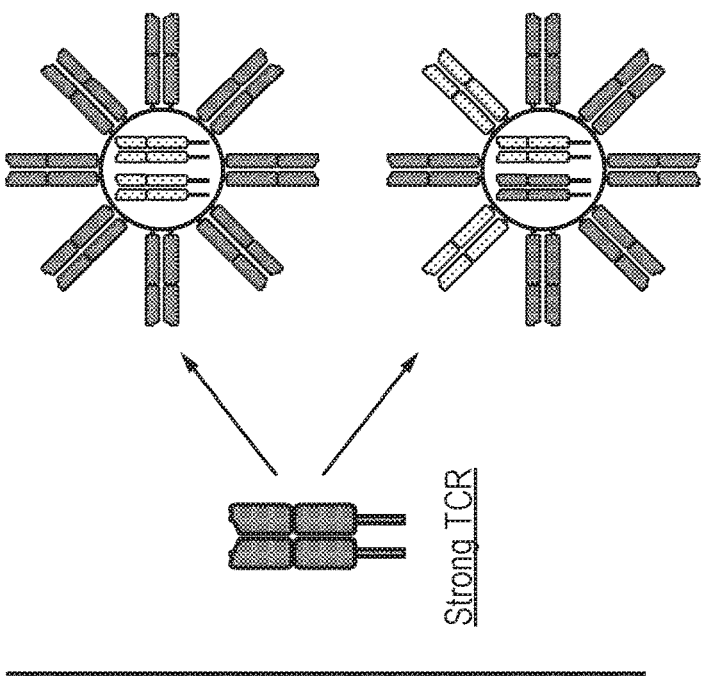

Each chain of the TCR is a member of the immunoglobulin superfamily and possesses one N-terminal immunoglobulin (Ig)-variable (V) domain, one Ig-constant (C) domain, a transmembrane/cell membrane-spanning region, and a short cytoplasmic tail at the C-terminal end (FIG. 1B).

The variable domain of both the TCR α-chain and β-chain have three hypervariable or complementarity determining regions (CDRs). CDR3 is the main CDR responsible for recognizing processed antigen, although CDR1 of the alpha chain has also been shown to interact with the N-terminal part of the antigenic peptide, whereas CDR1 of the beta chain interacts with the C-terminal part of the peptide. CDR2 is thought to recognize the MHC molecule. Framework regions (FRs) are positioned between the CDRs. These regions provide the structure of the TCR variable region.

The repertoire of TCR variable regions is generated by combinatorial joining of variable (V), joining (J) and diversity (D) genes; and by N region diversification (nucleotides inserted by the enzyme deoxynucleotidyl-transferase). α and γ chains are formed from recombination events between the V and J segments. β and δ chains are formed from recombination events involving the V, D and J segments.

The human TCRα locus, which also includes the TCRδ locus, is located on chromosome 14 (14q11.2). The TCRβ locus is located on chromosome 7 (7q34). The variable region of the TCRα chain is formed by recombination between one of 46 different Vα (variable) segments and one of 58 Jα (joining) segments (Koop et al.; 1994; Genomics; 19: 478-493). The variable region of a TCRβ chain is formed from recombination between 54 Vβ, 14 Jβ and 2 Dβ (diversity) segments (Rowen et al.; 1996; Science; 272: 1755-1762).

The V and J (and D as appropriate) gene segments for each TCR chain locus have been identified and the germline sequence of each gene is known and annotated (for example see Scaviner & Lefranc; 2000; Exp Clin Immunogenet; 17:83-96 and Folch & Lefranc; 2000; Exp Clin Immunogenet; 17:42-54).

FR1, CDR1, FR2, CDR2, FR3 and CDR3 of the α chain are encoded by the Vα gene. FR4 is encoded by the Jα gene (FIG. 1B).

FR1, CDR1, FR2, CDR2 and FR3 of the β chain are encoded by the Vβ gene. CDR3 is encoded by the Dβ gene and FR4 is encoded by the Jβ gene (FIG. 1B).

As the germline sequence of each variable gene is known in the art (see Scaviner & Lefranc; as above and Folch & Lefranc; as above) the Vα and/or Vβ of a particular TCR can be sequenced and the germline V segment which is utilised in the TCR can be identified (see, for example, Hodges et al.; 2003; J Clin Pathol; 56:1-11, Zhou et al.; 2006; Laboratory Investigation; 86; 314-321)

The constant domain of the TCR domain consists of short connecting sequences in which a cysteine residue forms a disulfide bond, making a link between the two chains. The TCR of the present invention may have an additional cysteine residue in each of the α and β chains such that the TCR comprises two disulphide bonds in the constant domains (see below).

In one embodiment the constant domains employed in the TCR are human sequences.

In one embodiment the constant domains employed in the TCR are murine sequences.

The structure allows the TCR to associate with other molecules like CD3 which possess three distinct chains (γ, δ, and ε) in mammals and the ζ-chain. These accessory molecules have negatively charged transmembrane regions and are vital to propagating the signal from the TCR into the cell. The CD3- and ζ-chains, together with the TCR, form what is known as the T cell receptor complex.

The signal from the T cell complex is enhanced by simultaneous binding of the MHC molecules by a specific co-receptor. On helper T cells, this co-receptor is CD4 (specific for class II MHC); whereas on cytotoxic T cells, this co-receptor is CD8 (specific for class I MHC). The co-receptor not only ensures the specificity of the TCR for an antigen, but also allows prolonged engagement between the antigen presenting cell and the T cell and recruits essential molecules (e.g., LCK) inside the cell involved in the signalling of the activated T lymphocyte.

The term "T-cell receptor" is thus used in the conventional sense to mean a molecule capable of recognising a peptide when presented by an MHC molecule. The molecule may be a heterodimer of two chains α and β (or optionally γ and δ) or it may be a single chain TCR construct.

The present invention also provides the α chain or β chain from such a T cell receptor.

The present TCR may be a hybrid TCR comprising sequences derived from more than one species. For example, it has surprisingly been found that murine TCRs have been found to be more efficiently expressed in human T cells than human TCRs. The TCR may therefore comprise human variable regions and murine constant regions. A disadvantage of this approach is that the murine constant sequences may trigger an immune response, leading to rejection of the transferred T cells. However, the conditioning regimens used to prepare patients for adoptive T-cell therapy may result in sufficient immunosuppression to allow the engraftment of T cells expressing murine sequences.

The present engineered TCR comprises one or more amino acid residue as defined herein which is not encoded by the germline Vα or Vβ gene. In other words, the engineered TCR comprises an α chain and/or β chain which comprises an altered amino acid residue at one or more of the positions described herein, compared to the corresponding α chain and/or β chain as encoded by the unaltered germline Vα or Vβ gene.

The amino acid residues identified herein are numbered according to the International ImMunoGeneTics information system' (IMGT). This system is well known in the art (Lefrance et al.; 2003; Dev Comp Immunol; 27: 55-77) and is based on the high conservation of the structure of the variable region. The numbering takes into account and combines the definition of the FR and CDRs, structural data from X-ray diffraction studies and the characterization of the hypervariable loops.

The delimitations of the FR and CDR regions are defined within the IGMT numbering system. The FR1 region comprises positions 1-26 (25-26 amino acids, depending on the V-GENE group or subgroup) with 1st-CYS at position 23. The FR2 region comprises positions 39-55 (16-17 amino acids) with a conserved TRP at position 41. The FR3 region comprises positions 66-104 (36-39 amino acids, depending on the VGENE group or subgroup) with a conserved hydrophobic amino acid at position 89 and the 2nd-CYS at position 104. Residue 1 of the IGMT numbering system is the first residue in FR1. Residue 104 of the IGMT numbering system is the last residue in FR3.

As such, the numbering system used herein refers to the position of the amino acid within the entire α chain or the entire β chain, as appropriate.

The IGMT numbering therefore allows a standardized description of amino acid positions within TCR variable regions and comparisons with the germline encoded sequences to be performed.

Methods suitable for generating an engineered TCR according to the present invention are known in the art.

For example mutagenesis may be performed to alter specific nucleotides in a nucleic acid sequence encoding the TCR. Such mutagenesis will alter the amino acid sequence of the TCR so that it comprises one or more of the amino acid residues as described herein.

An example of a mutagenesis method is the Quikchange method (Papworth et al.; 1996; Strategies; 9(3); 3-4). This method involves the use of a pair of complementary mutagenic primers to amplify a template nucleic acid sequence in a thermocycling reaction using a high-fidelity non-strand-displacing DNA polymerase, such as pfu polymerase.

The present inventors have determined that the presence of particular amino acid residues in specific positions of the TCR framework regions alters the cell surface expression of the TCR.

As used herein, cell surface expression is synonymous with expression strength. As such, 'strong' or 'high' expression is equivalent to high levels of cell surface expression of the TCR. 'Weak' or 'low' expression is equivalent to low levels of cell surface expression of the TCR.

Increasing the cell surface expression of a TCR means that a TCR comprising one or more amino acid residues as described herein has a higher level of cell surface expression relative to an equivalent TCR comprising the amino acid sequence encoded by the germline sequence. An equivalent TCR comprising the amino acid sequence encoded by the germline sequence refers to a TCR which has not been altered to comprise a non-germline amino acid residue at a given position as described herein—i.e. the unaltered TCR has the wild-type amino acid residue at the specific position.

In one embodiment the present engineered TCR may have a cell surface expression which is at least 1.5-, 2-, 2.5-, 3-, 4-, 5-, 6-, 7-, 8-, 9-, or 10-fold greater than the corresponding TCR comprising the unmodified germline TCR sequence.

Cell surface expression of a TCR may be determined by methods which are known in the art. For example, the cell surface expression of a TCR may be determined using conventional flow cytometry methods known in the art (see, for example, Shapiro; Practical Flow Cytometry; John 2005; Science).

For example, the cell surface expression of a TCR may be expressed as the mean fluorescent intensity (MFI) of TCR expression in a population of cells (see Shapiro; as above). In one embodiment the MFI of a population of cells expressing the present engineered TCR may be at least 1.5-, 2-, 2.5-, 3-, 4-, 5-, 6-, 7-, 8-, 9-, or 10-fold greater than the MFI of an corresponding population of cells expressing the corresponding TCR comprising the unmodified germline TCR sequence.

The cell surface expression of a TCR may be expressed as the percentage of cells within a population which express the TCR at the cell surface. Such a percentage may be determined using conventional flow cytometry methods as is well known in the art (see, for example, Shapiro; as above and Henel et al.; 2007; Lab Medicine; 38; 7; 428-436).

In one embodiment, the present engineered TCR may be expressed by at least 2, at least 5, at least 10, at least 15, at least 20, at least 25, at least 30, at least 40, at least 50, at least 60 or at least 70% more cells in a population compared to the corresponding TCR comprising the unmodified germline TCR sequence.

In one embodiment, the cell surface expression of the engineered TCR is increased compared to the corresponding TCR comprising the unmodified germline TCR sequence but the relative level of the mRNA encoding the engineered TCR or the unmodified germline TCR are essentially the same. As used herein, "essentially the same" may mean that mRNA levels differ by, for example, less than 1.5 fold. Relative mRNA levels may be determined using methods which are known in the art; for example RT-qPCR, northern blotting and flow cytometry RNA assays (for example as demonstrated in FIG. 17).

The methods and TCRs of the present invention may enhance dimerization of the TCR α chain and β chain. In particular, the methods and TCRs of the present invention may enhance the dimerization of the present α chain and β chain when they are expressed recombinantly, e.g., as an exogenous TCR in a cell (e.g. a cell as described herein).

The methods and TCRs of the present invention may reduce mispairing between the TCR α chain and/or β chain of the present invention. In particular, the methods and TCRs of the present invention may reduce mispairing between the present TCR α chain and/or β chain and an endogenous α chain and/or β chain of a cell.

The methods and TCRs of the present invention may enhance the dimerization of the TCR α chain and β chain and reduce mispairing between the TCR α chain and/or β chain of the present invention.

Without wishing to be bound by theory, the present inventors consider that the enhanced dimerization and/or reduced mispairing described herein may e.g. contribute to the increased cell surface expression provided by the present invention. Such effects are similar in character to those described for other technologies, such as the introduction of an engineered second disulphide bond into the constant region of an exogenous TCR. Accordingly, the methods and TCRs of the present invention provide further methods for enhancing the dimerization and/or reducing the mispairing of a TCR α chain and β chain when they are expressed recombinantly, e.g., as an exogenous TCR in a cell.

Suitably the present engineered TCR comprises one or more of following amino acid residues selected from Group (A):

Group (A): an aliphatic, non-polar amino acid or a methionine at position 96 of the α chain; an aliphatic, polar charged amino acid or a glutamine at position 9 of the β chain; an aromatic amino acid at position 10 of the β chain; an aliphatic, polar uncharged amino acid at position 24 of the α chain; an aliphatic, non-polar amino acid or a methionine at position 19 of the α chain; an aliphatic, polar uncharged amino acid at position 20 of the α chain; an aliphatic, polar uncharged amino acid or a isoleucine, leucine or valine at position 50 of the α chain; an aliphatic, polar uncharged amino acid at position 5 of the α chain; an aliphatic, polar uncharged amino acid, a glutamic acid, lysine or arginine at position 8 of the α chain; an aliphatic, polar uncharged amino acid or alanine at position 86 of the α chain; an aromatic amino acid at position 39 of the α chain; an aliphatic, polar charged amino acid or asparagine at position 55 of the α chain; an aliphatic, polar charged amino acid or a glutamine at position 43 of the β chain; an aliphatic, non-polar amino acid or a serine at position 66 of the α chain; an aliphatic, non-polar amino acid or a methionine at position 19 of the β chain; an aliphatic, non-polar amino acid or a methionine at position 21 of the β chain; an aliphatic, non-polar amino acid or a methionine at position 103 of the β chain; an aliphatic, polar uncharged amino acid at position 3 of the α chain; an aliphatic, polar uncharged amino acid or alanine at position 7 of the α chain; an aliphatic, non-polar amino acid at position 9 of the α chain; an aliphatic, polar uncharged amino acid or a isoleucine, leucine or valine at position 11 of the α chain; an aliphatic, non-polar amino acid or a serine at position 16 of the α chain; an aliphatic, polar uncharged amino acid at position 18 of the α chain; an aliphatic, non-polar amino acid or a methionine at position 21 of the α chain; an aliphatic, polar uncharged amino acid or alanine at position 22 of the α chain; an aliphatic, polar charged amino acid or asparagine at position 26 of the α chain; an aromatic amino acid at position 40 of the α chain; an aliphatic, polar uncharged amino acid or alanine at position 47 of the α chain; an aliphatic, polar charged amino acid or a glutamine at position 48 of the α chain; an aliphatic, polar uncharged amino acid, glutamic acid, lysine or arginine at position 49 of the α chain; an aliphatic, non-polar amino acid or a methionine at position 51 of the α chain; an aliphatic, non-polar amino acid or a methionine at position 52 of the α chain; an aliphatic, non-polar amino acid or a methionine at position 53 of the α chain; an aliphatic, polar uncharged amino acid at position 67 of the α chain; an aliphatic, polar charged amino acid or a glutamine at position 68 of the α chain; an aliphatic, polar uncharged amino acid or an aspartic acid or histidine at position 74 of the α chain; an aromatic amino acid at position 76 of the α chain; an aliphatic, polar uncharged amino acid or an aspartic acid or histidine at position 79 of the α chain; an aliphatic, polar uncharged amino acid, glutamic acid, lysine or arginine at position 81 of the α chain; an aliphatic, non-polar amino acid or a serine at position 83 of the α chain; an aliphatic, polar charged amino acid or a glutamine at position 90 of the α chain; an aliphatic, polar uncharged amino acid or alanine at position 92 of the α chain; an aliphatic, polar charged amino acid or asparagine at position 93 of the α chain; an aliphatic, polar uncharged amino acid or a isoleucine, leucine or valine at position 101 of the α chain;

wherein the one or more amino acid residues is not present in the corresponding germline TCR amino acid sequence; with the proviso that when the engineered TCR has only one altered amino acid compared to the corresponding germline sequence the one altered amino acid does not consist of an amino acid residue specified for the given position selected from group (I):

(I) L96 of the α chain; R9 of the β chain; Y10 of the β chain; T24 of the α chain; V19 of the α chain; T20 of the α chain; M50 of the α chain; T5 of the α chain; Q8 of the α chain; S86 of the α chain; F39 of the α chain; D55 of the α chain; R43 of the β chain; A66 of the α chain; V19 of the β chain; L21 of the β chain; L103 of the β chain; T3 of the α chain; S7 of the α chain; P9 of the α chain; M11 of the α chain; A16 of the α chain; T18 of the α chain; L21 of the α chain; S22 of the α chain; D26 of the α chain; F40 of the α chain; S47 of the α chain; R48 of the α chain; Q49 of the α chain; I51 of the α chain; L52 of the α chain; V53 of the α chain; T67 of the α chain; E68 of the α chain; N74 of the α chain; F76 of the α chain; N79 of the α chain; Q81 of the α chain; A83 of the α chain; K90 of the α chain; S92 of the α chain; D93 of the α chain; and M101 of the α chain; and when the TCR has two or more altered amino acid residues compared to the corresponding germline sequence at least one of the altered amino acid residues is not an amino acid residue specified for the given position in Group (I).

The one or more altered amino acid residues may be selected from Group (B) consisting of: an aliphatic, non-polar amino acid or a methionine at position 96 of the α chain; an aliphatic, polar charged amino acid or a glutamine at position 9 of the β chain; an aromatic amino acid at position 10 of the β chain; an aliphatic, polar uncharged amino acid at position 24 of the α chain; an aliphatic, non-polar amino acid or a methionine at position 19 of the α chain; an aliphatic, polar uncharged amino acid at position 20 of the α chain; an aliphatic, polar uncharged amino acid or a isoleucine, leucine or valine at position 50 of the α chain; an aliphatic, polar uncharged amino acid at position 5 of the α chain; an aliphatic, polar uncharged amino acid, a glutamic acid, lysine or arginine at position 8 of the α chain; an aliphatic, polar uncharged amino acid or alanine at position 86 of the α chain; an aromatic amino acid at position 39 of the α chain; an aliphatic, polar charged amino acid or asparagine at position 55 of the α chain; an aliphatic, polar charged amino acid or a glutamine at position 43 of the β chain;

with the proviso that when the engineered TCR has only one altered amino acid as selected from Group (B) compared to the corresponding germline sequence the one altered amino acid does not consist of an amino acid residue specified for the given position selected from group (II):

(II) L96 of the α chain; R9 of the β chain; Y10 of the β chain; T24 of the α chain; V19 of the α chain; T20 of the α chain; M50 of the α chain; T5 of the α chain; Q8 of the α chain; S86 of the α chain; F39 of the α chain; D55 of the α chain; R43 of the β chain; and when the TCR has two or more altered amino acid residues compared to the corresponding germline sequence at least one of the altered amino acid residues is not an amino acid residue specified for the given position in group (II).

The one or more amino acid residues may be selected from Group (C) consisting of: an aliphatic, non-polar amino acid or a methionine at position 96 of the α chain; an aliphatic, polar charged amino acid or a glutamine at position 9 of the β chain; an aromatic amino acid at position 10 of the β chain; an aliphatic, polar uncharged amino acid at position 24 of the α chain; an aliphatic, non-polar amino acid or a methionine at position 19 of the α chain; an aliphatic, polar uncharged amino acid at position 20 of the α chain; an aliphatic, polar uncharged amino acid or a isoleucine, leucine or valine at position 50 of the α chain; an aliphatic, polar uncharged amino acid at position 5 of the α chain; an aliphatic, polar uncharged amino acid, a glutamic acid, lysine or arginine at position 8 of the α chain; an aliphatic, polar uncharged amino acid or alanine at position 86 of the α chain;

with the proviso that when the engineered TCR has only one altered amino acid as selected from Group (C) compared to the corresponding germline sequence the one altered amino acid does not consist of an amino acid residue specified for the given position selected from group (III):

(III) L96 of the α chain; R9 of the β chain; Y10 of the β chain; T24 of the α chain; V19 of the α chain; T20 of the α chain; M50 of the α chain; T5 of the α chain; Q8 of the α chain; S86 of the α chain; and when the TCR has two or more altered amino acid residues compared to the corresponding germline sequence at least one of the altered amino acid residues is not an amino acid residue specified for the given position in group (III).

The engineered TCR may comprise an aliphatic, non-polar amino acid or a methionine at position 96 of the α chain and optionally one or more further amino acid residues at a given position as listed in Group (A); wherein the aliphatic, non-polar amino acid or a methionine at position 96 of the α chain and the one or more optional further amino acid residues at a given position as listed in Group (A) is not present in the corresponding germline TCR amino acid sequence; with the proviso that when the engineered TCR has only one altered amino acid which is an aliphatic, non-polar amino acid or a methionine at position 96 of the α chain compared to the corresponding germline sequence the altered amino acid is not L96 of the α chain; and when the TCR has two or more altered amino acid residues compared to the corresponding germline sequence at least one of the altered amino acid residues is not an amino acid residue specified for the given position in Group (I).

The engineered TCR may comprise an aliphatic, polar charged amino acid or a glutamine at position 9 of the β chain and optionally one or more further amino acid residue at a given position as listed in Group (A); wherein the aliphatic, polar charged amino acid or a glutamine at position 9 of the β chain and the one or more optional further amino acid residues at a given position as listed in Group (A) is not present in the corresponding germline TCR amino acid sequence; with the proviso that when the engineered TCR has only one altered amino acid which is an aliphatic, polar charged amino acid or a glutamine at position 9 of the β chain compared to the corresponding germline sequence the altered amino acid is not R9 of the β chain; and when the TCR has two or more altered amino acid residues compared to the corresponding germline sequence at least one of the altered amino acid residues is not an amino acid residue specified for the given position in Group (I).

The engineered TCR may comprise an aromatic amino acid at position 10 of the β chain and optionally one or more further amino acid residue at a given position as listed in Group (A); wherein the aromatic amino acid at position 10 of the β chain and the one or more optional further amino acid residues at a given position as listed in Group (A) is not present in the corresponding germline TCR amino acid sequence; with the proviso that when the engineered TCR has only one altered amino acid which is an aromatic amino acid at position 10 of the β chain compared to the corresponding germline sequence the altered amino acid is not Y10 of the β chain; and when the TCR has two or more altered amino acid residues compared to the corresponding germline sequence at least one of the altered amino acid residues is not an amino acid residue specified for the given position in Group (I).

The engineered TCR may comprise an aliphatic, polar uncharged amino acid at position 24 of the α chain and optionally one or more further amino acid residue at a given position as listed in Group (A); wherein the aliphatic, polar uncharged amino acid at position 24 of the α chain and the one or more optional further amino acid residues at a given position as listed in Group (A) is not present in the corresponding germline TCR amino acid sequence; with the proviso that when the engineered TCR has only one altered amino acid which is an aliphatic, polar uncharged amino acid at position 24 of the α chain compared to the corresponding germline sequence the altered amino acid is not T24 of the α chain; and when the TCR has two or more altered amino acid residues compared to the corresponding germline sequence at least one of the altered amino acid residues is not an amino acid residue specified for the given position in Group (I).

The engineered TCR may comprise an aliphatic, non-polar amino acid or a methionine at position 19 of the α chain and optionally one or more further amino acid residue at a given position as listed in Group (A); wherein the aliphatic, non-polar amino acid or a methionine at position 19 of the α chain and the one or more optional further amino acid residues at a given position as listed in Group (A) is not present in the corresponding germline TCR amino acid sequence; with the proviso that when the engineered TCR has only one altered amino acid which is an aliphatic, non-polar amino acid or a methionine at position 19 of the α chain compared to the corresponding germline sequence the altered amino acid is not V19 of the α chain; and when the TCR has two or more altered amino acid residues compared to the corresponding germline sequence at least one of the altered amino acid residues is not an amino acid residue specified for the given position in Group (I).

The engineered TCR may comprise an aliphatic, polar uncharged amino acid at position 20 of the α chain and optionally one or more further amino acid residue at a given position as listed in Group (A); wherein the aliphatic, polar uncharged amino acid at position 20 of the α chain and the one or more optional further amino acid residues at a given position as listed in Group (A) is not present in the corresponding germline TCR amino acid sequence; with the proviso that when the engineered TCR has only one altered amino acid which is an aliphatic, polar uncharged amino acid at position 20 of the α chain compared to the corresponding germline sequence the altered amino acid is not T20 of the α chain; and when the TCR has two or more altered amino acid residues compared to the corresponding germline sequence at least one of the altered amino acid residues is not an amino acid residue specified for the given position in Group (I).

The engineered TCR may comprise an aliphatic, polar uncharged amino acid or a isoleucine, leucine or valine at position 50 of the α chain and optionally one or more further amino acid residue at a given position as listed in Group (A); wherein the aliphatic, polar uncharged amino acid or a isoleucine, leucine or valine at position 50 of the α chain and the one or more optional further amino acid residues at a given position as listed in Group (A) is not present in the corresponding germline TCR amino acid sequence; with the proviso that when the engineered TCR has only one altered amino acid which is an aliphatic, polar uncharged amino acid or a isoleucine, leucine or valine at position 50 of the α chain compared to the corresponding germline sequence the altered amino acid is not M50 of the α chain; and when the TCR has two or more altered amino acid residues compared to the corresponding germline sequence at least one of the altered amino acid residues is not an amino acid residue specified for the given position in Group (I).

The engineered TCR may comprise an aliphatic, polar uncharged amino acid at position 5 of the α chain and optionally one or more further amino acid residue at a given position as listed in Group (A); wherein the aliphatic, polar uncharged amino acid at position 5 of the α chain and the one or more optional further amino acid residues at a given position as listed in Group (A) is not present in the corresponding germline TCR amino acid sequence; with the proviso that when the engineered TCR has only one altered amino acid which is an aliphatic, polar uncharged amino acid at position 5 of the α chain compared to the corresponding germline sequence the altered amino acid is not T5 of the α chain; and when the TCR has two or more altered amino acid residues compared to the corresponding germline sequence at least one of the altered amino acid residues is not an amino acid residue specified for the given position in Group (I).

The engineered TCR may comprise an aliphatic, polar uncharged amino acid, a glutamic acid, lysine or arginine at position 8 of the α chain and optionally one or more further amino acid residue at a given position as listed in Group (A); wherein the aliphatic, polar uncharged amino acid, glutamic acid, lysine or arginine at position 8 of the α chain and the one or more optional further amino acid residues at a given position as listed in Group (A) is not present in the corresponding germline TCR amino acid sequence; with the proviso that when the engineered TCR has only one altered amino acid which is an aliphatic, polar uncharged amino acid, a glutamic acid, lysine or arginine at position 8 of the α chain compared to the corresponding germline sequence the altered amino acid is not Q8 of the α chain; and when the TCR has two or more altered amino acid residues compared to the corresponding germline sequence at least one of the altered amino acid residues is not an amino acid residue specified for the given position in Group (I).

The engineered TCR may comprise an aliphatic, polar uncharged amino acid or alanine at position 86 of the α chain and optionally one or more further amino acid residue at a given position as listed in Group (A); wherein the aliphatic, polar uncharged amino acid or alanine at position 86 of the α chain and the one or more optional further amino acid residues at a given position as listed in Group (A) is not present in the corresponding germline TCR amino acid sequence; with the proviso that when the engineered TCR has only one altered amino acid which is an aliphatic, polar uncharged amino acid or alanine at position 86 of the α chain compared to the corresponding germline sequence the altered amino acid is not S86 of the α chain; and when the TCR has two or more altered amino acid residues compared to the corresponding germline sequence at least one of the altered amino acid residues is not an amino acid residue specified for the given position in Group (I).

The engineered TCR may comprise an aromatic amino acid at position 39 of the α chain and optionally one or more further amino acid residue at a given position as listed in Group (A); wherein the aromatic amino acid at position 39 of the α chain and the one or more optional further amino acid residues at a given position as listed in Group (A) is not present in the corresponding germline TCR amino acid sequence; with the proviso that when the engineered TCR has only one altered amino acid which is an aromatic amino acid at position 39 of the α chain compared to the corresponding germline sequence the altered amino acid is not F39 of the α chain; and when the TCR has two or more altered amino acid residues compared to the corresponding germline sequence at least one of the altered amino acid residues is not an amino acid residue specified for the given position in Group (I).

The engineered TCR may comprise an aliphatic, polar charged amino acid or asparagine at position 55 of the α chain and optionally one or more further amino acid residue at a given position as listed in Group (A); wherein the aliphatic, polar charged amino acid or asparagine at position 55 of the α chain and the one or more optional further amino acid residues at a given position as listed in Group (A) is not present in the corresponding germline TCR amino acid sequence; with the proviso that when the engineered TCR has only one altered amino acid which is an aliphatic, polar charged amino acid or asparagine at position 55 of the α chain compared to the corresponding germline sequence the altered amino acid is not D55 of the α chain; and when the TCR has two or more altered amino acid residues compared to the corresponding germline sequence at least one of the altered amino acid residues is not an amino acid residue specified for the given position in Group (I).

The engineered TCR may comprise an aliphatic, polar charged amino acid or a glutamine at position 43 of the β chain and optionally one or more further amino acid residue at a given position as listed in Group (A); wherein the aliphatic, polar charged amino acid or a glutamine at position 43 of the β chain and the one or more optional further amino acid residues at a given position as listed in Group (A) is not present in the corresponding germline TCR amino acid sequence; with the proviso that when the engineered TCR has only one altered amino acid which is an aliphatic, polar charged amino acid or a glutamine at position 43 of the β chain compared to the corresponding germline sequence the altered amino acid is not R43 of the α chain; and when the TCR has two or more altered amino acid residues compared to the corresponding germline sequence at least one of the altered amino acid residues is not an amino acid residue specified for the given position in Group (I).

The engineered TCR may comprise an aliphatic, non-polar amino acid or a methionine at position 96 of the α chain, an aliphatic, polar charged amino acid or a glutamine at position 9 of the β chain, and an aromatic amino acid at position 10 of the β chain, with the proviso that one of the altered amino acid compared to the corresponding germline sequence is not L96 of the α chain; R9 of the β chain; or Y10 of the β chain.

Without wishing to be bound by theory, the present inventors consider that—by way of example—an aliphatic, non-polar amino acid or a methionine at position 96 of the α chain; an aliphatic, polar charged amino acid or a glutamine at position 9 of the β chain; and/or an aromatic amino acid at position 10 of the β chain improves the interaction between the variable and constant regions of the alpha and beta chains of the present TCR, respectively. For example, an aliphatic, non-polar amino acid or a methionine at position 96 of the α chain improves interaction between the variable and constant regions of the alpha chain and an aliphatic, polar charged amino acid or a glutamine at position 9 of the β chain; and/or an aromatic amino acid at position 10 of the β chain improves interaction between the variable and constant regions of the beta chain.

The engineered TCR may comprise an aliphatic, non-polar amino acid or a methionine at position 19 of the α chain, an aliphatic, polar charged amino acid or a glutamine at position 9 of the β chain, and an aromatic amino acid at position 10 of the β chain, with the proviso that one of the altered amino acid compared to the corresponding germline sequence is not V19 of the α chain; R9 of the β chain; or Y10 of the β chain.

The engineered TCR may comprise an aliphatic, polar charged amino acid or a glutamine at position 9 of the β chain, and an aromatic amino acid at position 10 of the β chain, with the proviso that one of the altered amino acids compared to the corresponding germline sequence is not R9 of the β chain or Y10 of the β chain.

The term "one or more" as used herein may include one, two, three, four, five, six, seven, eight, nine, ten, eleven, twelve, thirteen, fourteen, fifteen, sixteen, seventeen, eighteen, nineteen, twenty or more amino acid residues as described herein.

The term "two or more" as used herein may include two, three, four, five, six, seven, eight, nine, ten, eleven, twelve, thirteen, fourteen, fifteen, sixteen, seventeen, eighteen, nineteen, twenty or more amino acid residues as described herein.

The engineered TCR may comprise a plurality of the amino acid residues recited above. In other words, the TCR may comprise at least 2, at least 3, at least 4, at least 5, at least 6, at least 7, at least 8, at least 9, at least 10, at least 15 or at least 20 of the amino acid residues recited above.

The engineered TCR may have each of the amino acid residues selected from Group (A); with the proviso that at least one of the altered amino acid residues is not an amino acid residue specified for the given position in Group (I).

In one embodiment, the engineered TCR may comprise each of an aliphatic, non-polar amino acid or a methionine at position 96 of the α chain; an aliphatic, polar charged amino acid or a glutamine at position 9 of the β chain; an aromatic amino acid at position 10 of the β chain; an aliphatic, polar uncharged amino acid at position 24 of the α chain; an aliphatic, non-polar amino acid or a methionine at position 19 of the α chain; an aliphatic, polar uncharged amino acid at position 20 of the α chain; an aliphatic, polar uncharged amino acid or a isoleucine, leucine or valine at position 50 of the α chain; an aliphatic, polar uncharged amino acid at position 5 of the α chain; an aliphatic, polar uncharged amino acid, a glutamic acid, lysine or arginine at position 8 of the α chain; an aliphatic, polar uncharged amino acid or alanine at position 86 of the α chain; an aromatic amino acid at position 39 of the α chain; an aliphatic, polar charged amino acid or asparagine at position 55 of the α chain; an aliphatic, polar charged amino acid or a glutamine at position 43 of the β chain; with the proviso that at least one of the altered amino acid residues is not an amino acid residue specified for the given position selected from the group of L96 of the α chain; R9 of the β chain; Y10 of the β chain; T24 of the α chain; V19 of the α chain; T20 of the α chain; M50 of the α chain; T5 of the α chain; Q8 of the α chain; S86 of the α chain; F39 of the α chain; D55 of the α chain; R43 of the β chain.

In one embodiment, the engineered TCR may comprise each of an aliphatic, non-polar amino acid or a methionine at position 96 of the α chain; an aliphatic, polar charged amino acid or a glutamine at position 9 of the β chain; an aromatic amino acid at position 10 of the β chain; an aliphatic, polar uncharged amino acid at position 24 of the α chain; an aliphatic, non-polar amino acid or a methionine at position 19 of the α chain; an aliphatic, polar uncharged amino acid at position 20 of the α chain; an aliphatic, polar uncharged amino acid or a isoleucine, leucine or valine at position 50 of the α chain; an aliphatic, polar uncharged amino acid at position 5 of the α chain; an aliphatic, polar uncharged amino acid, a glutamic acid, lysine or arginine at position 8 of the α chain; an aliphatic, polar uncharged amino acid or alanine at position 86 of the α chain; with the proviso that at least one of the altered amino acid residues is not an amino acid residue specified for the given position selected from the group of L96 of the α chain; R9 of the β chain; Y10 of the β chain; T24 of the α chain; V19 of the α chain; T20 of the α chain; M50 of the α chain; T5 of the α chain; Q8 of the α chain; S86 of the α chain.

In one embodiment, the present TCR does not comprise at least one of the following amino acid residues: L96 of the α chain; R9 of the β chain; Y10 of the β chain; T24 of the α chain; V19 of the α chain; T20 of the α chain; M50 of the α chain; T5 of the α chain; Q8 of the α chain; S86 of the α chain; F39 of the α chain; D55 of the α chain; R43 of the β chain; A66 of the α chain; V19 of the β chain; L21 of the β chain; L103 of the β chain; T3 of the α chain; S7 of the α chain; P9 of the α chain; M11 of the α chain; A16 of the α chain; T18 of the α chain; L21 of the α chain; S22 of the α chain; D26 of the α chain; F40 of the α chain; S47 of the α chain; R48 of the α chain; Q49 of the α chain; I51 of the α chain; L52 of the α chain; V53 of the α chain; T67 of the α chain; E68 of the α chain; N74 of the α chain; F76 of the α chain; N79 of the α chain; Q81 of the α chain; A83 of the α chain; K90 of the α chain; S92 of the α chain; D93 of the α chain; and M101 of the α chain; wherein the at least one amino acid residue is not present in the corresponding germline TCR amino acid sequence.

In one embodiment, the present TCR does not comprise at least one amino acid residue may be selected from a list of: L96 of the α chain; R9 of the β chain; Y10 of the β chain; T24 of the α chain; V19 of the α chain; T20 of the α chain; M50 of the α chain; T5 of the α chain; Q8 of the α chain; S86 of the α chain; F39 of the α chain; D55 of the α chain; and R43 of the β chain.

In one embodiment, the present TCR does not comprise at least one amino acid residue selected from a list of: L96 of the α chain; R9 of the β chain; Y10 of the β chain; T24 of the α chain; V19 of the α chain; T20 of the α chain; M50 of the α chain; T5 of the α chain; Q8 of the α chain; and S86 of the α chain.

In one embodiment, the present TCR does not comprise L96 of the α chain. In one embodiment, the TCR does not comprise L96 of the α chain and at least one of R9 of the β chain; Y10 of the β chain; T24 of the α chain; V19 of the α chain; T20 of the α chain; M50 of the α chain; T5 of the α chain; Q8 of the α chain; S86 of the α chain; F39 of the α chain; D55 of the α chain; R43 of the β chain; A66 of the α chain; V19 of the β chain; L21 of the β chain; L103 of the β chain; T3 of the α chain; S7 of the α chain; P9 of the α chain; M11 of the α chain; A16 of the α chain; T18 of the α chain; L21 of the α chain; S22 of the α chain; D26 of the α chain; F40 of the α chain; S47 of the α chain; R48 of the α chain; Q49 of the α chain; I51 of the α chain; L52 of the α chain; V53 of the α chain; T67 of the α chain; E68 of the α chain; N74 of the α chain; F76 of the α chain; N79 of the α chain; Q81 of the α chain; A83 of the α chain; K90 of the α chain; S92 of the α chain; D93 of the α chain; and M101 of the α chain.

In one embodiment, the present TCR does not comprise L96 of the α chain; R9 of the β chain and Y10 of the β chain.

In one embodiment, the present TCR does not comprise V19 of the α chain; R9 of the β chain and Y10 of the β chain.

In one embodiment, the present TCR does not comprise R9 of the β chain. In one embodiment, the TCR does not comprise R9 of the β chain and at least one of L96 of the α chain; Y10 of the β chain; T24 of the α chain; V19 of the α chain; T20 of the α chain; M50 of the α chain; T5 of the α chain; Q8 of the α chain; S86 of the α chain; F39 of the α chain; D55 of the α chain; R43 of the β chain; A66 of the α chain; V19 of the β chain; L21 of the β chain; L103 of the β chain; T3 of the α chain; S7 of the α chain; P9 of the α chain; M11 of the α chain; A16 of the α chain; T18 of the α chain; L21 of the α chain; S22 of the α chain; D26 of the α chain; F40 of the α chain; S47 of the α chain; R48 of the α chain; Q49 of the α chain; I51 of the α chain; L52 of the α chain; V53 of the α chain; T67 of the α chain; E68 of the α chain; N74 of the α chain; F76 of the α chain; N79 of the α chain; Q81 of the α chain; A83 of the α chain; K90 of the α chain; S92 of the α chain; D93 of the α chain; and M101 of the α chain In one embodiment, the present TCR does not comprise Y10 of the β chain. In one embodiment, the TCR does not comprise Y10 of the β chain and at least one of L96 of the α chain; R9 of the β chain; T24 of the α chain; V19 of the α chain; T20 of the α chain; M50 of the α chain; T5 of the α chain; Q8 of the α chain; S86 of the α chain; F39 of the α chain; D55 of the α chain; R43 of the β chain; A66 of the α chain; V19 of the β chain; L21 of the β chain; L103 of the β chain; T3 of the α chain; S7 of the α chain; P9 of the α chain; M11 of the α chain; A16 of the α chain; T18 of the α chain; L21 of the α chain; S22 of the α chain; D26 of the α chain; F40 of the α chain; S47 of the α chain; R48 of the α chain; Q49 of the α chain; I51 of the α chain; L52 of the α chain; V53 of the α chain; T67 of the α chain; E68 of the α chain; N74 of the α chain; F76 of the α chain; N79 of the α chain; Q81 of the α chain; A83 of the α chain; K90 of the α chain; S92 of the α chain; D93 of the α chain; and M101 of the α chain.

In one embodiment, the present TCR does not comprise T24 of the α chain. In one embodiment, the TCR does not comprise T24 of the α chain and at least one of L96 of the α chain; R9 of the β chain; Y10 of the β chain; V19 of the α chain; T20 of the α chain; M50 of the α chain; T5 of the α chain; Q8 of the α chain; S86 of the α chain; F39 of the α chain; D55 of the α chain; R43 of the β chain; A66 of the α chain; V19 of the β chain; L21 of the β chain; L103 of the β chain; T3 of the α chain; S7 of the α chain; P9 of the α chain; M11 of the α chain; A16 of the α chain; T18 of the α chain; L21 of the α chain; S22 of the α chain; D26 of the α chain; F40 of the α chain; S47 of the α chain; R48 of the α chain; Q49 of the α chain; I51 of the α chain; L52 of the α chain; V53 of the α chain; T67 of the α chain; E68 of the α chain; N74 of the α chain; F76 of the α chain; N79 of the α chain; Q81 of the α chain; A83 of the α chain; K90 of the α chain; S92 of the α chain; D93 of the α chain; and M101 of the α chain.

In one embodiment, the present TCR does not comprise V19 of the α chain. In one embodiment, the TCR does not comprise V19 of the α chain and at least one of L96 of the α chain; R9 of the β chain; Y10 of the β chain; T24 of the α chain; T20 of the α chain; M50 of the α chain; T5 of the α chain; Q8 of the α chain; S86 of the α chain; F39 of the α chain; D55 of the α chain; R43 of the β chain; A66 of the α chain; V19 of the β chain; L21 of the β chain; L103 of the β chain; T3 of the α chain; S7 of the α chain; P9 of the α chain; M11 of the α chain; A16 of the α chain; T18 of the α chain; L21 of the α chain; S22 of the α chain; D26 of the α chain; F40 of the α chain; S47 of the α chain; R48 of the α chain; Q49 of the α chain; I51 of the α chain; L52 of the α chain; V53 of the α chain; T67 of the α chain; E68 of the α chain; N74 of the α chain; F76 of the α chain; N79 of the α chain; Q81 of the α chain; A83 of the α chain; K90 of the α chain; S92 of the α chain; D93 of the α chain; and M101 of the α chain.

In one embodiment, the present TCR does not comprise T20 of the α chain. In one embodiment, the TCR does not comprise T20 of the α chain and at least one of L96 of the α chain; R9 of the β chain; Y10 of the β chain; T24 of the α chain; V19 of the α chain; M50 of the α chain; T5 of the α chain; Q8 of the α chain; S86 of the α chain; F39 of the α chain; D55 of the α chain; R43 of the β chain; A66 of the α chain; V19 of the β chain; L21 of the β chain; L103 of the β chain; T3 of the α chain; S7 of the α chain; P9 of the α chain; M11 of the α chain; A16 of the α chain; T18 of the α chain; L21 of the α chain; S22 of the α chain; D26 of the α chain; F40 of the α chain; S47 of the α chain; R48 of the α chain; Q49 of the α chain; I51 of the α chain; L52 of the α chain; V53 of the α chain; T67 of the α chain; E68 of the α chain; N74 of the α chain; F76 of the α chain; N79 of the α chain; Q81 of the α chain; A83 of the α chain; K90 of the α chain; S92 of the α chain; D93 of the α chain; and M101 of the α chain.

In one embodiment, the present TCR does not comprise M50 of the α chain. In one embodiment, the TCR does not comprise M50 of the α chain and at least one of L96 of the α chain; R9 of the β chain; Y10 of the β chain; T24 of the α chain; V19 of the α chain; T20 of the α chain; T5 of the α chain; Q8 of the α chain; S86 of the α chain; F39 of the α chain; D55 of the α chain; R43 of the β chain; A66 of the α chain; V19 of the β chain; L21 of the β chain; L103 of the β chain; T3 of the α chain; S7 of the α chain; P9 of the α chain; M11 of the α chain; A16 of the α chain; T18 of the α chain; L21 of the α chain; S22 of the α chain; D26 of the α chain; F40 of the α chain; S47 of the α chain; R48 of the α chain; Q49 of the α chain; I51 of the α chain; L52 of the α chain; V53 of the α chain; T67 of the α chain; E68 of the α chain; N74 of the α chain; F76 of the α chain; N79 of the α chain; Q81 of the α chain; A83 of the α chain; K90 of the α chain; S92 of the α chain; D93 of the α chain; and M101 of the α chain.

In one embodiment, the present TCR does not comprise T5 of the α chain. In one embodiment, the TCR does not comprise T5 of the α chain and at least one of L96 of the α chain; R9 of the β chain; Y10 of the β chain; T24 of the α chain; V19 of the α chain; T20 of the α chain; M50 of the α chain; Q8 of the α chain; S86 of the α chain; F39 of the α chain; D55 of the α chain; R43 of the β chain; A66 of the α chain; V19 of the β chain; L21 of the β chain; L103 of the β chain; T3 of the α chain; S7 of the α chain; P9 of the α chain; M11 of the α chain; A16 of the α chain; T18 of the α chain; L21 of the α chain; S22 of the α chain; D26 of the α chain; F40 of the α chain; S47 of the α chain; R48 of the α chain; Q49 of the α chain; I51 of the α chain; L52 of the α chain; V53 of the α chain; T67 of the α chain; E68 of the α chain; N74 of the α chain; F76 of the α chain; N79 of the α chain; Q81 of the α chain; A83 of the α chain; K90 of the α chain; S92 of the α chain; D93 of the α chain; and M101 of the α chain.

In one embodiment, the present TCR does not comprise Q8 of the α chain. In one embodiment, the TCR does not comprise Q8 of the α chain and at least one of L96 of the α chain; R9 of the β chain; Y10 of the β chain; T24 of the α chain; V19 of the α chain; T20 of the α chain; M50 of the α chain; T5 of the α chain; S86 of the α chain; F39 of the α chain; D55 of the α chain; R43 of the β chain; A66 of the α chain; V19 of the β chain; L21 of the β chain; L103 of the β chain; T3 of the α chain; S7 of the α chain; P9 of the α chain; M11 of the α chain; A16 of the α chain; T18 of the α chain; L21 of the α chain; S22 of the α chain; D26 of the α chain; F40 of the α chain; S47 of the α chain; R48 of the α chain; Q49 of the α chain; I51 of the α chain; L52 of the α chain; V53 of the α chain; T67 of the α chain; E68 of the α chain; N74 of the α chain; F76 of the α chain; N79 of the α chain; Q81 of the α chain; A83 of the α chain; K90 of the α chain; S92 of the α chain; D93 of the α chain; and M101 of the α chain.

In one embodiment, the present TCR does not comprise S86 of the α chain. In one embodiment, the TCR does not comprise S86 of the α chain and at least one of L96 of the α chain; R9 of the β chain; Y10 of the β chain; T24 of the α chain; V19 of the α chain; T20 of the α chain; M50 of the α chain; T5 of the α chain; Q8 of the α chain; F39 of the α chain; D55 of the α chain; R43 of the β chain; A66 of the α chain; V19 of the β chain; L21 of the β chain; L103 of the β chain; T3 of the α chain; S7 of the α chain; P9 of the α chain; M11 of the α chain; A16 of the α chain; T18 of the α chain; L21 of the α chain; S22 of the α chain; D26 of the α chain; F40 of the α chain; S47 of the α chain; R48 of the α chain; Q49 of the α chain; I51 of the α chain; L52 of the α chain; V53 of the α chain; T67 of the α chain; E68 of the α chain; N74 of the α chain; F76 of the α chain; N79 of the α chain; Q81 of the α chain; A83 of the α chain; K90 of the α chain; S92 of the α chain; D93 of the α chain; and M101 of the α chain.

In one embodiment, the present TCR does not comprise F39 of the α chain. In one embodiment, the TCR does not comprise F39 of the α chain and at least one of L96 of the α chain; R9 of the β chain; Y10 of the β chain; T24 of the α chain; V19 of the α chain; T20 of the α chain; M50 of the α chain; T5 of the α chain; Q8 of the α chain; S86 of the α chain; D55 of the α chain; R43 of the β chain; A66 of the α chain; V19 of the β chain; L21 of the β chain; L103 of the β chain; T3 of the α chain; S7 of the α chain; P9 of the α chain; M11 of the α chain; A16 of the α chain; T18 of the α chain; L21 of the α chain; S22 of the α chain; D26 of the α chain; F40 of the α chain; S47 of the α chain; R48 of the α chain; Q49 of the α chain; I51 of the α chain; L52 of the α chain; V53 of the α chain; T67 of the α chain; E68 of the α chain; N74 of the α chain; F76 of the α chain; N79 of the α chain; Q81 of the α chain; A83 of the α chain; K90 of the α chain; S92 of the α chain; D93 of the α chain; and M101 of the α chain.

In one embodiment, the present TCR does not comprise D55 of the α chain. In one embodiment, the TCR does not comprise D55 of the α chain and at least one of L96 of the α chain; R9 of the β chain; Y10 of the β chain; T24 of the α chain; V19 of the α chain; T20 of the α chain; M50 of the α chain; T5 of the α chain; Q8 of the α chain; S86 of the α chain; F39 of the α chain; R43 of the β chain; A66 of the α chain; V19 of the β chain; L21 of the β chain; L103 of the β chain; T3 of the α chain; S7 of the α chain; P9 of the α chain; M11 of the α chain; A16 of the α chain; T18 of the α chain; L21 of the α chain; S22 of the α chain; D26 of the α chain; F40 of the α chain; S47 of the α chain; R48 of the α chain; Q49 of the α chain; I51 of the α chain; L52 of the α chain; V53 of the α chain; T67 of the α chain; E68 of the α chain; N74 of the α chain; F76 of the α chain; N79 of the α chain; Q81 of the α chain; A83 of the α chain; K90 of the α chain; S92 of the α chain; D93 of the α chain; and M101 of the α chain.

In one embodiment, the present TCR does not comprise R43 of the β chain. In one embodiment, the TCR does not comprise R43 of the β chain and at least one of L96 of the α chain; R9 of the β chain; Y10 of the β chain; T24 of the α chain; V19 of the α chain; T20 of the α chain; M50 of the α chain; T5 of the α chain; Q8 of the α chain; S86 of the α chain; F39 of the α chain; D55 of the α chain; A66 of the α chain; V19 of the β chain; L21 of the β chain; L103 of the β chain; T3 of the α chain; S7 of the α chain; P9 of the α chain; M11 of the α chain; A16 of the α chain; T18 of the α chain; L21 of the α chain; S22 of the α chain; D26 of the α chain; F40 of the α chain; S47 of the α chain; R48 of the α chain; Q49 of the α chain; I51 of the α chain; L52 of the α chain; V53 of the α chain; T67 of the α chain; E68 of the α chain; N74 of the α chain; F76 of the α chain; N79 of the α chain; Q81 of the α chain; A83 of the α chain; K90 of the α chain; S92 of the α chain; D93 of the α chain; and M101 of the α chain.

In one embodiment, the present TCR does not comprise R9 and Y10 in the β chain.

In one embodiment, the present TCR does not comprise each of L96 of the α chain; R9 of the β chain; Y10 of the β chain; T24 of the α chain; V19 of the α chain; T20 of the α chain; M50 of the α chain; T5 of the α chain; Q8 of the α chain; S86 of the α chain; F39 of the α chain; D55 of the α chain; R43 of the β chain; A66 of the α chain; V19 of the β chain; L21 of the β chain; L103 of the β chain; T3 of the α chain; S7 of the α chain; P9 of the α chain; M11 of the α chain; A16 of the α chain; T18 of the α chain; L21 of the α chain; S22 of the α chain; D26 of the α chain; F40 of the α chain; S47 of the α chain; R48 of the α chain; Q49 of the α chain; I51 of the α chain; L52 of the α chain; V53 of the α chain; T67 of the α chain; E68 of the α chain; N74 of the α chain; F76 of the α chain; N79 of the α chain; Q81 of the α chain; A83 of the α chain; K90 of the α chain; S92 of the α chain; D93 of the α chain; and M101 of the α chain;

In one embodiment, the present TCR does not comprise each of L96 of the α chain; R9 of the β chain; Y10 of the β chain; T24 of the α chain; V19 of the α chain; T20 of the α chain; M50 of the α chain; T5 of the α chain; Q8 of the α chain; S86 of the α chain; F39 of the α chain; D55 of the α chain; and R43 of the β chain.

In one embodiment, the present TCR does not comprise each of L96 of the α chain; R9 of the β chain; Y10 of the β chain; T24 of the α chain; V19 of the α chain; T20 of the α chain; M50 of the α chain; T5 of the α chain; Q8 of the α chain; and S86 of the α chain.

Conservative Substitution

Suitably, the amino acid residues present at a given position in the present invention may be defined as a residue which is biochemically similar to the amino acids recited for the given positions in group (I):

(1) L96 of the α chain; R9 of the β chain; Y10 of the β chain; T24 of the α chain; V19 of the α chain; T20 of the α chain; M50 of the α chain; T5 of the α chain; Q8 of the α chain; S86 of the α chain; F39 of the α chain; D55 of the α chain; R43 of the β chain; A66 of the α chain; V19 of the β chain; L21 of the β chain; L103 of the β chain; T3 of the α chain; S7 of the α chain; P9 of the α chain; M11 of the α chain; A16 of the α chain; T18 of the α chain; L21 of the α chain; S22 of the α chain; D26 of the α chain; F40 of the α chain; S47 of the α chain; R48 of the α chain; Q49 of the α chain; I51 of the α chain; L52 of the α chain; V53 of the α chain; T67 of the α chain; E68 of the α chain; N74 of the α chain; F76 of the α chain; N79 of the α chain; Q81 of the α chain; A83 of the α chain; K90 of the α chain; S92 of the α chain; D93 of the α chain; and M101 of the α chain.

Amino acids with similar biochemical properties may be defined as amino acids which can be substituted via a conservative substitution.

Conservative amino acid substitutions may be made on the basis of similarity in polarity, charge, solubility, hydrophobicity, hydrophilicity, and/or the amphipathic nature of the residues as long as high expression of the TCR is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example according to Table 1 below. Amino acids in the same block in the second column and preferably in the same line in the third column may be substituted for each other:

TABLE 1

| ALIPHATIC | Non-polar | G A P |
| | | I L V |
| | Polar-uncharged | C S T M |
| | | N Q |

TABLE 1-continued

| | Polar-charged | D E |
| | | K R |
| AROMATIC | | H F W Y |

The present invention also encompasses homologous substitution (substitution and replacement are both used herein to mean the interchange of an existing amino acid residue, with an alternative residue) i.e. like-for-like substitution such as basic for basic, acidic for acidic, polar for polar etc.

An aliphatic, non-polar amino acid may be a glycine, alanine, proline, isoleucine, leucine or valine residue.

An aliphatic, polar uncharged amino may be a cysteine, serine, threonine, methionine, asparagine or glutamine residue.

An aliphatic, polar charged amino acid may be an aspartic acid, glutamic acid, lysine or arginine residue.

An aromatic amino acid may be a histidine, phenylalanine, tryptophan or tyrosine residue.

Suitably, a conservative substitution may be made between amino acids in the same line in Table 1. Accordingly, an amino acid residue identified at a given position in Group (I) above may be substituted with an amino acid residue representing a conservative substitution as described herein.

Glycine, alanine and proline may be substituted as a conservative substitution.

Isoleucine, leucine and valine may be substituted as a conservative substitution.

Cysteine, serine, threonine and methionine may be substituted as a conservative substitution.

Asparagine and glutamine may be substituted as a conservative substitution.

Aspartic acid and glutamic acid may be substituted as a conservative substitution.

Lysine and arginine may be substituted as a conservative substitution.

Histidine, phenylalanine, tryptophan and tyrosine may be substituted as a conservative substitution.

Leucine may be substituted with an isoleucine or valine.
Arginine may be substituted with a lysine.
Tyrosine may be substituted with a phenylalanine, histidine or tryptophan.
Threonine may be substituted with a cysteine, serine or methionine. Suitably, Threonine may be substituted with a serine or methionine.
Valine may be substituted with an isoleucine or leucine.
Methionine may be substituted with cysteine, serine or threonine. Suitably methionine may be substituted with a serine or threonine.
Glutamine may be substituted with an asparagine.
Serine may be substituted with a cysteine, threonine or methionine.
Serine may be substituted with a threonine or methionine.
Phenylalanine may be substituted with a tyrosine, histidine or tryptophan.
Aspartic acid may be substituted with a glutamic acid.
Alanine may be substituted with a glycine or proline.
Isoleucine may be substituted with a leucine or valine.
Glutamic acid may be substituted with an aspartic acid.
Asparagine may be substituted with a glutamine.
Lysine may be substituted with an arginine.
Suitably, conservative substitutions may be identified using the BLOSUM62 matrix. This system provide a score for a given amino acid pair based on the frequency of finding a substitution between that pair of amino acids in homologous proteins (see Henikoff, J. G. Amino acid substitution matrices from protein blocks. Proc. Natl. Acad. Sci. USA 89, 10915-10919 (1992)).

A matrix of BLOSUM62 scores is shown as FIG. 19.

Suitably, a conservative substitution may be made between any two amino acids which have a BLOSUM62 score of greater than 0.

Suitably a leucine may be substituted with an isoleucine, valine or methionine.

Suitably an arginine may be substituted with a lysine or glutamine.

Suitably a tyrosine may be substituted with a phenylalanine, histidine or tryptophan.

Suitably a threonine may be substituted with a serine.

Suitably a valine may be substituted with an isoleucine, leucine or methionine.

Suitably a methionine may be substituted with an isoleucine, leucine or valine.

Suitably a glutamine may be substituted with a glutamic acid, lysine or arginine.

Suitably a serine may be substituted with an alanine, asparagine or threonine.

Suitably a phenylalanine may be substituted with a tyrosine or tryptophan.

Suitably an aspartic acid may be substituted with a glutamic acid or asparagine.

Suitably an alanine may be substituted with a serine.

Suitably an isoleucine may be substituted with a leucine, valine or methionine.

Suitably a glutamic acid may be substituted with an aspartic acid, glutamine or lysine.

Suitably an asparagine may be substituted with an aspartic acid, histidine or serine.

Suitably a lysine may be substituted with an arginine, glutamic acid or glutamine.

Nucleic Acid Sequence

The present invention further provides a nucleotide sequence encoding an engineered TCR receptor as described herein or a part thereof, for example the variable sequence of the α chain or the β chain; the α chain and/or the β chain.

As used herein, the terms "polynucleotide" and "nucleic acid" are intended to be synonymous with each other.

It will be understood by a skilled person that numerous different polynucleotides and nucleic acids can encode the same polypeptide as a result of the degeneracy of the genetic code. In addition, it is to be understood that skilled persons may, using routine techniques, make nucleotide substitutions that do not affect the polypeptide sequence encoded by the polynucleotides described here to reflect the codon usage of any particular host organism in which the polypeptides are to be expressed.

Nucleic acids according to the invention may comprise DNA or RNA. They may be single-stranded or double-stranded. They may also be polynucleotides which include within them synthetic or modified nucleotides. A number of different types of modification to oligonucleotides are known in the art. These include methylphosphonate and phosphorothioate backbones, addition of acridine or polylysine chains at the 3' and/or 5' ends of the molecule. For the purposes of the use as described herein, it is to be understood that the polynucleotides may be modified by any method available in the art. Such modifications may be carried out in order to enhance the in vivo activity or life span of polynucleotides of interest.

The polynucleotide may be double or single stranded, and may be RNA or DNA.

The polynucleotide may be codon optimised. Different cells differ in their usage of particular codons. This codon bias corresponds to a bias in the relative abundance of particular tRNAs in the cell type. By altering the codons in the sequence so that they are tailored to match with the relative abundance of corresponding tRNAs, it is possible to increase expression.

Many viruses, including HIV and other lentiviruses, use a large number of rare codons and by changing these to correspond to commonly used mammalian codons, increased expression of the packaging components in mammalian producer cells can be achieved. Codon usage tables are known in the art for mammalian cells, as well as for a variety of other organisms.

Codon optimisation may also involve the removal of mRNA instability motifs and cryptic splice sites.

The polynucleotide may comprise a nucleic acid sequence which enables both a nucleic acid sequence encoding an α chain and a nucleic acid sequence a β chain to be expressed from the same mRNA transcript.

For example, the polynucleotide may comprise an internal ribosome entry site (IRES) between the nucleic acid sequences which encode the α chain and the β chain. An IRES is a nucleotide sequence that allows for translation initiation in the middle of a mRNA sequence.

The polynucleotide may comprise a nucleic acid sequence encoding an α chain and a nucleic acid sequence a β chain linked by an internal self-cleaving sequence.

The internal self-cleaving sequence may be any sequence which enables the polypeptide comprising the α chain and the polypeptide comprising the β chain to become separated.

The cleavage site may be self-cleaving, such that when the polypeptide is produced, it is immediately cleaved into individual peptides without the need for any external cleavage activity.

The term "cleavage" is used herein for convenience, but the cleavage site may cause the peptides to separate into individual entities by a mechanism other than classical cleavage. For example, for the Foot-and-Mouth disease virus (FMDV) 2A self-cleaving peptide (see below), various models have been proposed for to account for the "cleavage" activity: proteolysis by a host-cell proteinase, autoproteolysis or a translational effect (Donnelly et al (2001) J. Gen. Virol. 82:1027-1041). The exact mechanism of such "cleavage" is not important for the purposes of the present invention, as long as the cleavage site, when positioned between nucleic acid sequences which encode proteins, causes the proteins to be expressed as separate entities.

The self-cleaving peptide may be a 2A self-cleaving peptide from an aphtho- or a cardiovirus.

Vector

The present invention also provides a vector comprising a nucleotide sequence as described herein.

The term "vector" includes an expression vector, i.e. a construct capable of in vivo or in vitro/ex vivo expression. Also encompassed are cloning vectors.

Viral delivery systems include but are not limited to adenovirus vector, an adeno-associated viral (AAV) vector, a herpes viral vector, retroviral vector, lentiviral vector, baculoviral vector.

Retroviruses are RNA viruses with a life cycle different to that of lytic viruses. In this regard, a retrovirus is an infectious entity that replicates through a DNA intermediate. When a retrovirus infects a cell, its genome is converted to a DNA form by a reverse transcriptase enzyme. The DNA copy serves as a template for the production of new RNA genomes and virally encoded proteins necessary for the assembly of infectious viral particles.

There are many retroviruses, for example murine leukemia virus (MLV), human immunodeficiency virus (HIV), equine infectious anaemia virus (EIAV), mouse mammary tumour virus (MMTV), Rous sarcoma virus (RSV), Fujinami sarcoma virus (FuSV), Moloney murine leukemia virus (Mo-MLV), FBR murine osteosarcoma virus (FBR MSV), Moloney murine sarcoma virus (Mo-MSV), Abelson murine leukemia virus (A-MLV), Avian myelocytomatosis virus-29 (MC29), and Avian erythroblastosis virus (AEV) and all other retroviridiae including lentiviruses.

A detailed list of retroviruses may be found in Coffin et al ("Retroviruses" 1997 Cold Spring Harbour Laboratory Press Eds: J M Coffin, S M Hughes, H E Varmus pp 758-763).

Lentiviruses also belong to the retrovirus family, but they can infect both dividing and non-dividing cells (Lewis et al (1992) EMBO J. 3053-3058).

The vector may be capable of transferring a nucleotide according to the second aspect of the invention to a cell, such as a T-cell. The vector should ideally be capable of sustained high-level expression in T cells, so that the introduced TCR may compete successfully with the endogenous TCR for a limited pool of CD3 molecules.

The vector may be a retroviral vector. The vector may be based on or derivable from the MP71 vector backbone. The vector may lack a full-length or truncated version of the Woodchuck Hepatitis Response Element (WPRE).

For efficient infection of human cells, viral particles may be packaged with amphotropic envelopes or gibbon ape leukemia virus envelopes.

Increasing the supply of CD3 molecules may increase TCR expression in gene modified cells. The vector may therefore also comprise the genes for CD3-gamma, CD3-delta, CD3-epsilon and/or CD3-zeta. The vector may just comprise the gene for CD3-zeta. The genes may be linked by self-cleaving sequences, such as the 2A self-cleaving sequence. Alternatively one or more separate vectors may be provided encoding CD3 gene for co-transfer with the TCR-encoding vector(s).

Cell

The present invention further relates to a cell which comprises a polynucleotide according to the present invention. The cell may express a T-cell receptor of the invention.

The cell may a mammalian cell, in particular a human cell.

The cell may be a T-cell. The T-cell may be any T-cell subset, including for example, $\alpha\beta$ T-cell, $\gamma\delta$ T-cell or regulatory T cells.

The cell may be a natural killer cell.

The cell may be a natural killer T cell.

The cell may be derived from a cell isolated from a subject. The cell may be part of a mixed cell population isolated from the subject, such as a population of peripheral blood lymphocytes (PBL).

T cells within the PBL population may be activated by methods known in the art, such as using anti-CD3 and CD28 antibodies.

The T-cell may be a CD4+ helper T cell or a CD8+ cytotoxic T cell. The cell may be in a mixed population of CD4+ helper T cell/CD8+ cytotoxic T cells. Polyclonal activation, for example using anti-CD3 antibodies optionally in combination with anti-CD28 antibodies will trigger the proliferation of CD4+ and CD8+ T cells, but may also trigger the proliferation of CD4+25+ regulatory T-cells.

In one embodiment the T cell is a CD8+ cytotoxic T cell.

In one embodiment a cell which expresses an engineered TCR according to the present invention may have increased functional activity compared to a cell which expresses the corresponding TCR comprising the unmodified germline TCR sequence.

Increased functional activity may refer, for example, to increased cytokine production by the cell following binding of antigen to the TCR. The cytokine may be selected from IFN$\gamma$, IL-2, GM-CSF, TNFalpha, IL-4, IL-5, IL-6, IL-9, IL-10 and IL-13.

The cytokine may be IFN$\gamma$ and/or IL-2.

As used herein "increased cytokine production" means that—upon binding of antigen to the TCR—the amount of cytokine produced by a cell which expresses an engineered TCR according to the present invention in greater than the amount produced by an equivalent cell which expresses the corresponding TCR comprising the unmodified germline TCR sequence.

The amount of cytokine produced by a cell which expresses an engineered TCR according to the present invention may be at least 1.5-, 2-, 2.5-, 3-, 4-, 5-, 10-, 20- or 50-fold greater than that produced by an equivalent cell which expresses the corresponding TCR comprising the unmodified germline TCR sequence.

The amount of cytokine produced by a cell may be determined using methods which are known in the art—for example flow cytometry or ELISA.

The present invention also provides a method of producing a cell according to the invention which comprises the step of transfecting or transducing a cell in vitro or ex vivo with a vector according to the invention.

The cell may be isolated from the subject to which the genetically modified cell is to be adoptively transferred. In this respect, the cell may be made by isolating a T-cell from a subject, optionally activating the T-cell, TCR gene transfer ex vivo and subsequent immunotherapy of the subject by adoptive transfer of the TCR-transduced cells.

Alternatively, the cell may be isolated from a different subject, such that it is allogeneic. The cell may be isolated from a donor subject. For example, if the subject is undergoing allogeneic haematopoietic stem cell transplantation (Allo-HSCT), the cell may be derived from the donor, from which the HSCs are derived. If the subject is undergoing or has undergone solid organ transplant, the cell may be derived from the subject from whom the solid organ was derived.

Alternatively, the cell may be, or be derived from, a stem cell, such as a haemopoietic stem cell (HSC). Gene transfer into HSCs does not lead to TCR expression at the cell surface as stem cells do not express the CD3 molecules. However, when stem cells differentiate into lymphoid precursors that migrate to the thymus, the initiation of CD3 expression leads to the surface expression of the introduced TCR in thymocytes.

An advantage of this approach is that the mature T cells, once produced, express only the introduced TCR and little or no endogenous TCR chains, because the expression of the introduced TCR chains suppresses rearrangement of endogenous TCR gene segments to form functional TCR alpha and beta genes.

A further benefit is that the gene-modified stem cells are a continuous source of mature T-cells with the desired antigen specificity. The cell may therefore be a gene-modified stem cell, which, upon differentiation, produces a T-cell expressing a TCR of the first aspect of the invention.

The present invention also provides a method of producing a T-cell expressing a TCR of the invention by inducing the differentiation of a stem cell which comprises a polynucleotide of the invention.

A disadvantage of the stem cell approach is that TCRs with the desired specificity may get deleted during T-cell development in the thymus or may induce tolerance when expressed in peripheral T-cells. Another possible issue is the risk of insertional mutagenesis in stem cells.

Pharmaceutical Composition

The present invention further provides a pharmaceutical composition comprising a TCR, polynucleotide, vector or a cell according to the present invention.

The pharmaceutical composition may additionally comprise a pharmaceutically acceptable carrier, diluent or excipient. The pharmaceutical composition may optionally comprise one or more further pharmaceutically active polypeptides and/or compounds. Such a formulation may, for example, be in a form suitable for intravenous infusion.

Use

The present invention further relates to TCR, polynucleotide, vector, cell or pharmaceutical composition of the present invention for use in treating and/or preventing a disease. In particular, the present invention provides a pharmaceutical composition comprising a cell according to the invention for use in treating and/or preventing a disease.

'Treating' relates to the therapeutic use of the cells of the present invention. Herein the cells may be administered to a subject having an existing disease or condition in order to lessen, reduce or improve at least one symptom associated with the disease and/or to slow down, reduce or block the progression of the disease.

'Preventing' relates to the prophylactic use of the cells of the present invention. Herein such cells may be administered to a subject who has not yet contracted the disease and/or who is not showing any symptoms of the disease to prevent or impair the cause of the disease or to reduce or prevent development of at least one symptom associated with the disease. The subject may have a predisposition for, or be thought to be at risk of developing, the disease.

The present invention also provides the use of an engineered TCR; a nucleic acid sequence or a vector according to the present invention to increase the cell surface expression of the TCR.

The present invention also provides the use of an engineered TCR; a nucleic acid sequence or a vector according to the present invention to increase the functional activity of a cell. The functional activity may be any functional activity as described herein.

Method of Treatment

The present invention provides a method for treating and/or preventing a disease which comprises the step of administering the cells of the present invention (for example in a pharmaceutical composition as described above) to a subject.

The method may involve the steps of:
(i) isolated a cell-containing sample;
(ii) transducing or transfecting such cells with a nucleic acid sequence or vector provided by the present invention;
(iii) administering the cells from (ii) to a subject.

The present invention also provides a cell or a TCR of the present invention for use in treating and/or preventing a disease.

In a preferred embodiment of the present invention, the subject of any of the methods described herein is a mammal, preferably a cat, dog, horse, donkey, sheep, pig, goat, cow, mouse, rat, rabbit or guinea pig, but most preferably the subject is a human.

For administration of cells as described herein, any mode of administration of the cell population which is common or standard in the art may be used, e.g. injection or infusion, by an appropriate route. In one aspect up to $5 \times 10^8$ cells are administered per kg in humans. Thus, for example, a human with a body weight of 100 kg may receive a dose of up to $5 \times 10^{10}$ cells per treatment. The dose can be repeated at later times if necessary.

The invention also relates to the use of a TCR, a vector or a cell according to the present invention in the manufacture of a medicament for treating and/or preventing a disease.

Disease

The disease to be treated and/or prevented by the methods and uses of the present invention may be any disease which induces a T cell mediated immune response.

For example, the disease to be treated and/or prevented by the methods and uses of the present invention may be cancerous disease, such as bladder cancer, breast cancer, colon cancer, endometrial cancer, kidney cancer (renal cell), leukaemia, lung cancer, melanoma, non-Hodgkin lymphoma, pancreatic cancer, prostate cancer and thyroid cancer.

The disease to be treated and/or prevented by the methods and uses of the present invention may be an infection, for example a bacterial or viral infection.

Method

The present invention provides a method for increasing the cell surface expression of a TCR which comprises the steps of:
(i) providing a TCR α chain and/or β chain sequence;
(ii) determining an amino acid residue of the TCR α chain and/or β chain at one or more positions selected from: 96 of the α chain; 9 of the β chain; 10 of the β chain; 24 of the α chain; 19 of the α chain; 20 of the α chain; 50 of the α chain; 5 of the α chain; 8 of the α chain; 86 of the α chain; 39 of the α chain; 55 of the α chain; 43 of the β chain; 66 of the α chain; 19 of the β chain; 21 of the 3 chain; 103 of the β chain; 3 of the α chain; 7 of the α chain; 9 of the α chain; 11 of the α chain; 16 of the α chain; 18 of the α chain; 21 of the α chain; 22 of the α chain; 26 of the α chain; 40 of the α chain; 47 of the α chain; 48 of the α chain; 49 of the α chain; 51 of the α chain; 52 of the α chain; 53 of the α chain; 67 of the α chain; 68 of the α chain; 74 of the α chain; 76 of the α chain; 79 of the α chain; 81 of the α chain; 83 of the α chain; 90 of the α chain; 92 of the α chain; 93 of the α chain; and 101 of the α chain; and
(iii) altering the amino acid residue at one or more of the positions listed in step (ii) to an amino acid residue selected from: an aliphatic, non-polar amino acid or a methionine at position 96 of the α chain; an aliphatic, polar charged amino acid or a glutamine at position 9 of the β chain; an aromatic amino acid at position 10 of the β chain; an aliphatic, polar uncharged amino acid at position 24 of the α chain; an aliphatic, non-polar amino acid or a methionine at position 19 of the α chain; an aliphatic, polar uncharged amino acid at position 20 of the α chain; an aliphatic, polar uncharged amino acid or a isoleucine, leucine or valine at position 50 of the α chain; an aliphatic, polar uncharged amino acid at position 5 of the α chain; an aliphatic, polar uncharged amino acid, a glutamic acid, lysine or arginine at position 8 of the α chain; an aliphatic, polar uncharged amino acid or alanine at position 86 of the α chain; an aromatic amino acid at position 39 of the α chain; an aliphatic, polar charged amino acid or asparagine at position 55 of the α chain; an aliphatic, polar charged amino acid or a glutamine at position 43 of the β chain; an aliphatic, non-polar amino acid or a serine at position 66 of the α chain; an aliphatic, non-polar amino acid or a methionine at position 19 of the β chain; an aliphatic, non-polar amino acid or a methionine at position 21 of the β chain; an aliphatic, non-polar amino acid or a methionine at position 103 of the β chain; an aliphatic, polar uncharged amino acid at position 3 of the α chain; an aliphatic, polar uncharged amino acid or alanine at position 7 of the α chain; an aliphatic, non-polar amino acid at position 9 of the α chain; an aliphatic, non-polar amino acid or a isoleucine, leucine or valine at position 11 of the α chain; an aliphatic, non-polar amino acid or a serine at position 16 of the α chain; an aliphatic, polar uncharged amino acid at position 18 of the α chain; an aliphatic, non-polar amino acid or a methionine at position 21 of the α chain; an aliphatic, polar uncharged amino acid or alanine at position 22 of the α chain; an aliphatic, polar charged amino acid or asparagine at position 26 of the α chain; an aromatic amino acid at position 40 of the α chain; an aliphatic, polar uncharged amino acid or alanine at position 47 of the α chain; an aliphatic, polar charged amino acid or a glutamine at position 48 of the α chain; an aliphatic, polar uncharged amino acid, glutamic acid, lysine or arginine at position 49 of the α chain; an aliphatic, non-polar amino acid or a methionine at position 51 of the α chain; an aliphatic, non-polar amino acid or a methionine at position 52 of the α chain; an aliphatic, non-polar amino acid or a methionine at position 53 of the α chain; an aliphatic, polar uncharged amino acid at position 67 of the α chain; an aliphatic, polar charged amino acid or a glutamine at position 68 of the α chain; an aliphatic, polar uncharged amino acid or an aspartic acid or histidine at position 74 of the α chain; an aromatic amino acid at position 76 of the α chain; an aliphatic, polar uncharged amino acid or an aspartic acid or histidine at position 79 of the α chain; an aliphatic, polar uncharged amino acid, glutamic acid, lysine or arginine at position 81 of the α chain; an aliphatic, non-polar amino acid or a serine at position 83 of the α chain; an aliphatic, polar charged amino acid or a glutamine at position 90 of the α chain; an aliphatic, polar uncharged amino acid or alanine at position 92 of the α chain; an aliphatic, polar charged amino acid or asparagine at position 93 of the α chain; an aliphatic, non-polar amino acid or a isoleucine, leucine or valine at position 101 of the α chain;
with the proviso that when only one amino acid is altered in step (iii) the one altered amino acid does not consist of an amino acid residue specified for the given position selected from group (I):
(I) L96 of the α chain; R9 of the β chain; Y10 of the β chain; T24 of the α chain; V19 of the α chain; T20 of the α chain; M50 of the α chain; T5 of the α chain; Q8 of the α chain; S86 of the α chain; F39 of the α chain; D55 of the α chain; R43 of the β chain; A66 of the α chain; V19 of the β chain; L21 of the β chain; L103 of the β chain; T3 of the α chain; S7 of the α chain; P9 of the α chain; M11 of the α chain; A16 of the α chain; T18 of the α chain; L21 of the α chain; S22 of the α chain; D26 of the α chain; F40 of the α chain; S47 of the α chain; R48 of the α chain; Q49 of the α chain; I51 of the α chain; L52 of the α chain; V53 of the α chain; T67 of the α chain; E68 of the α chain; N74 of the α chain; F76 of the α chain; N79 of the α chain; Q81 of the α chain; A83 of the α chain; K90 of the α chain; S92 of the α chain; D93 of the α chain; and M101 of the α chain; and
when two or more amino acid residues are altered in step (iii) at least one of the altered amino acid residues is not an amino acid residue specified for the given position selected from group (I).

Accordingly, the altered TCR generated in by altering one or more amino acids as defined in step (iii) is an engineered TCR as referred to herein.

As described herein, the germline sequence of each variable gene is known in the art (see Scaviner & Lefranc; as above and Folch & Lefranc; as above) and the Vα and/or Vβ germline V segment utilised in a TCR can therefore by determined by sequencing and comparing to the known germline sequences (see, for example, Hodges et al.; as above, Zhou et al.; 2006; as above). The present step of determining an amino acid residue of the TCR α chain and/or β chain at one or more positions therefore specifically relates to determining the amino acid residue that is present at one or more of the particular positions described herein.

The method may comprise may comprise determining the amino acid residue present at any position or plurality of positions as described herein.

The amino acid sequence of the TCR may be altered such that it comprises any amino acid residue or any plurality of amino acid residues as described herein.

The amino acid sequence of the TCR may be altered such that it comprises one or more amino acid residues as defined above.

The amino acid sequence of a TCR may be altered using methods which are well known in the art. For example, the amino acid sequence of the TCR may be altered mutagenesis of a nucleic acid sequence encoding the TCR.

As detailed above, increasing the cell surface expression of a TCR means that a TCR comprising at least one amino acid residue according to the present invention has a higher level of cell surface expression relative to an equivalent TCR comprising the amino acid sequence encoded by the germline sequence. An equivalent TCR comprising the amino acid sequence encoded by the germline sequence refers to a TCR which has not been altered to comprise an amino acid residue according to the present invention—i.e. the unaltered TCR has the wild-type amino acid residue at the specific position.

Cell surface expression of a TCR may be determined using any of the methods described herein.

The present invention further relates to a method for selecting a TCR which, when expressed in a cell, has a high level of cell surface expression; which method comprises the steps of:
(i) providing one or more TCR α chain and/or β chain sequences; and
(ii) selecting a TCR amino acid sequence comprising one or more amino acid residues selected from:
an aliphatic, non-polar amino acid or a methionine at position 96 of the α chain; an aliphatic, polar charged amino acid or a glutamine at position 9 of the β chain; an aromatic amino acid at position 10 of the β chain; an aliphatic, polar uncharged amino acid at position 24 of the α chain; an aliphatic, non-polar amino acid or a methionine at position 19 of the α chain; an aliphatic, polar uncharged amino acid at position 20 of the α chain; an aliphatic, polar uncharged amino acid or a isoleucine, leucine or valine at position 50 of the α chain; an aliphatic, polar uncharged amino acid at position 5 of the α chain; an aliphatic, polar uncharged amino acid, a glutamic acid, lysine or arginine at position 8 of the α chain; an aliphatic, polar uncharged amino acid or alanine at position 86 of the α chain; an aromatic amino acid at position 39 of the α chain; an aliphatic, polar charged amino acid or asparagine at position 55 of the α chain; an aliphatic, polar charged amino acid or a glutamine at position 43 of the β chain; an aliphatic, non-polar amino acid or a serine at position 66 of the α chain; an aliphatic, non-polar amino acid or a methionine at position 19 of the β chain; an aliphatic, non-polar amino acid or a methionine at position 21 of the β chain; an aliphatic, non-polar amino acid or a methionine at position 103 of the β chain; an aliphatic, polar uncharged amino acid at position 3 of the α chain; an aliphatic, polar uncharged amino acid or alanine at position 7 of the α chain; an aliphatic, non-polar amino acid at position 9 of the α chain; an aliphatic, polar uncharged amino acid or a isoleucine, leucine or valine at position 11 of the α chain; an aliphatic, non-polar amino acid or a serine at position 16 of the α chain; an aliphatic, polar uncharged amino acid at position 18 of the α chain; an aliphatic, non-polar amino acid or a methionine at position 21 of the α chain; an aliphatic, polar uncharged amino acid or alanine at position 22 of the α chain; an aliphatic, polar charged amino acid or asparagine at position 26 of the α chain; an aromatic amino acid at position 40 of the α chain; an aliphatic, polar uncharged amino acid or alanine at position 47 of the α chain; an aliphatic, polar charged amino acid or a glutamine at position 48 of the α chain; an aliphatic, polar uncharged amino acid, glutamic acid, lysine or arginine at position 49 of the α chain; an aliphatic, non-polar amino acid or a methionine at position 51 of the α chain; an aliphatic, non-polar amino acid or a methionine at position 52 of the α chain; an aliphatic, non-polar amino acid or a methionine at position 53 of the α chain; an aliphatic, polar uncharged amino acid at position 67 of the α chain; an aliphatic, polar charged amino acid or a glutamine at position 68 of the α chain; an aliphatic, polar uncharged amino acid or an aspartic acid or histidine at position 74 of the α chain; an aromatic amino acid at position 76 of the α chain; an aliphatic, polar uncharged amino acid or an aspartic acid or histidine at position 79 of the α chain; an aliphatic, polar uncharged amino acid, glutamic acid, lysine or arginine at position 81 of the α chain; an aliphatic, non-polar amino acid or a serine at position 83 of the α chain; an aliphatic, polar charged amino acid or a glutamine at position 90 of the α chain; an aliphatic, polar uncharged amino acid or alanine at position 92 of the α chain; an aliphatic, polar charged amino acid or asparagine at position 93 of the α chain; an aliphatic, polar uncharged amino acid or a isoleucine, leucine or valine at position 101 of the α chain;

wherein a sequence which comprises at least one of the recited amino acid residues is determined to be a high expression TCR and a sequence which does not comprise at least one of the recited amino acid sequences is determined to be a low expression TCR;

with the proviso that when only one amino acid is selected in step (ii) the one amino acid does not consist of an amino acid residue specified for the given position selected from group (I):

(I) L96 of the α chain; R9 of the β chain; Y10 of the β chain; T24 of the α chain; V19 of the α chain; T20 of the α chain; M50 of the α chain; T5 of the α chain; Q8 of the α chain; S86 of the α chain; F39 of the α chain; D55 of the α chain; R43 of the β chain; A66 of the α chain; V19 of the β chain; L21 of the β chain; L103 of the β chain; T3 of the α chain; S7 of the α chain; P9 of the α chain; M11 of the α chain; A16 of the α chain; T18 of the α chain; L21 of the α chain; S22 of the α chain; D26 of the α chain; F40 of the α chain; S47 of the α chain; R48 of the α chain; Q49 of the α chain; I51 of the α chain; L52 of the α chain; V53 of the α chain; T67 of the α chain; E68 of the α chain; N74 of the α chain; F76 of the α chain; N79 of the α chain; Q81 of the α chain; A83 of the α chain; K90 of the α chain; S92 of the α chain; D93 of the α chain; and M101 of the α chain; and when two or more amino acid residues are selected in step (ii) at least one of the amino acid residues selected is not an amino acid residue specified for the given position selected from group (I).

The method may comprise the step of selecting a TCR which comprises one or more amino acid residues as defined herein.

In a further aspect the present invention provides a method for determining the strength of a TCR which comprises the steps of:

(i) providing a TCR α chain and/or β chain sequence; and (ii) determining if the TCR sequence comprises one or more amino acid residues selected from:

an aliphatic, non-polar amino acid or a methionine at position 96 of the α chain; an aliphatic, polar charged amino acid or a glutamine at position 9 of the β chain; an aromatic amino acid at position 10 of the β chain; an aliphatic, polar uncharged amino acid at position 24 of the α chain; an aliphatic, non-polar amino acid or a methionine at position 19 of the α chain; an aliphatic, polar uncharged amino acid at position 20 of the α chain; an aliphatic, polar uncharged amino acid or a isoleucine, leucine or valine at position 50 of the α chain; an aliphatic, polar uncharged amino acid at position 5 of the α chain; an aliphatic, polar uncharged amino acid, a glutamic acid, lysine or arginine at position 8 of the α chain; an aliphatic, polar uncharged amino acid or alanine at position 86 of the α chain; an aromatic amino acid at position 39 of the α chain; an aliphatic, polar charged amino acid or asparagine at position 55 of the α chain; an aliphatic, polar charged amino acid or a glutamine at position 43 of the β chain; an aliphatic, non-polar amino acid or a serine at position 66 of the α chain; an aliphatic, non-polar amino acid or a methionine at position 19 of the β chain; an aliphatic, non-polar amino acid or a methionine at position 21 of the β chain; an aliphatic, non-polar amino acid or a methionine at position 103 of the β chain; an aliphatic, polar uncharged amino acid at position 3 of the α chain; an aliphatic, polar uncharged amino acid or alanine at position 7 of the α chain; an aliphatic, non-polar amino acid at position 9 of the α chain; an aliphatic, polar uncharged amino acid or a isoleucine, leucine or valine at position 11 of the α chain; an aliphatic, non-polar amino acid or a serine at position 16 of the α chain; an aliphatic, polar uncharged amino acid at position 18 of the α chain; an aliphatic, non-polar amino acid or a methionine at position 21 of the α chain; an aliphatic, polar uncharged amino acid or alanine at position 22 of the α chain; an aliphatic, polar charged amino acid or asparagine at position 26 of the α chain; an aromatic amino acid at position 40 of the α chain; an aliphatic, polar uncharged amino acid or alanine at position 47 of the α chain; an aliphatic, polar charged amino acid or a glutamine at position 48 of the α chain; an aliphatic, polar uncharged amino acid, glutamic acid, lysine or arginine at position 49 of the α chain; an aliphatic, non-polar amino acid or a methionine at position 51 of the α chain; an aliphatic, non-polar amino acid or a methionine at position 52 of the α chain; an aliphatic, non-polar amino acid or a methionine at position 53 of the α chain; an aliphatic, polar uncharged amino acid at position 67 of the α chain; an aliphatic, polar charged amino acid or a glutamine at position 68 of the α chain; an aliphatic, polar uncharged amino acid or an aspartic acid or histidine at position 74 of the α chain; an aromatic amino acid at position 76 of the α chain; an aliphatic, polar uncharged amino acid or an aspartic acid or histidine at position 79 of the α chain; an aliphatic, polar uncharged amino acid, glutamic acid, lysine or arginine at position 81 of the α chain; an aliphatic, non-polar amino acid or a serine at position 83 of the α chain; an aliphatic, polar charged amino acid or a glutamine at position 90 of the α chain; an aliphatic, polar uncharged amino acid or alanine at position 92 of the α chain; an aliphatic, polar charged amino acid or asparagine at position 93 of the α chain; an aliphatic, polar uncharged amino acid or a isoleucine, leucine or valine at position 101 of the α chain;

with the proviso that when only one amino acid is selected in step (ii) the one amino acid does not consist of an amino acid residue specified for the given position selected from group (I):

(I) L96 of the α chain; R9 of the β chain; Y10 of the β chain; T24 of the α chain; V19 of the α chain; T20 of the α chain; M50 of the α chain; T5 of the α chain; Q8 of the α chain; S86 of the α chain; F39 of the α chain; D55 of the α chain; R43 of the β chain; A66 of the α chain; V19 of the β chain; L21 of the β chain; L103 of the β chain; T3 of the α chain; S7 of the α chain; P9 of the α chain; M11 of the α chain; A16 of the α chain; T18 of the α chain; L21 of the α chain; S22 of the α chain; D26 of the α chain; F40 of the α chain; S47 of the α chain; R48 of the α chain; Q49 of the α chain; I51 of the α chain; L52 of the α chain; V53 of the α chain; T67 of the α chain; E68 of the α chain; N74 of the α chain; F76 of the α chain; N79 of the α chain; Q81 of the α chain; A83 of the α chain; K90 of the α chain; S92 of the α chain; D93 of the α chain; and M101 of the α chain; and when two or more amino acid residues are selected in step (ii) at least one of the amino acid residues selected is not an amino acid residue specified for the given position selected from group (I).

The α chain and/or β chain sequence may be an amino acid sequence or a polynucleotide sequence which encodes an α chain and/or a β chain.

The method may comprise may comprise determining the amino acid residue present at one or more positions as described herein.

Such a method is useful for predicting the level of surface expression of a TCR, for example a therapeutic TCR, when it is expressed as an exogenous TCR in a cell, for example a T cell.

The present invention further relates to a method for identifying amino acid residues which influence the cell surface expression level of an exogenous TCR, which comprises the steps of:
(i) comparing the cell surface expression levels of a plurality of TCRs with a reference TCR;
(ii) determining TCRs from the plurality of TCRs which have (a) a low level of cell surface expression compared to the reference TCR or (b) a similar or high level of cell surface expression compared to the reference TCR;
(iii) comparing the amino acid sequences between TCRs selected in group (a) and group (b) in step (ii) to identify amino acid residues which influence to the cell surface expression level of the TCR when it is expressed in a cell.

Suitably, the method is used to identify amino acid residues which are associated with a high level of cell surface expression of an exogenous TCR. Herein, amino acid residues which are predominantly present in TCRs selected in group (b) in step (ii) may be determined to be associated with high cell surface expression of an exogenous TCR.

Suitably, the method is used to identify amino acid residues which are associated with a low level of cell surface expression of an exogenous TCR. Herein, amino acid residues which are predominantly present in TCRs selected in Group (a) in step (ii) may be determined to be associated with low cell surface expression of an exogenous TCR.

Amino acid sequences of TCRs may be determined using methods which are known in the art, for example using clonotyping methods such as those described in Hodges et al. and Zhou et al. (both as above) and as exemplified in present Example 2.

The cell surface expression of TCRs may be compared using methods which are known in the art—such as those described herein. For example, the cell surface expression of a TCR may be determined using flow cytometry. In particular, the cell surface expression of a TCR may be determined using flow cytometry with a detectable antibody which specifically binds to the reference TCR and/or the endogenous TCR.

The plurality of TCRs may be a plurality of endogenous TCRs expressed in a population of cells. The cells may be, for example, CD4+ or CD8+ T cells or NKT cells. The cells may be mammalian cells, preferably human cells expressing endogenous human TCRs.

The reference TCR may be co-expressed as an exogenous TCR in a population of cells which comprise the plurality of TCRs.

A TCR from the plurality of TCRs which has a low level of cell surface expression compared to the reference TCR may not be detectable on the cell surface when the reference TCR is co-expressed in same cell.

A TCR from the plurality of TCRs which has similar or high level of cell surface expression compared to the reference TCR may be detectable on the cell surface when the reference TCR is co-expressed in same cell.

The reference TCR has a structure which enables the cell surface expression of the reference TCR to be distinguished from the cell surface expression of the plurality of TCRs. For example, the reference TCR may comprise different amino acids, domains and/or motifs which enable cell surface expression of the reference TCR to be distinguished from cell surface expression of one or more of the plurality of TCRs. For example, the reference TCR may comprise different amino acids, domains and/or motifs which are detectable using a different antibody during flow cytometry. For example the reference TCR may contain tags such as Myc and/or V5 that are recognised by antibodies against these tags (e.g. see FIG. 4). Suitably, the reference TCR may comprise a different constant domain to the plurality of TCRs. For example, if the plurality of TCRs comprise a human constant domain, the reference TCR may comprise a non-human constant domain—for example a murine or rabbit constant domain. The murine constant domain may be a murinised constant domain.

The reference TCR may be specific for any antigen or the reference TCR may have an unknown specificity. Suitably, the reference TCR may not be a TCR specific for WT1 (Wilms tumour 1). Suitably, a WT1 TCR is a TCR which specifically binds to a peptide antigen from WT1 protein.

In one embodiment, the method does not identify L96 of the α chain; R9 of the β chain; Y10 of the β chain; T24 of the α chain; V19 of the α chain; T20 of the α chain; M50 of the α chain; T5 of the α chain; Q8 of the α chain; S86 of the α chain; F39 of the α chain; D55 of the α chain; R43 of the β chain; A66 of the α chain; V19 of the β chain; L21 of the β chain; L103 of the β chain; T3 of the α chain; S7 of the α chain; P9 of the α chain; M11 of the α chain; A16 of the α chain; T18 of the α chain; L21 of the α chain; S22 of the α chain; D26 of the α chain; F40 of the α chain; S47 of the α chain; R48 of the α chain; Q49 of the α chain; I51 of the α chain; L52 of the α chain; V53 of the α chain; T67 of the α chain; E68 of the α chain; N74 of the α chain; F76 of the α chain; N79 of the α chain; Q81 of the α chain; A83 of the α chain; K90 of the α chain; S92 of the α chain; D93 of the α chain; and M101 of the α chain as amino acid residues with increase cell surface expression of the TCR.

The present invention also relates to a method for increasing dimerization of TCR α and β chains which comprises the steps of:
(i) providing a TCR α chain and/or β chain sequence;
(ii) determining an amino acid residue of the TCR α chain and/or β chain at one or more positions selected from: 96 of the α chain; 9 of the β chain; 10 of the β chain; 24 of the α chain; 19 of the α chain; 20 of the α chain; 50 of the α chain; 5 of the α chain; 8 of the α chain; 86 of the α chain; 39 of the α chain; 55 of the α chain; 43 of the β chain; 66 of the α chain; 19 of the β chain; 21 of the 3 chain; 103 of the β chain; 3 of the α chain; 7 of the α chain; 9 of the α chain; 11 of the α chain; 16 of the α chain; 18 of the α chain; 21 of the α chain; 22 of the α chain; 26 of the α chain; 40 of the α chain; 47 of the α chain; 48 of the α chain; 49 of the α chain; 51 of the α chain; 52 of the α chain; 53 of the α chain; 67 of the α chain; 68 of the α chain; 74 of the α chain; 76 of the α chain; 79 of the α chain; 81 of the α chain; 83 of the α chain; 90 of the α chain; 92 of the α chain; 93 of the α chain; and 101 of the α chain; and
(iii) altering the amino acid residue at one or more of the positions listed in step (ii) to an amino acid residue selected from: an aliphatic, non-polar amino acid or a methionine at position 96 of the α chain; an aliphatic, polar charged amino acid or a glutamine at position 9 of the β chain; an aromatic amino acid at position 10 of the β chain; an aliphatic, polar uncharged amino acid at position 24 of the α chain; an aliphatic, non-polar amino acid or a methionine at position 19 of the α chain; an aliphatic, polar uncharged amino acid at position 20 of the α chain; an aliphatic, polar uncharged amino acid or a isoleucine, leucine or valine at position 50 of the α chain; an aliphatic, polar uncharged amino acid at position 5 of the α chain; an aliphatic, polar uncharged amino acid, a glutamic acid, lysine or arginine at position 8 of the α chain; an aliphatic, polar uncharged amino acid or alanine at position 86 of the α chain; an aromatic amino acid at position 39 of the α chain; an aliphatic, polar charged amino acid or asparagine at position 55 of the α chain; an aliphatic, polar charged amino acid or a glutamine at position 43 of the β chain; an aliphatic, non-polar amino acid or a serine at position 66 of the α chain; an aliphatic, non-polar amino acid or a methionine at position 19 of the β chain; an aliphatic, non-polar amino acid or a methionine at position 21 of the β chain; an aliphatic, non-polar amino acid or a methionine at position 103 of the β chain; an aliphatic, polar uncharged amino acid at position 3 of the α chain; an aliphatic, polar uncharged amino acid or alanine at position 7 of the α chain; an aliphatic, non-polar amino acid at position 9 of the α chain; an aliphatic, non-polar amino acid or a isoleucine, leucine or valine at position 11 of the α chain; an aliphatic, non-polar amino acid or a serine at position 16 of the α chain; an aliphatic, polar uncharged amino acid at position 18 of the α chain; an aliphatic, non-polar amino acid or a methionine at position 21 of the α chain; an aliphatic, polar uncharged amino acid or alanine at position 22 of the α chain; an aliphatic, polar charged amino acid or asparagine at position 26 of the α chain; an aromatic amino acid at position 40 of the α chain; an aliphatic, polar uncharged amino acid or alanine at position 47 of the α chain; an aliphatic, polar charged amino acid or a glutamine at position 48 of the α chain; an aliphatic, polar uncharged amino acid, glutamic acid, lysine or arginine at position 49 of the α chain; an aliphatic, non-polar amino acid or a methionine at position 51 of the α chain; an aliphatic, non-polar amino acid or a methionine at position 52 of the α chain; an aliphatic, non-polar amino acid or a methionine at position 53 of the α chain; an aliphatic, polar uncharged amino acid at position 67 of the α chain; an aliphatic, polar charged amino acid or a glutamine at position 68 of the α chain; an aliphatic, polar uncharged amino acid or an aspartic acid or histidine at position 74 of the α chain; an aromatic amino acid at position 76 of the α chain; an aliphatic, polar uncharged amino acid or an aspartic acid or histidine at position 79 of the α chain; an aliphatic, polar uncharged amino acid, glutamic acid, lysine or arginine at position 81 of the α chain; an aliphatic, non-polar amino acid or a serine at position 83 of the α chain; an aliphatic, polar charged amino acid or a glutamine at position 90 of the α chain; an aliphatic, polar uncharged amino acid or alanine at position 92 of the α chain; an aliphatic, polar charged amino acid or asparagine at position 93 of the α chain; an aliphatic, non-polar amino acid or a isoleucine, leucine or valine at position 101 of the α chain.

In some embodiments, the TCR α and β chains to be altered by said method for increasing dimerization of TCR α and β chains are of a soluble TCR (sTCR). sTCR typically comprise the TCR variable domains and at least part of the constant domain but lack the transmembrane domain and intracellular, cytoplasmic domain. Suitably, the sTCR of the present method comprises (i) all or part of a TCR α chain, except the transmembrane domain thereof, and (ii) all or part of a TCR β chain, except the transmembrane domain therefore, wherein (i) and (ii) each comprise a functional variable domain and at least a part of the constant domain of the TCR. In one aspect, a sTCR of the present method does not comprise a transmembrane domain. Thus, the sTCR is not anchored on the surface of cell. Suitably, the sTCR α chain and β chain may comprise all of the extracellular constant Ig domain of the TCR chain. Suitably, the sTCR α chain and β chain may comprise all of the extracellular domain of the TCR chain.

In some embodiments, the TCR α and β chains to be altered by said method for increasing dimerization of TCR α and β chains are of a membrane bound TCR and the method comprises the proviso that when only one amino acid is altered in step (iii) the one altered amino acid does not consist of an amino acid residue specified for the given position selected from group (I):

(I) L96 of the α chain; R9 of the β chain; Y10β of the β chain; T24 of the α chain; V19 of the α chain; T20 of the α chain; M50 of the α chain; T5 of the α chain; Q8 of the α chain; S86 of the α chain; F39 of the α chain; D55 of the α chain; R43 of the β chain; A66 of the α chain; V19 of the β chain; L21 of the β chain; L103 of the β chain; T3 of the α chain; S7 of the α chain; P9 of the α chain; M11 of the α chain; A16 of the α chain; T18 of the α chain; L21 of the α chain; S22 of the α chain; D26 of the α chain; F40 of the α chain; S47 of the α chain; R48 of the α chain; Q49 of the α chain; I51 of the α chain; L52 of the α chain; V53 of the α chain; T67 of the α chain; E68 of the α chain; N74 of the α chain; F76 of the α chain; N79 of the α chain; Q81 of the α chain; A83 of the α chain; K90 of the α chain; S92 of the α chain; D93 of the α chain; and M101 of the α chain; and when two or more amino acid residues are altered in step (iii) at least one of the altered amino acid residues is not an amino acid residue specified for the given position selected from group (I).

Also provided is a TCR or a sTCR according to the method for increasing dimerization of TCR α and β chains described above.

Such method may improve expression yield of the TCR on the cell surface or of the sTCR being excreted as soluble protein by the cell.

Computer Programme Product

Figure 12:
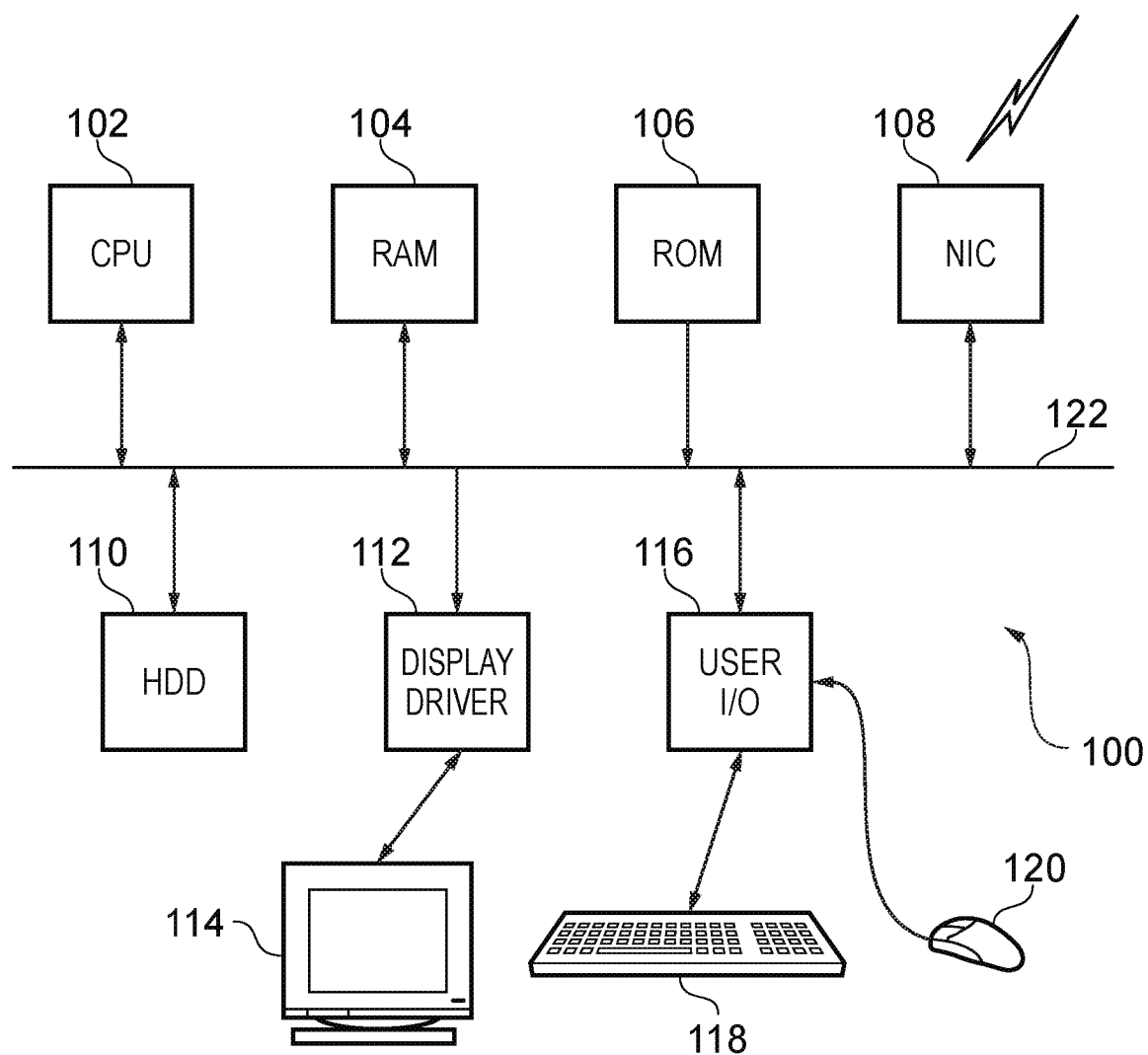
FIG. 12—A general purpose computing device which is used to provide or support some embodiments.
Figure 13:
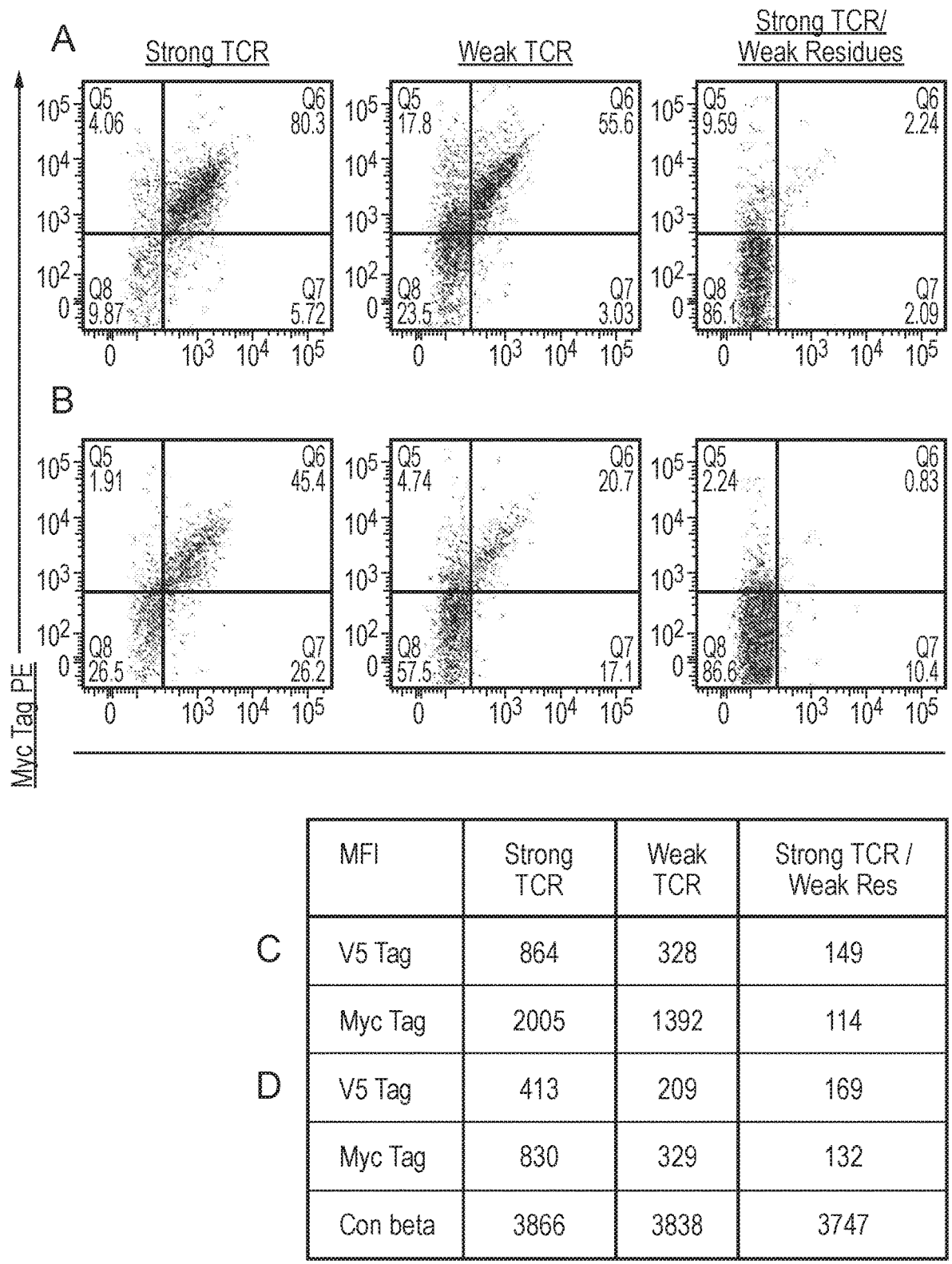
FIG. 13—Jurkat cells without TCR (A) and Jurkat cells expressing the modified WT1 TCR (B) where transduced with the pMP71 retrovirus encoding the indicated TCRs. 72 h after transduction, cells were stained with anti-CD19, V5 Tag, Myc Tag and murine constant beta TCR antibodies. Cells were gated on high CD19 expression and the V5 Tag, Myc Tag and murine constant beta TCR expression was determined. The MFI of V5 Tag, Myc Tag and murine constant beta TCR expression were also determined for the CD19+ high expressing cells. (C) MFI of V5 Tag and Myc Tag for Jurkat cells without TCR. (D) MFI of V5 Tag, Myc Tag and murine constant beta TCR for Jurkat cells expressing the modified WT1 TCR.
Figure 13:
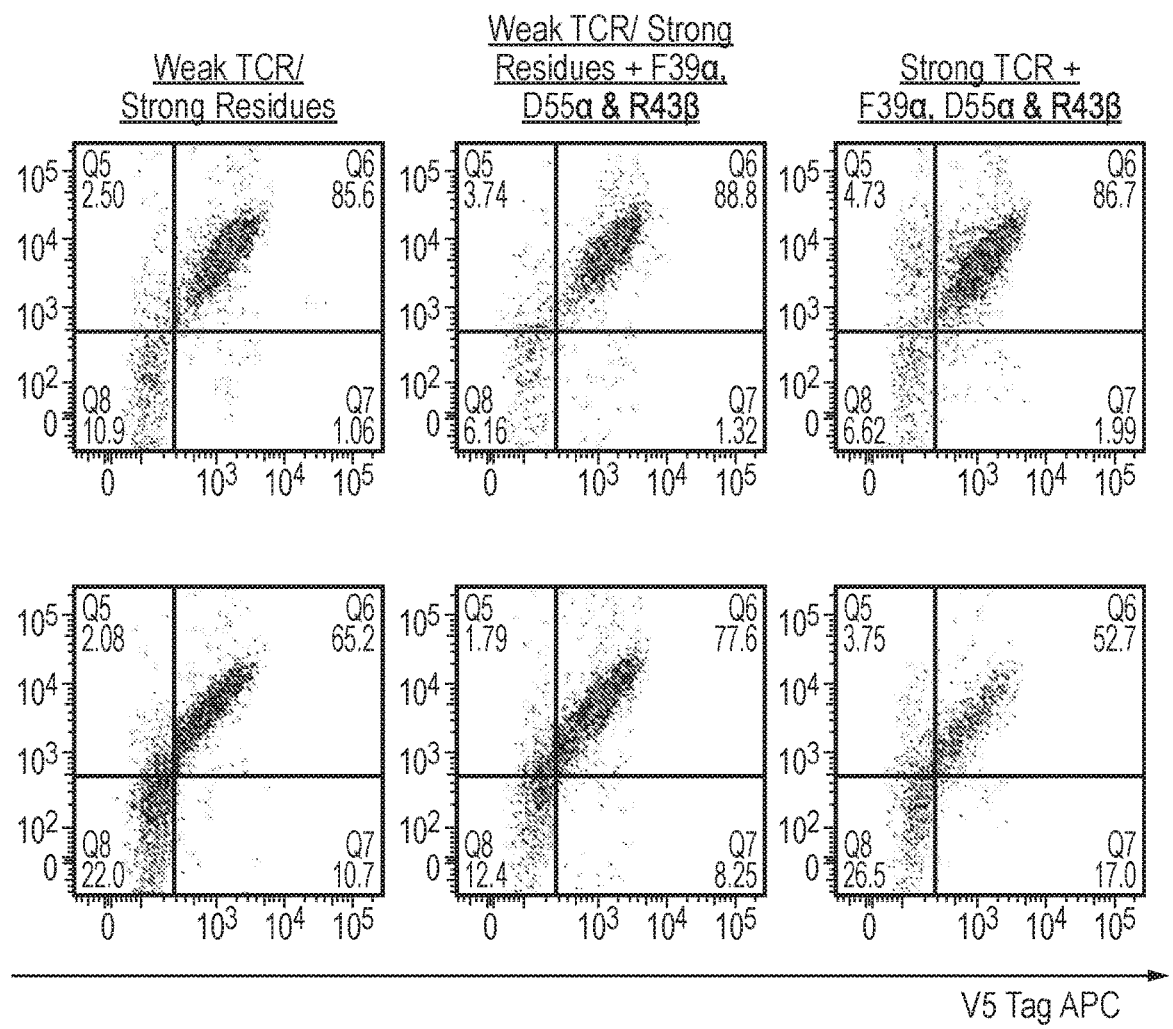

FIG. 12 schematically illustrates a general purpose computing device 100 of the type that may be used to implement the above described techniques. In the context of the present invention this could for example be an embedded processor forming part of a larger system. The general purpose computing device 100 includes a central processing unit 102, a random access memory 104 and a read only memory 106, connected together via bus 122. It also further comprises a network interface card 108, a hard disk drive 110, a display driver 112 and monitor 114 and a user input/output circuit 116 with a keyboard 118 and mouse 120 all connected via the common bus 122. In operation, such as when forming part of a larger system the central processing unit 102 will execute computer program instructions that may for example be stored in the random access memory 104 and/or the read only memory 106. Program instructions could be additionally retrieved from the hard disk drive 110 or dynamically downloaded via the network interface card 108. The results of the processing performed may be displayed to a user or an engineer via a connected display driver 112 and monitor 114. User inputs for controlling the operation of the general purpose computing device 100 may be received via a connected user input output circuit 116 from the keyboard 118 or the mouse 120. It will be appreciated that the computer program could be written in a variety of different computer languages. The computer program may be stored locally on a recording medium or dynamically downloaded to the general purpose computing device 100. When operating under control of an appropriate computer program, the general purpose computing device 100 can perform the above described techniques and can be considered to form an apparatus for performing any of the above described techniques. The architecture of the general purpose computing device 100 could vary considerably and FIG. 13 is only one example. The general purpose computing device 100 can also have a configuration which allows it to provide an instruction execution environment (i.e. a virtual machine).

This disclosure is not limited by the exemplary methods and materials disclosed herein, and any methods and materials similar or equivalent to those described herein can be used in the practice or testing of embodiments of this disclosure. Numeric ranges are inclusive of the numbers defining the range. Unless otherwise indicated, any nucleic acid sequences are written left to right in 5' to 3' orientation; amino acid sequences are written left to right in amino to carboxy orientation, respectively.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within this disclosure. The upper and lower limits of these smaller ranges may independently be included or excluded in the range, and each range where either, neither or both limits are included in the smaller ranges is also encompassed within this disclosure, subject to any specifically excluded limit in the stated range. Where the stated range includes one or both of the limits, ranges excluding either or both of those included limits are also included in this disclosure.

It must be noted that as used herein and in the appended claims, the singular forms "a", "an", and "the" include plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" also include the term "consisting of".

The publications discussed herein are provided solely for their disclosure prior to the filing date of the present application. Nothing herein is to be construed as an admission that such publications constitute prior art to the claims appended hereto.

The invention will now be further described by way of Examples, which are meant to serve to assist one of ordinary skill in the art in carrying out the invention and are not intended in any way to limit the scope of the invention.

EXAMPLES

Example 1—Determination of TCR Variable Segments which Correlate with Strong or Weak TCR Expression Following T cell transduction with TCRs, the introduced TCRs differ greatly in their ability to be expressed on the cell surface relatively to endogenous TCRs. Strongly expressed exogenous TCRs are co-expressed with the endogenous TCR or can even out-compete the endogenous TCR for cell surface expression. Weakly expressed exogenous TCRs are absent from the cell surface or are poorly expressed when co-expressed with a strong TCR (FIG. 1A).

Activated primary T cells were transduced with a pMP71 vector encoding WT1 (Wilms tumour 1) TCR, containing a murinised constant domain and an additional cysteine in the constant domain (the whole TCR was codon optimised).

Figure 2:
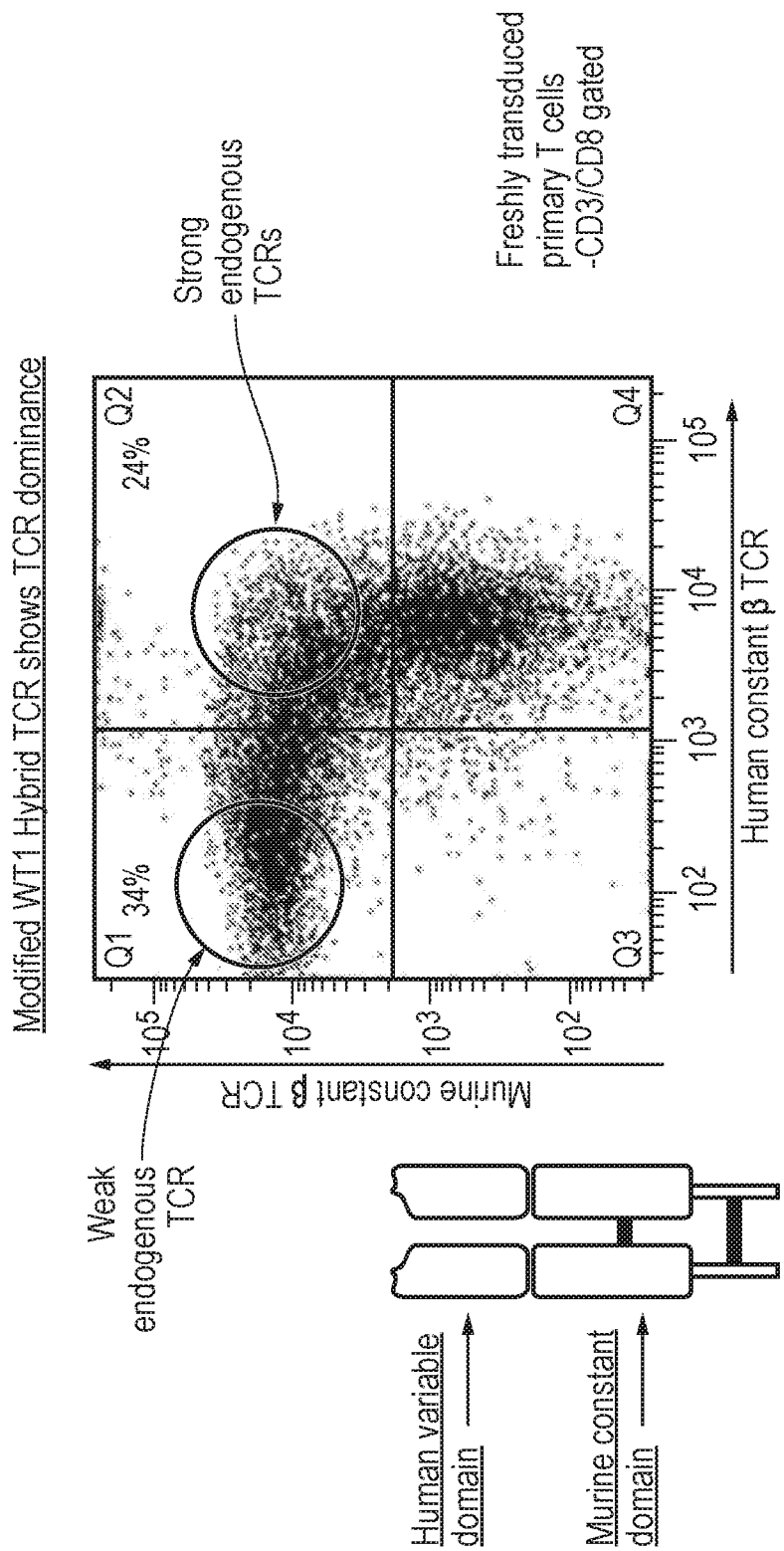
FIG. 2—Primary T cells transduced with a modified WT1 TCR that shows TCR dominance.

This modified WT1 TCR shows TCR dominance (FIG. 2). 72 hours after transduction the T cells were stained with anti-CD3 and CD8 antibodies and anti-human TCR constant domain and anti-murine TCR constant domain antibodies. T cells were gated on the CD3+ and CD8+ T cell population. CD8+ T cells expressing strong endogenous TCRs are co-stained with the anti-murine and anti-human TCR constant domain antibodies. CD8+ T cells expressing weak endogenous TCRs are stained only with the anti-murine TCR constant domain antibodies.

Figures 1, 25:
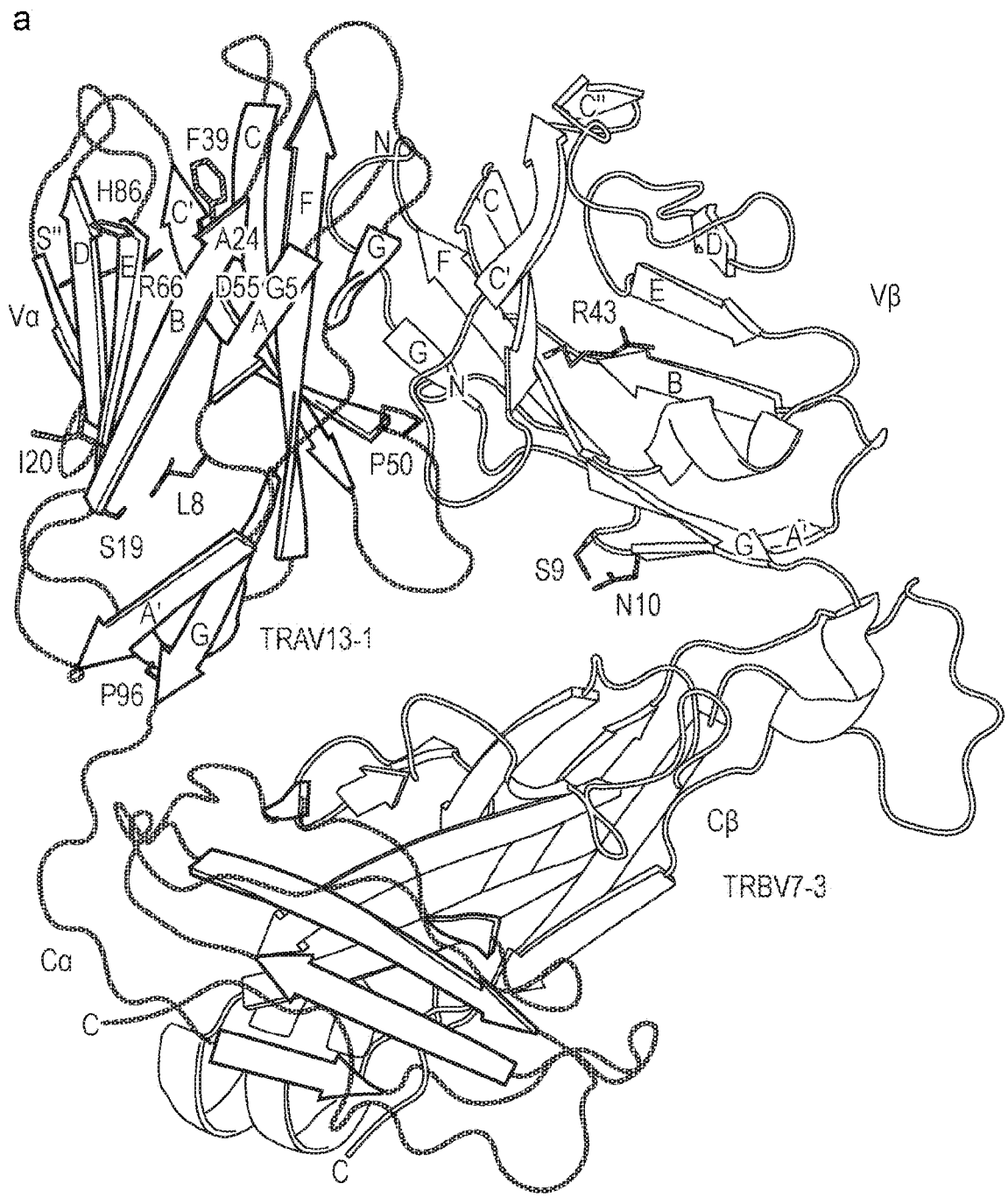
FIG. 25—Structural modelling provides insight into the mechanistic role of framework residues in TCR stability. The published 3-D structure of the 3PL6 TCR (TRAV13-1/TRBV7-3) was used as model for the low expression TCR (TRAV13-474 2/TRBV7-3) used in this study. (a) The location of the 14 residues that were changed in the low expression TCR to enhance TCR surface expression is indicated. (b) The change of P96α to L96α improves the interaction between the variable and the constant domain of the α chain. (c) The change of S9 and N10β to R9β and Y10β improves the interaction between the variable and the constant domain of the β chain. (d) The change of S19α to V19α improves hydrophobic interactions within a hydrophobic core of the α chain. (e) Replacement of A24α with T24α can improve hydrogen bonding interactions with the imidazole ring nitrogen of H86α.
Figures 2, 25:
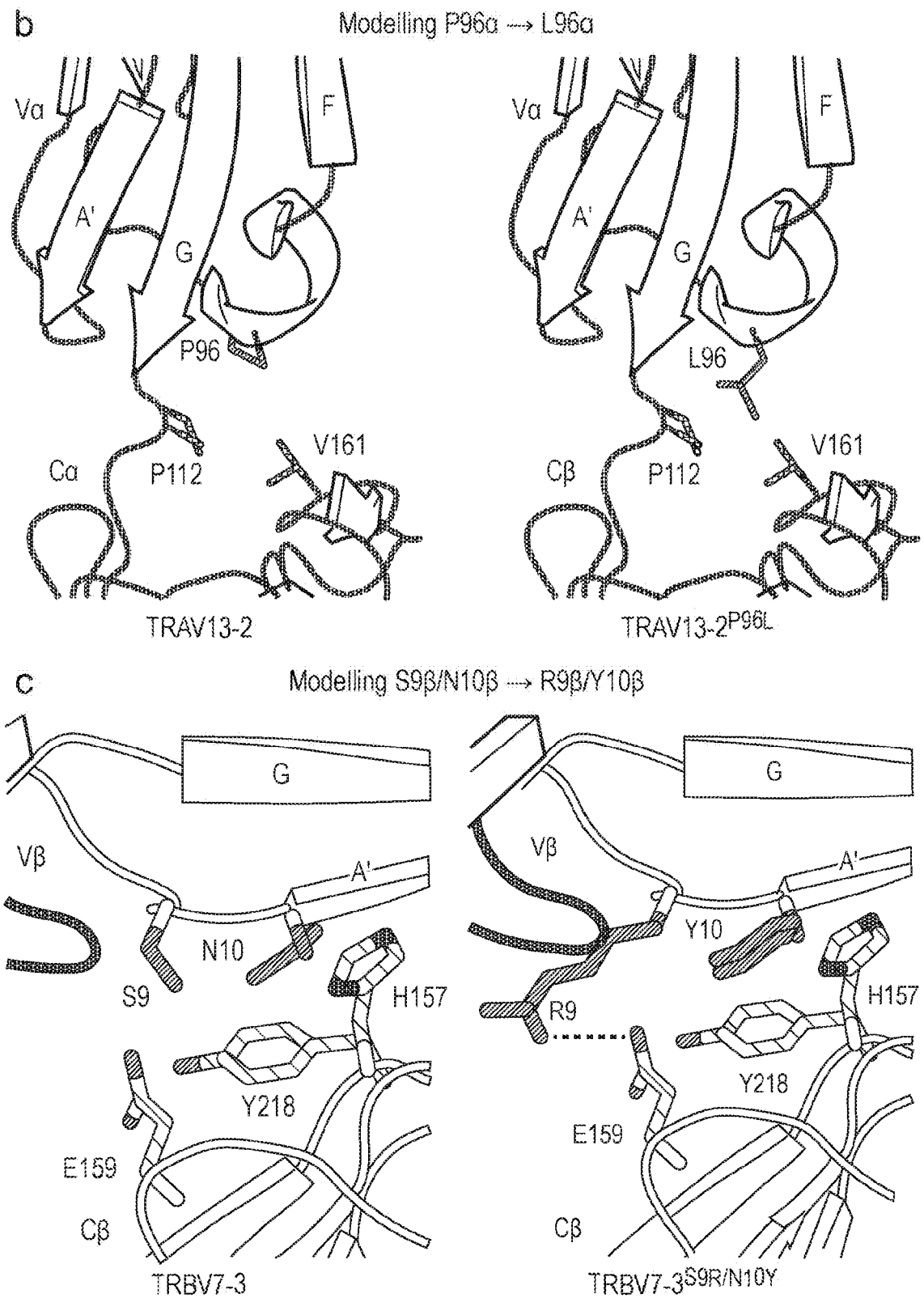
Figures 3, 25:
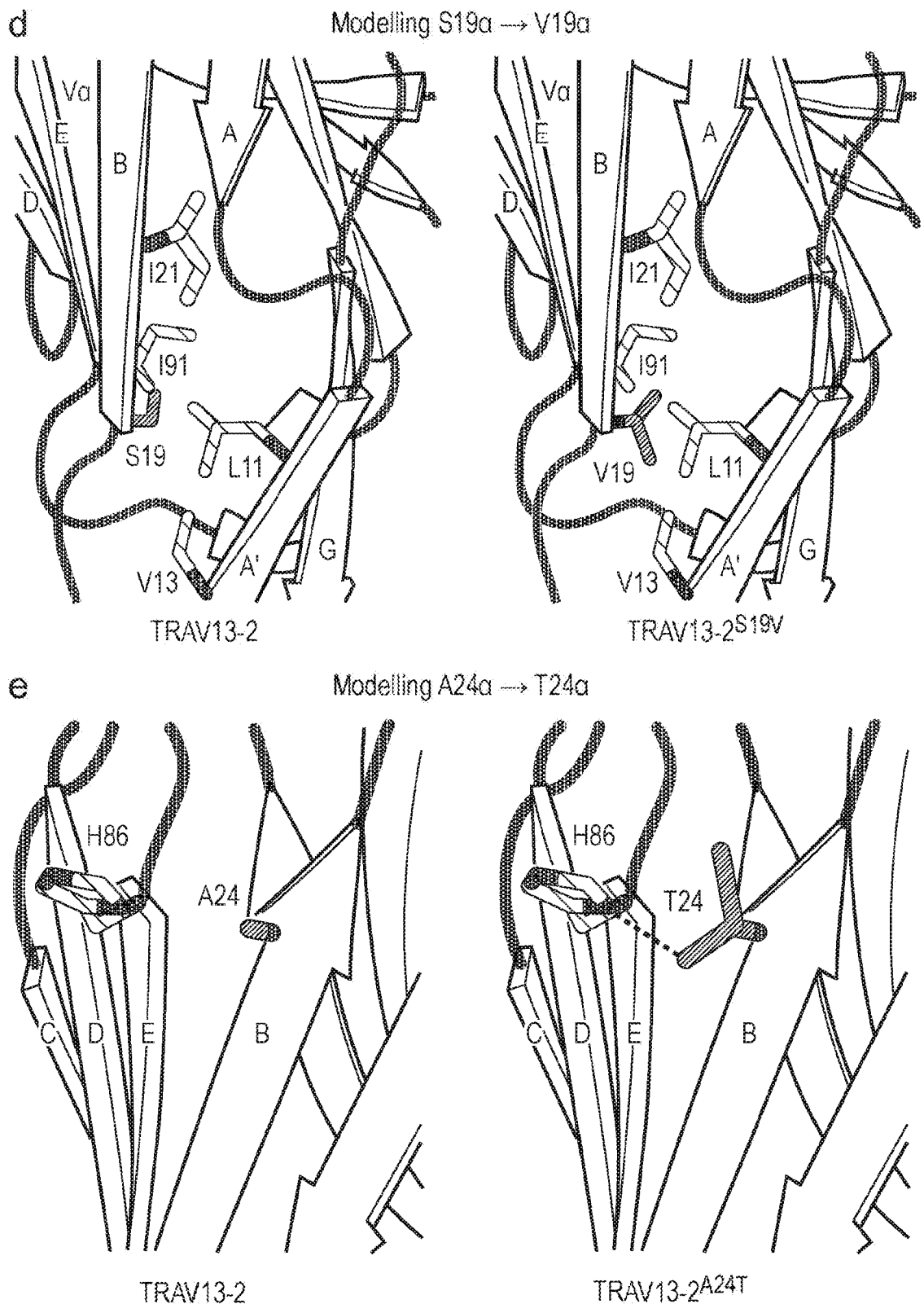
FIG. 3—TCR clonotyping of strong and weak endogenous TCR
Displayed in the table is (i) the total number of strong and weak alpha and beta variable segments that were sequenced and (ii) the alpha variable segments and beta variable segments that show dominance in either the strong or weak endogenous TCR population, alongside the total number of each of the variable segments within each population. The alpha and beta segments have been classified using the IMGT nomenclature.

The CD8+ T cell populations expressing the strong and weak endogenous TCRs were FACs sorted and clonotyped to determine their variable alpha and beta chain usage. Displayed in the table shown in FIG. 3 is (i) the total number of strong and weak alpha and beta variable segments that were sequenced and (ii) the alpha variable segments and beta variable segments that show dominance in either the strong or weak endogenous TCR population, alongside the total number of each of the variable segments within each population. The alpha and beta segments have been classified using the IMGT nomenclature.

Example 2—Expression of Generic Strong and Weak TCRs in Non-Competitive and Competitive Environments The clonotying data was used to determine the alpha and beta variable segments most prevalently used in the strong and weak TCR populations. Generic strong and weak TCR were engineered using this information.

Figure 4:
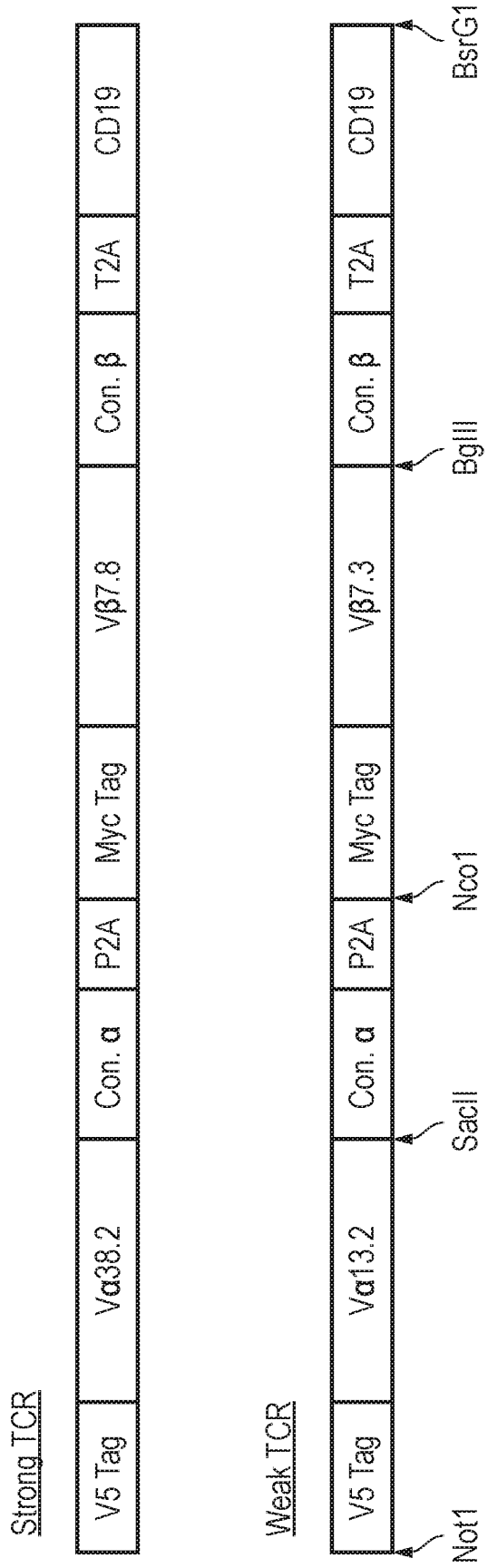
FIG. 4—Illustration of constructs used to assess the characteristics of generic strong and weak expression TCRs.

The strong TCR is variable alpha 38.2 and variable beta 7.8. The weak TCR is variable alpha 13.2 and variable beta 7.3. As monoclonal antibodies are not commercial available to the above alpha and beta variable segments, in order to determine TCR expression in transduced T cells a V5 Tag is present at the start of the alpha chain and a Myc Tag is present at the start of the beta chain. In addition, in order to be able to normalize transduction efficiency a truncated murine CD19 is present at the end of the constructs (FIG. 4).

The two constructs contained the same alpha and beta constant domains and the whole construct was non-codon optimized. Furthermore, unique restrictions sites border the alpha and beta segments in order to allow easy swapping of the alpha and beta segments. The TCRs are cloned into the pMP71 retrovirus for transduction experiments.

Expression of Strong and Weak TCRs in a Non-Competitive Environment

Figure 5:
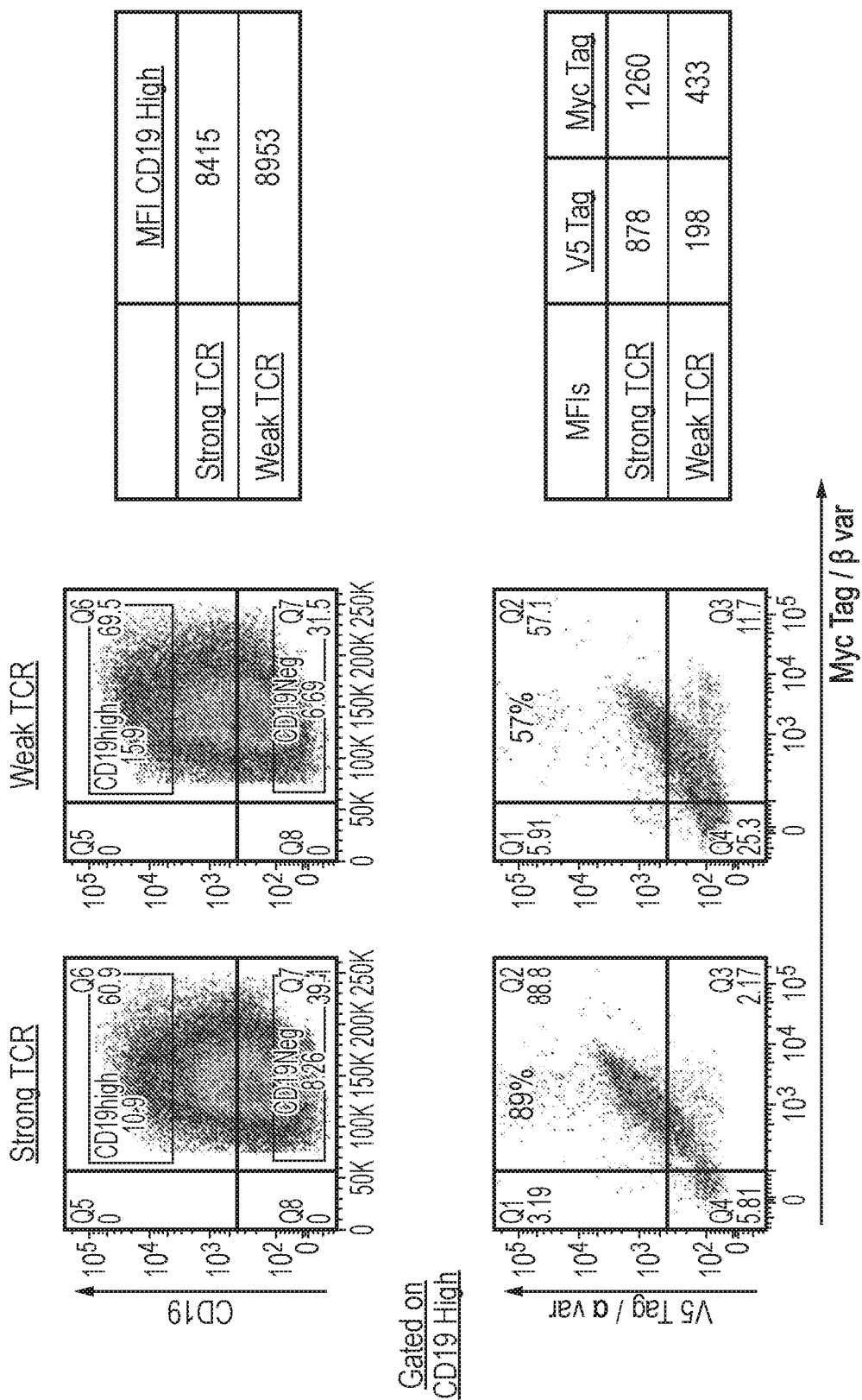
FIG. 5—Expression of strong and weak TCRs in a non-competitive environment (Jurkat cells without TCR).

Jurkat cells that do not contain endogenous TCR alpha or beta chains were transduced with pMP71 vectors encoding the generic strong or weak TCRs. 72 hours after transduction, the Jurkat cells were stained with anti-CD19, V5 Tag and Myc Tag antibodies (FIG. 5). Jurkat cells were gated on high CD19 expression and the V5 Tag and Myc Tag expression on these CD19+ high expressing cells was determined. In addition, the MFI of V5 Tag and Myc Tag were also determined for the CD19+ high expressing cells.

Expression of Strong and Weak TCRs in a Competitive Environment

Figure 6:
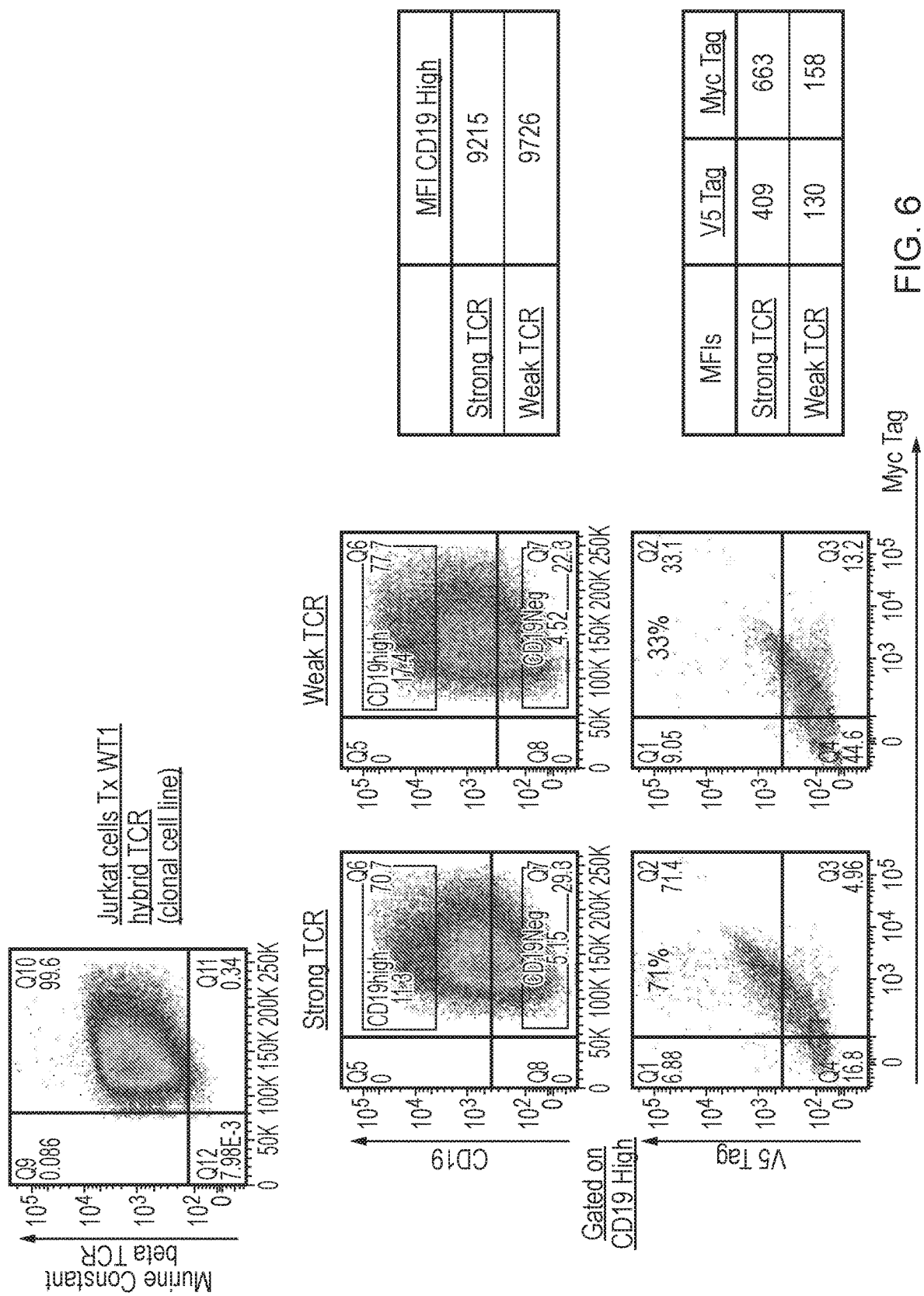
FIG. 6—Expression of strong and weak TCRs in a competitive environment (Jurkat cells expressing the WT1 hybrid TCR).

Jurkat cells expressing the modified WT1 TCR were transduced with pMP71 vectors encoding the generic strong or weak TCRs. 72 hours after transduction, Jurkat cells were stained with anti-CD19, V5 Tag and Myc Tag antibodies (FIG. 6). Jurkat cells were gated on high CD19 expression and the V5 Tag and Myc Tag expression was determined. The MFI of V5 Tag and Myc Tag were also determined for the CD19+ high expressing cells.

Figure 7:
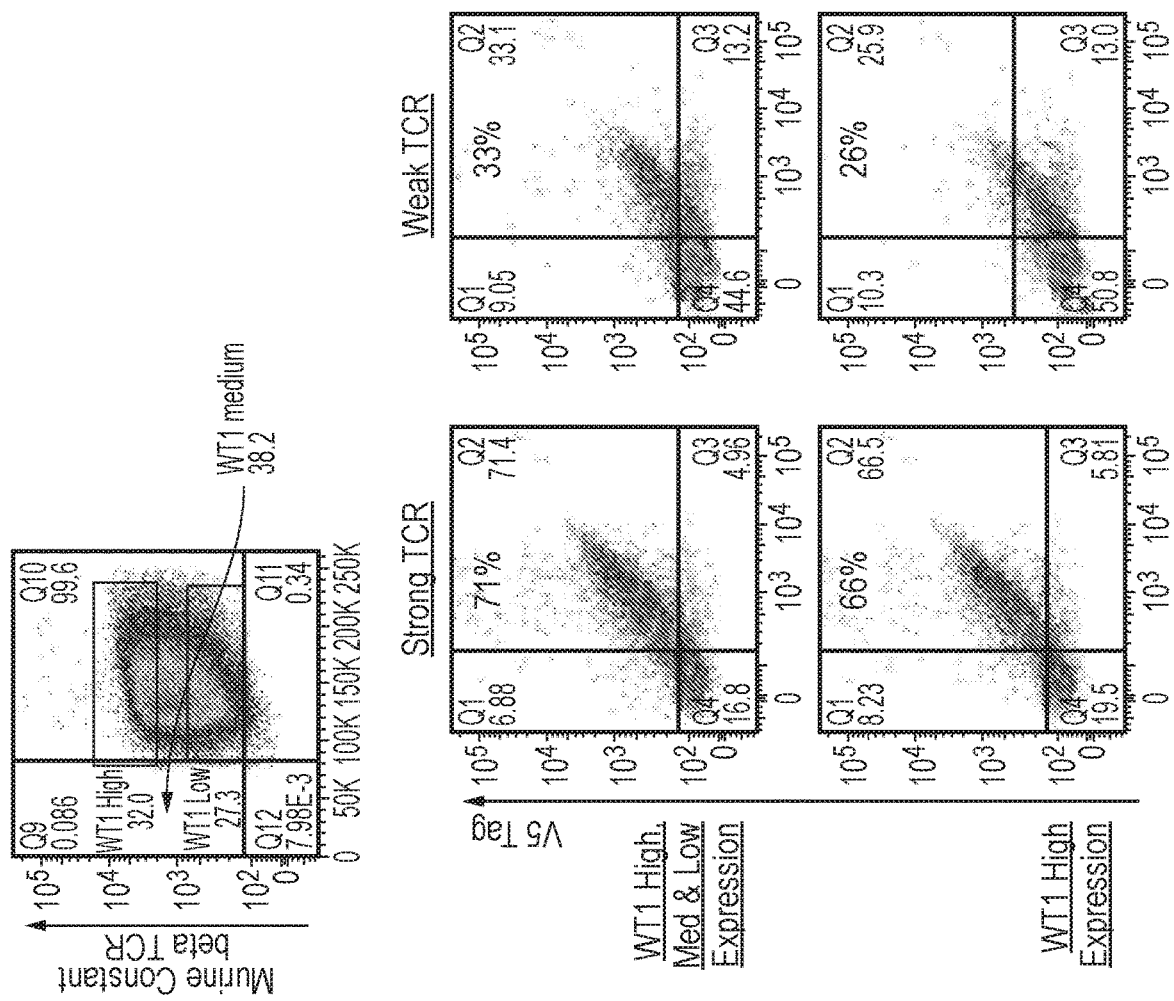
FIG. 7—Expression of strong and weak TCRs in Jurkat cells expressing low, medium and high expression of the modified WT1 TCR.
Figure 7:
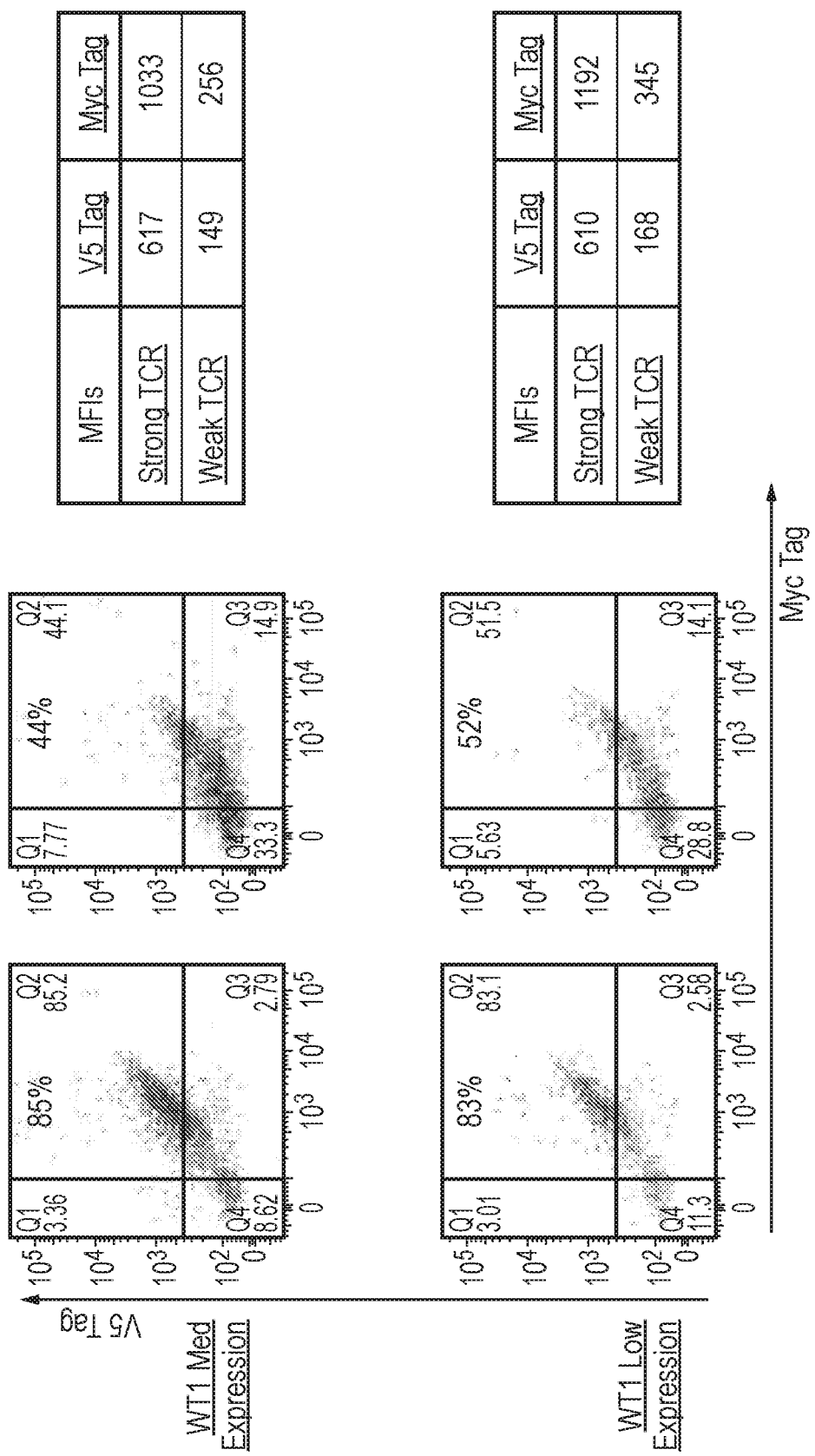

Expression of Strong and Weak TCRs in Jurkat Cells Expressing Low, Medium and High Expression of the Modified WT1 TCR Jurkat cells expressing the modified WT1 TCR were transduced with pMP71 vectors encoding the generic strong or weak TCRs. 72 hours after transduction, Jurkat cells were stained with anti-CD19, murine TCR constant domain, V5 Tag and Myc Tag antibodies (FIG. 7). Jurkat cells were first gated on high CD19 expression and then on high, medium and low expression of murine TCR constant domain. For all three separate WT1 TCR populations and the WT1 expressing cells as a whole, the V5 Tag and Myc Tag expression was determined. The MFI of V5 Tag and Myc Tag were also determined.

Figure 8:
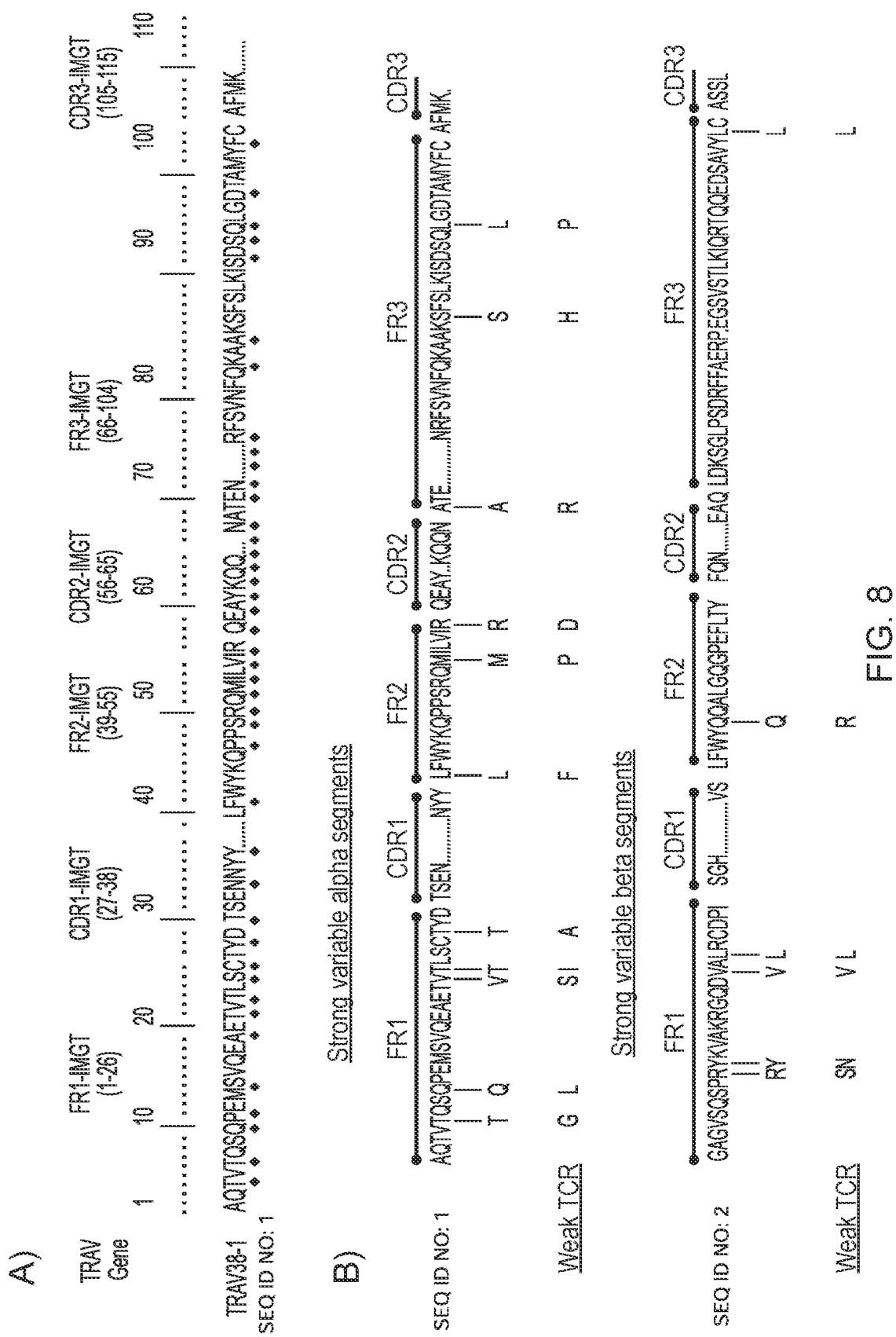
FIG. 8—Bioinformatics analyses of strong and weak expression TCRs.
A) The sequencing information from the clonotyping was used to compare all the residues at each position for all the strong and weak TCRs that had been sequenced. After TCR alignment, residues that had a high occurrence in particular positions in the strong TCR, compared to the weak TCR are indicated (*) in the figure using TRAV38-1 as an example. B) Analysis of the predicted 3D structure of strong and weak TCR variable segments.

Example 3—Bioinformatics Analysis to Identify Key Features Correlating to Strength of TCR Expression The sequencing information from the clonotyping was used to compare all the residues at each position for all the strong and weak TCRs that had been sequenced. After TCR alignment, residues that had a high occurrence in particular positions in the strong TCR, compared to the weak TCR are indicated (*) in the figure using TRAV38-1 as an example (FIG. 8A).

The residues which showed prevalence in the strong TCR was further analysed and refined to only include residues in the framework regions that have implications in stabilising the structure and pairing of the TCR chains. These residues are hi-lighted (*) using TRAV38-2 and TRBV7-8 as the backbone (FIG. 8B). The top line is the residues in the strong TCR. The bottom line is the equivalent residues in the weak TCR.

Example 4—Engineering of Strong Expression and Weak Expression TCRs

To engineer the strong expression TCR with weak residues, the strong TCR was used as a backbone and all strong residues that were predicated to be important in TCR strength were replaced with the weak TCR residues in the relevant position.

To engineer the weak TCR with strong residues, the weak TCR was used as a backbone and all strong residues that were predicated to be important in TCR strength replaced with weak TCR residues in the relevant position.

Figure 9:
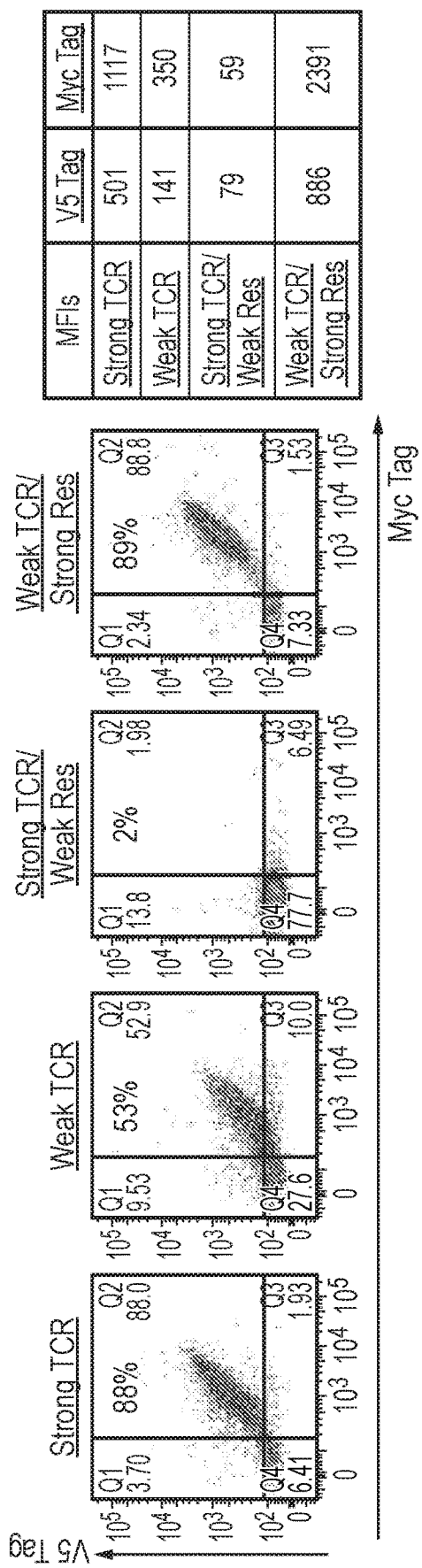
FIG. 9—Mutation of all identified key residues to reverse strong and weak expression TCRs in both a non-competitive environment (Jurkat cells not expressing TCR) and a competitive environment (Jurkat cells expressing the WT1 hybrid TCR).
Figure 9:
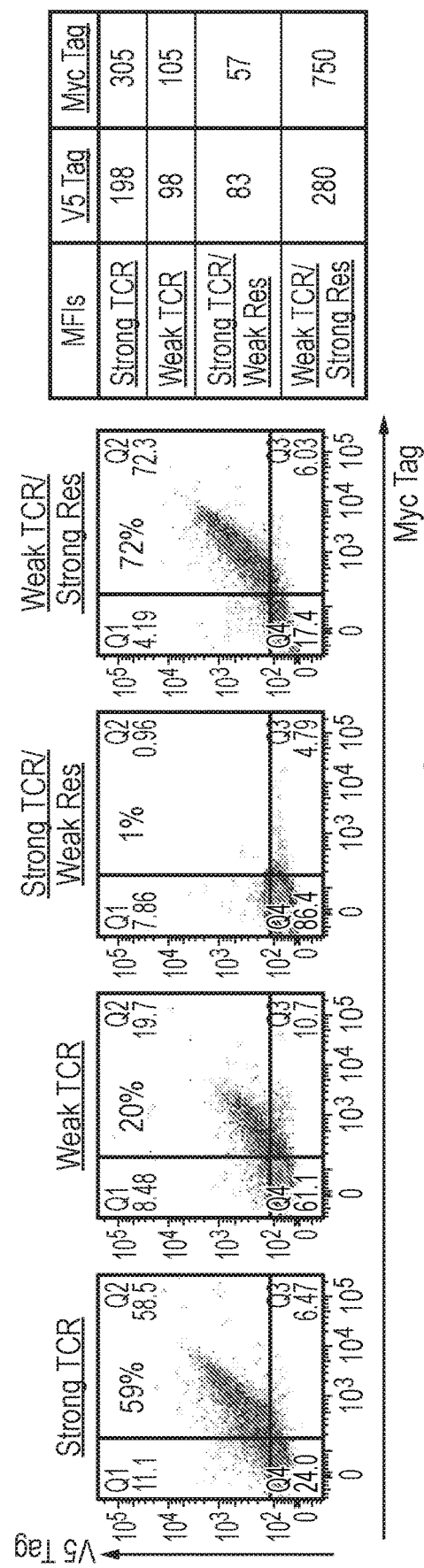

Jurkat cells without TCR (top row), and Jurkat cell expressing the WT1 murinised TCR (bottom row), were transduced with the stated TCR and 72 hours later stained with anti-CD19, V5 Tag and Myc Tag antibodies. Jurkat cells were gated on high CD19 expression and the V5 Tag and Myc Tag expression was determined. The MFI of V5 Tag and Myc Tag were also determined for the CD19+ high expressing cells (FIG. 9).

Example 5—Effect of Mutating Individual Residues on TCR Expression

The Individual Effect of Strong Residues on TCR Expression

The generic weak TCR was used as the backbone and the quick change PCR mutagenesis technique was used to make a series of TCRs which had only one of the predicted strong residues replacing the weak TCR residue at the relevant position whilst retaining the rest of the weak TCR backbone.

Figure 10:
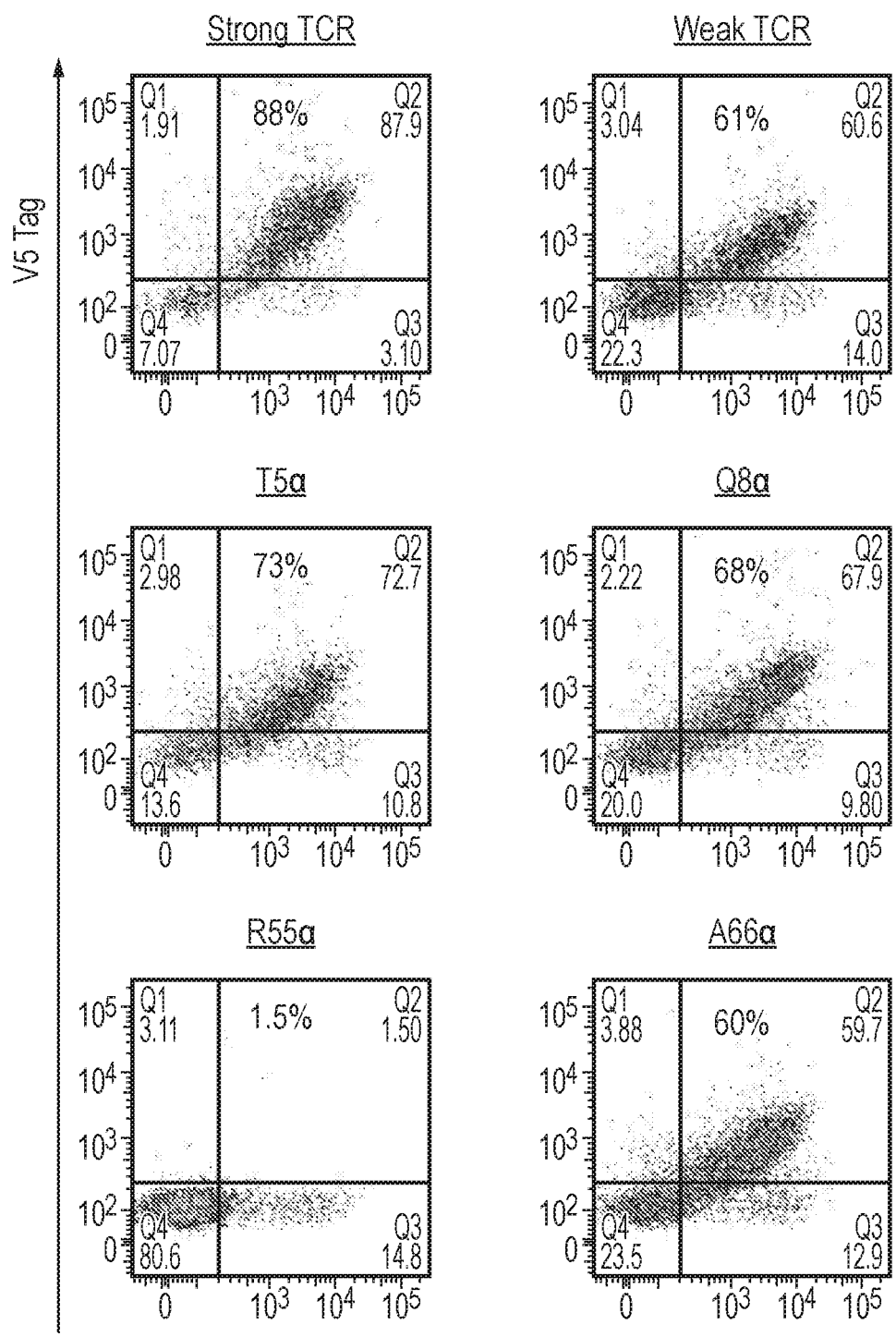
FIG. 10—Alteration of individual key residues impacts the expression level of an exogenous TCR in a non-competitive environment (Jurkat cells not expressing TCR).
Figure 10:
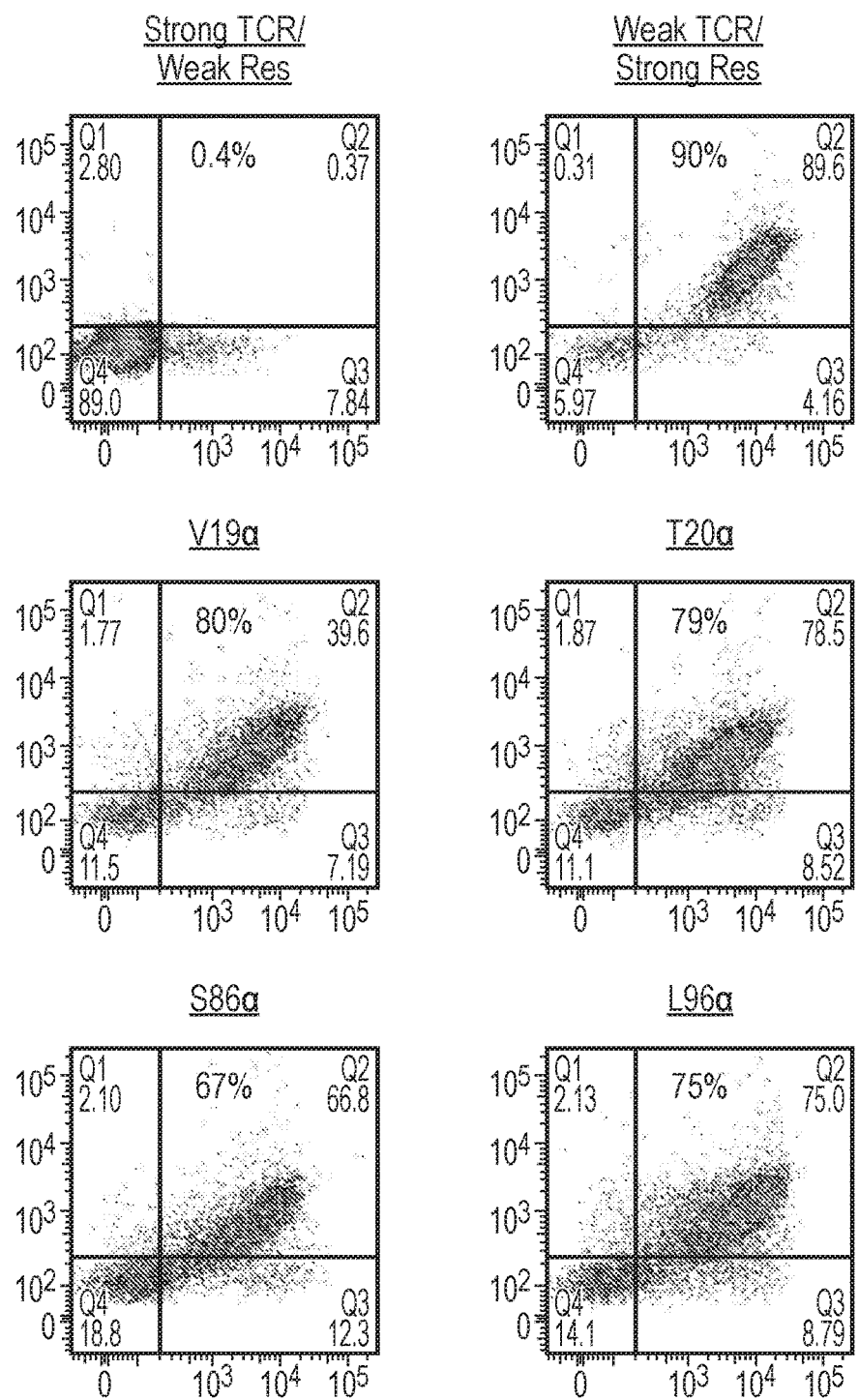
Figure 10:
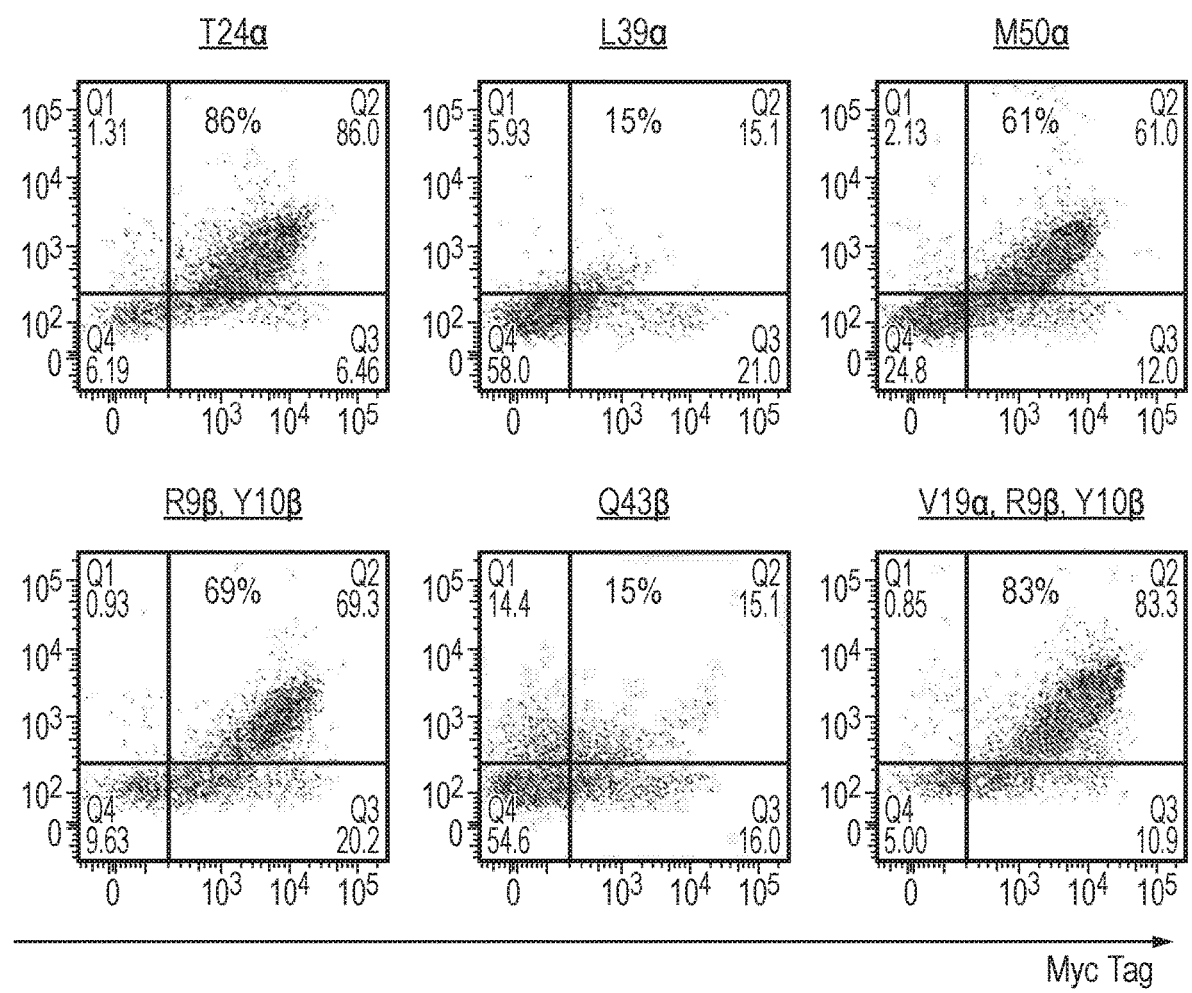
Figure 11:
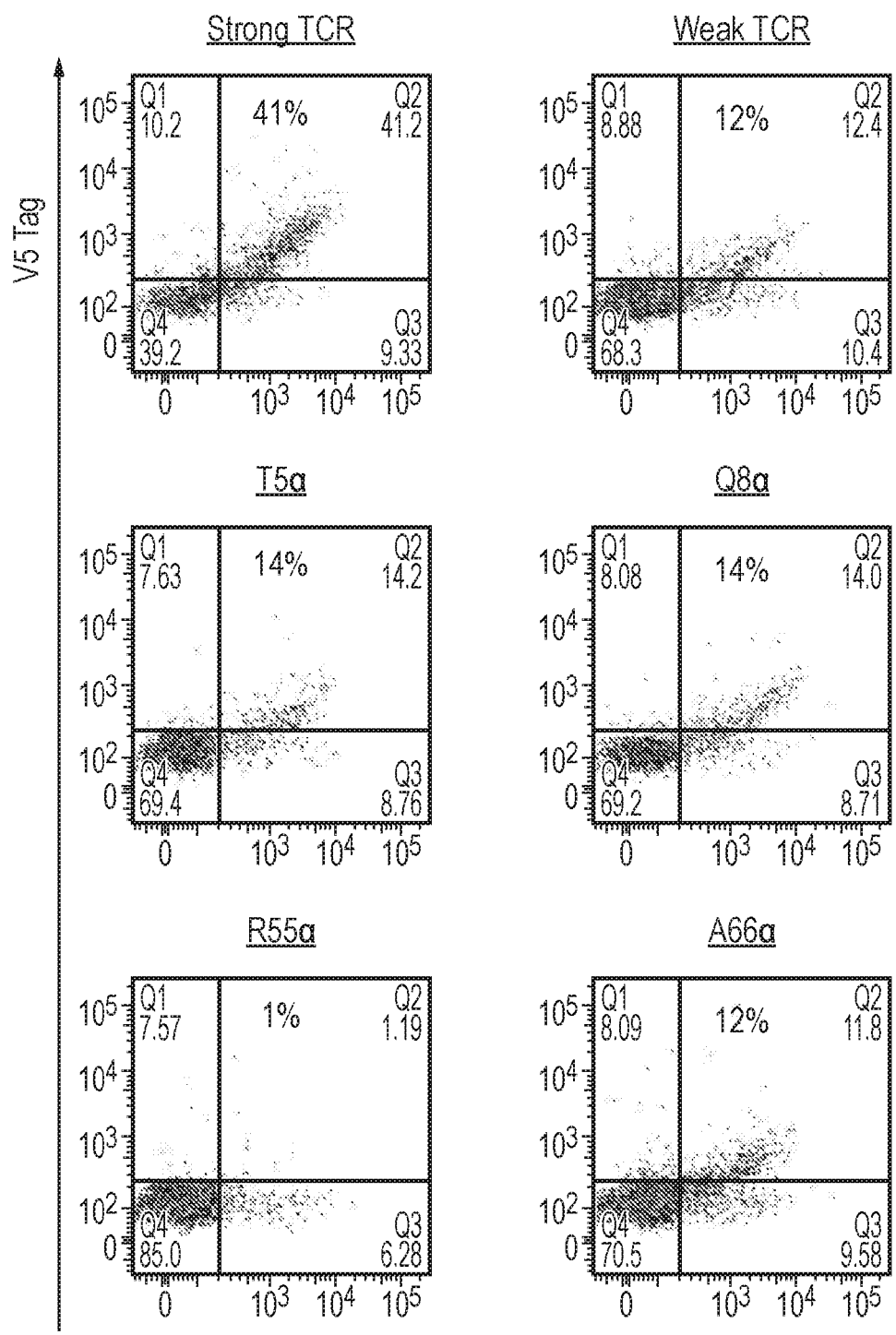
FIG. 11—Alteration of individual key residues impacts the expression level of an exogenous TCR in a competitive environment (Jurkat cells expressing the WT1 hybrid TCR).
Figure 11:
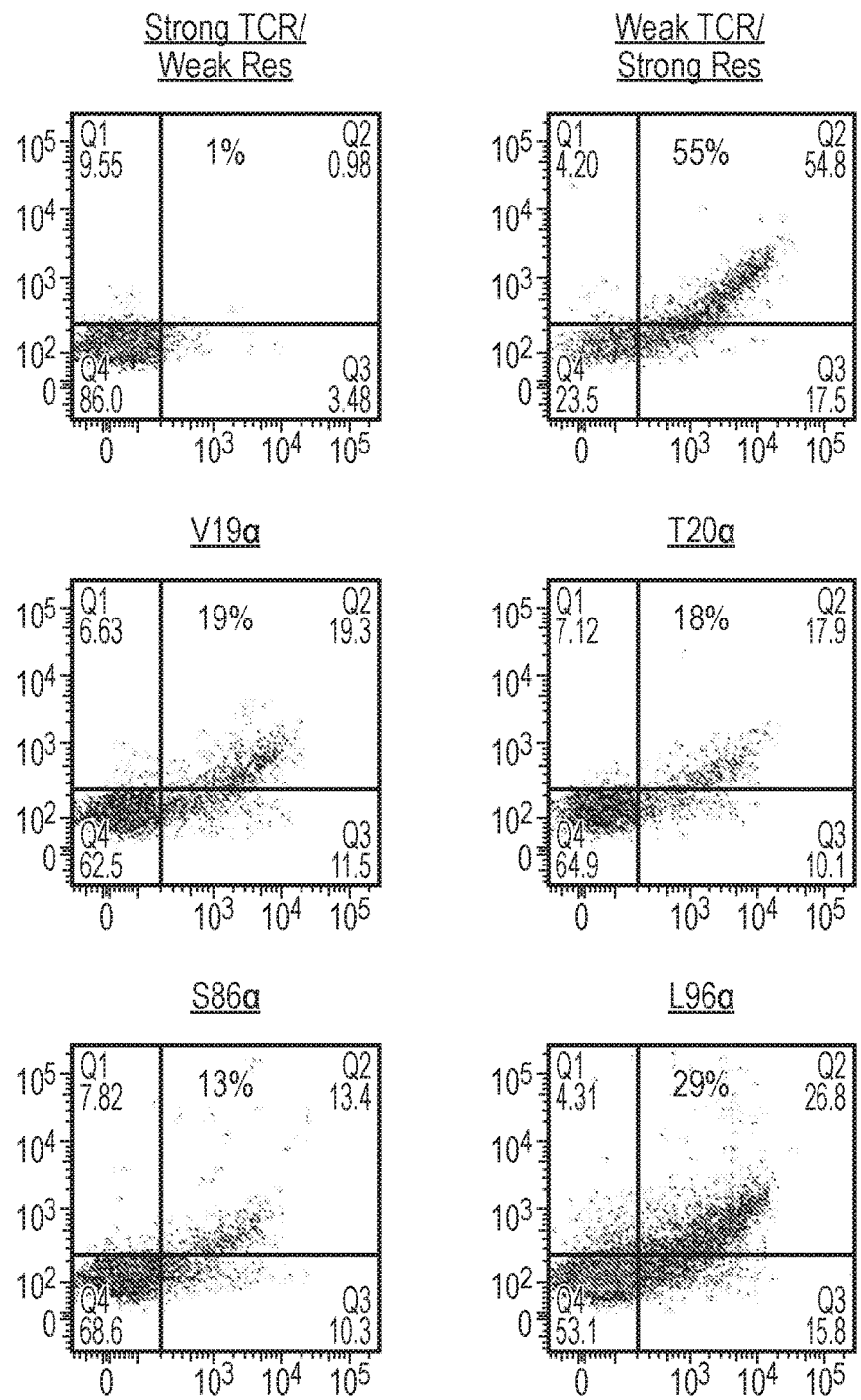
Figure 11:
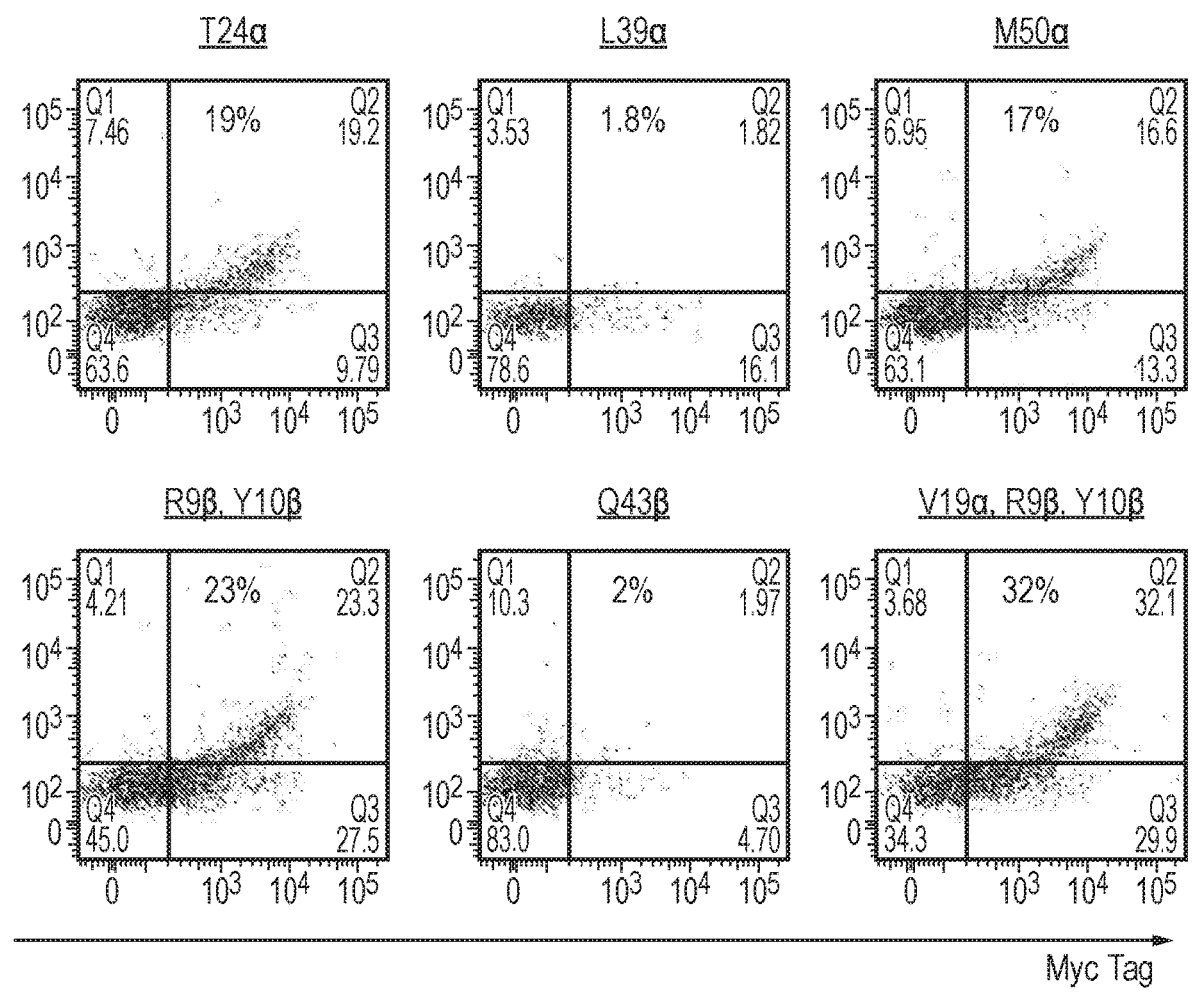

The mutated TCRs are labelled so that the letter represents the amino-acid the number is the position in the TCR framework and the α or β indicates whether the residue is in the alpha chain or the beta chain. The last plot, bottom row, right side has 3 residue changes, V19 on the alpha chain and R9, Y10β on the beta chain (FIGS. 10 and 11).

Jurkat cells without TCR (FIG. 10) and Jurkat cells expressing the modified WT1 TCR (FIG. 11), where transduced with the pMP71 retrovirus encoding the indicated TCR. 72 hours after transduction, transduced cells were stained with anti-CD19, V5 Tag and Myc Tag antibodies. Cells were gated on high CD19 expression and the V5 Tag and Myc Tag expression was determined.

FIG. 13 shows the results of experiments where Jurkat cells without TCR (A) and Jurkat cells expressing the modified WT1 TCR (B) where transduced with the pMP71 retrovirus encoding the indicated TCRs. 72 hours after transduction, the cells were stained with anti-CD19, V5 Tag, Myc Tag and murine constant beta TCR antibodies. Cells were gated on high CD19 expression and the V5 Tag, Myc Tag and murine constant beta TCR expression was determined. The MFI of V5 Tag, Myc Tag and murine constant beta TCR expression were also determined for the CD19+ high expressing cells. (C) MFI of V5 Tag and Myc Tag for Jurkat cells without TCR. (D) MFI of V5 Tag, Myc Tag and murine constant beta TCR for Jurkat cells expressing the modified WT1 TCR The results show that F39 of the α chain, D55 of the α chain and R43 of the β chain increases the surface expression of the TCR. Furthermore, the mutation of the above three residues was also shown to decrease the amount of WT1 TCR expressed on the cell surface in Jurkat cell competition experiments.

Example 6—Effect of Mutating Variable Domain Residues to L96α, R9β and Y10β in Antigen-Specific TCRs Cell Surface Expression in Jurkat Cells Jurkat cells (which do not contain endogenous TCR alpha or beta chains), were transduced with pMP71 vectors encoding either unmodified wild-type CMV or WT1 TCRs, or the same TCRs that were mutated to contain L96α, R9β and Y10β. 72 h after transduction, Jurkat cells were stained with anti-CD19 Abs and either CMV tetramer or Vβ2.1 (to determine WT1 variable beta expression) Abs.

Figure 14:
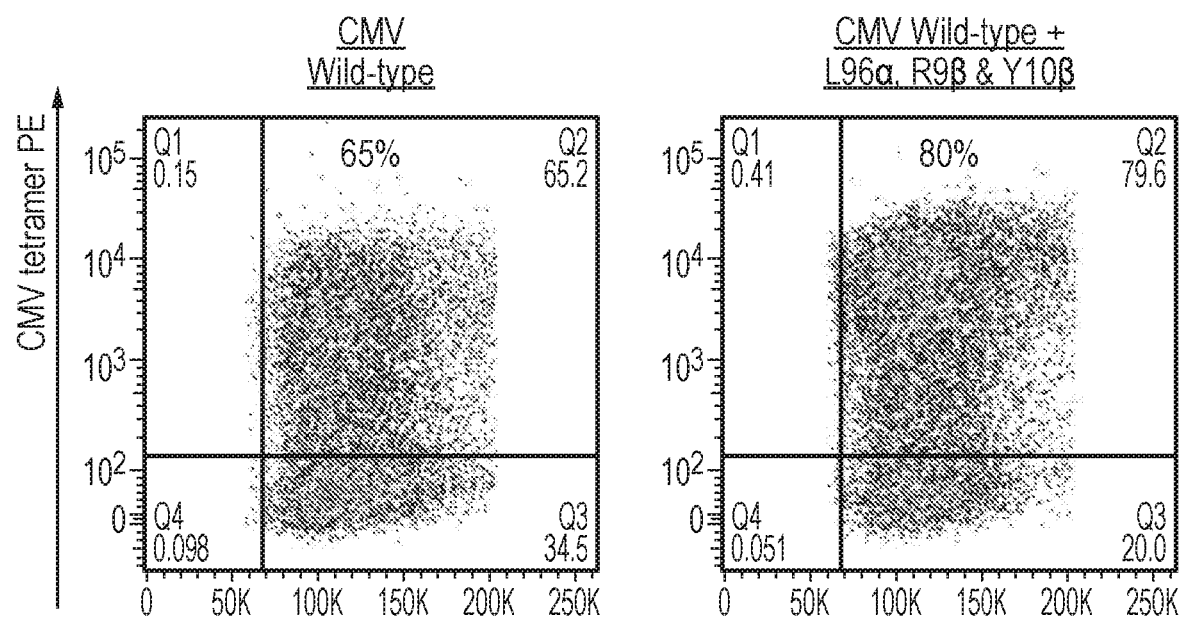
FIG. 14—Change of variable domain residues to L96α, R9β and Y10β improves CMV and WT1 TCR expression in Jurkat cells.
Figure 14:
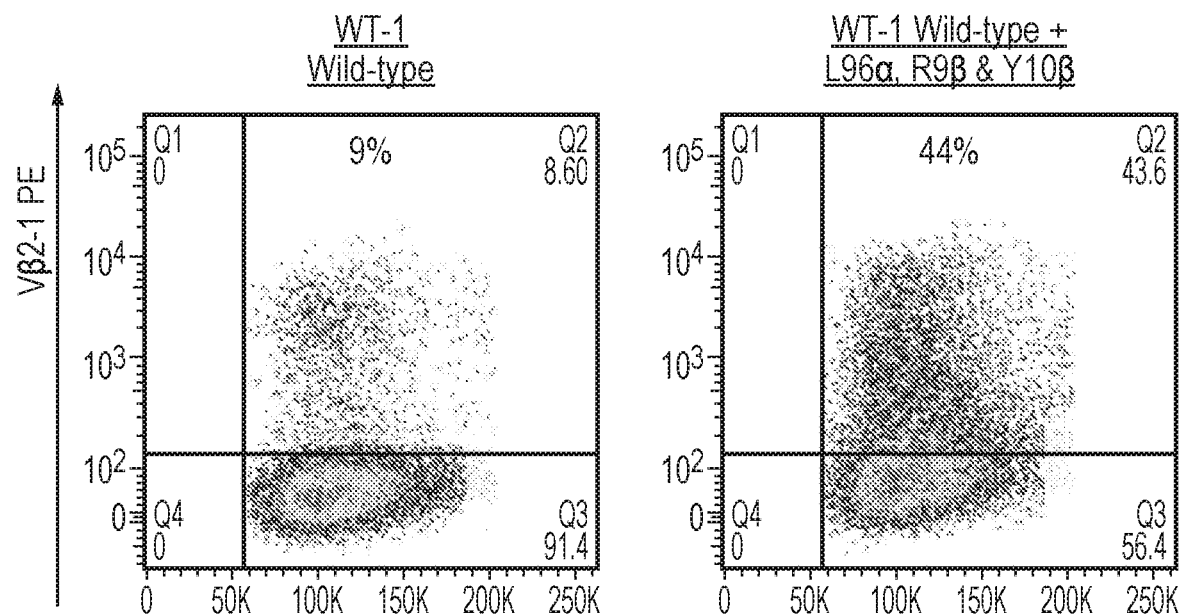

Cells were first gated on high CD19 expression and then CMV tetramer and or Vβ2.1 expression was determined (FIG. 14).

Cell Surface Expression in Primary T Cells

Figure 15:
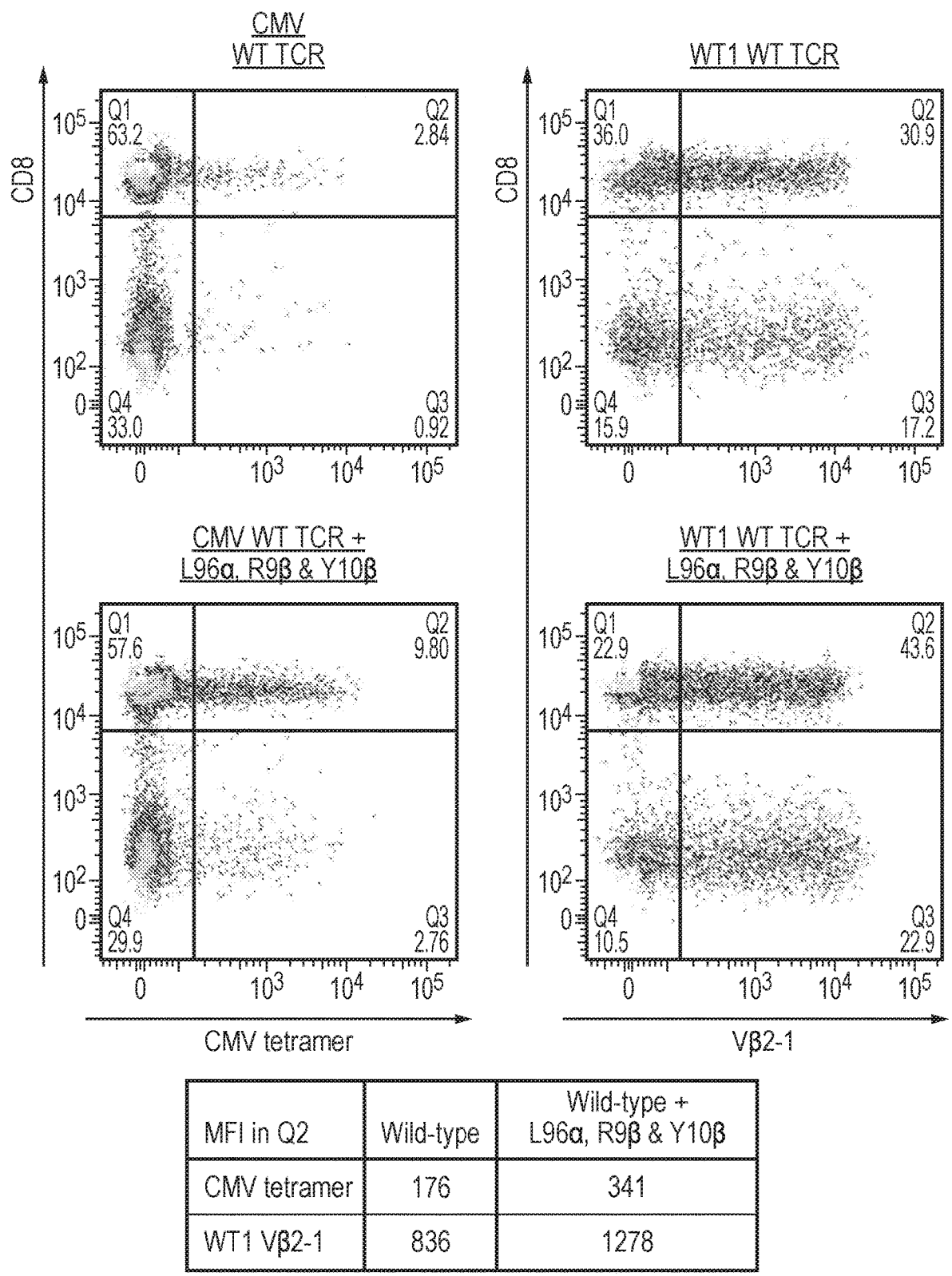
FIG. 15—Change of variable domain residues to L96α, R9β and Y10β improves CMV and WT1 TCR expression in primary peripheral blood T cells.

Activated, primary T cells were transduced with pMP71 vectors encoding either unmodified wild-type CMV or WT1 TCRs, or the same TCRs that were mutated to contain L96α, R9β and Y10β. 72 h after transduction, the T cells were stained with anti-CD3, CD8 and CD19 Abs and either CMV tetramer or Vβ2.1 Abs. Cells were gated on CD3+ and CD19 high T cells, and then TCR expression was determined using tetramers or anti-vβ2.1 antibodies to detect the CMV- and WT1-TCR, respectively (FIG. 15).

Figure 16:
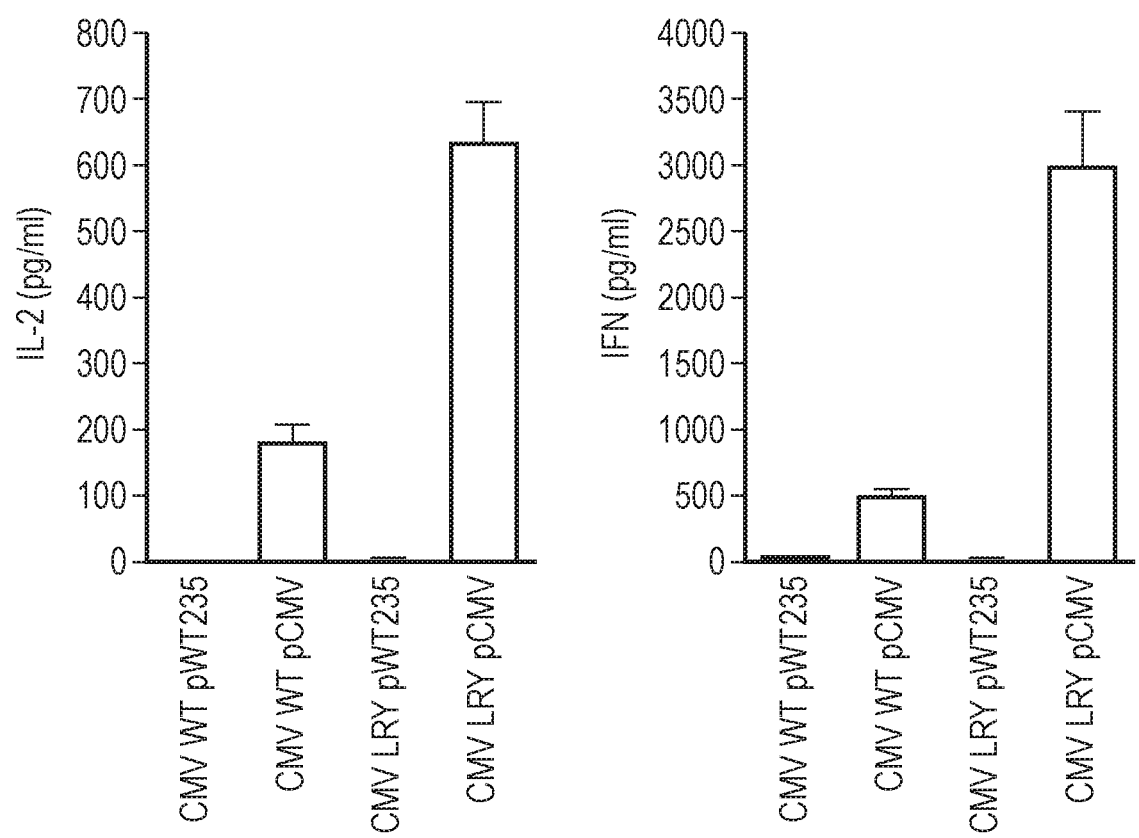
FIG. 16—Change of variable domain residues to L96α, R9β and Y10β improves antigen specific cytokine production.

Activated, primary T cells were transduced with pMP71 vectors encoding either unmodified wild-type CMV or the same TCR mutated to contain L96α, R9β and Y10β. 5 days after transduction, T cells were co-cultured with APCs expression the pCMV peptide or the irrelevant peptide pWT235. After 18 h co-culture, the supernatant was collected and IL-2 and IFN-γ production was determined by ELISA (FIG. 16).

Figure 17:
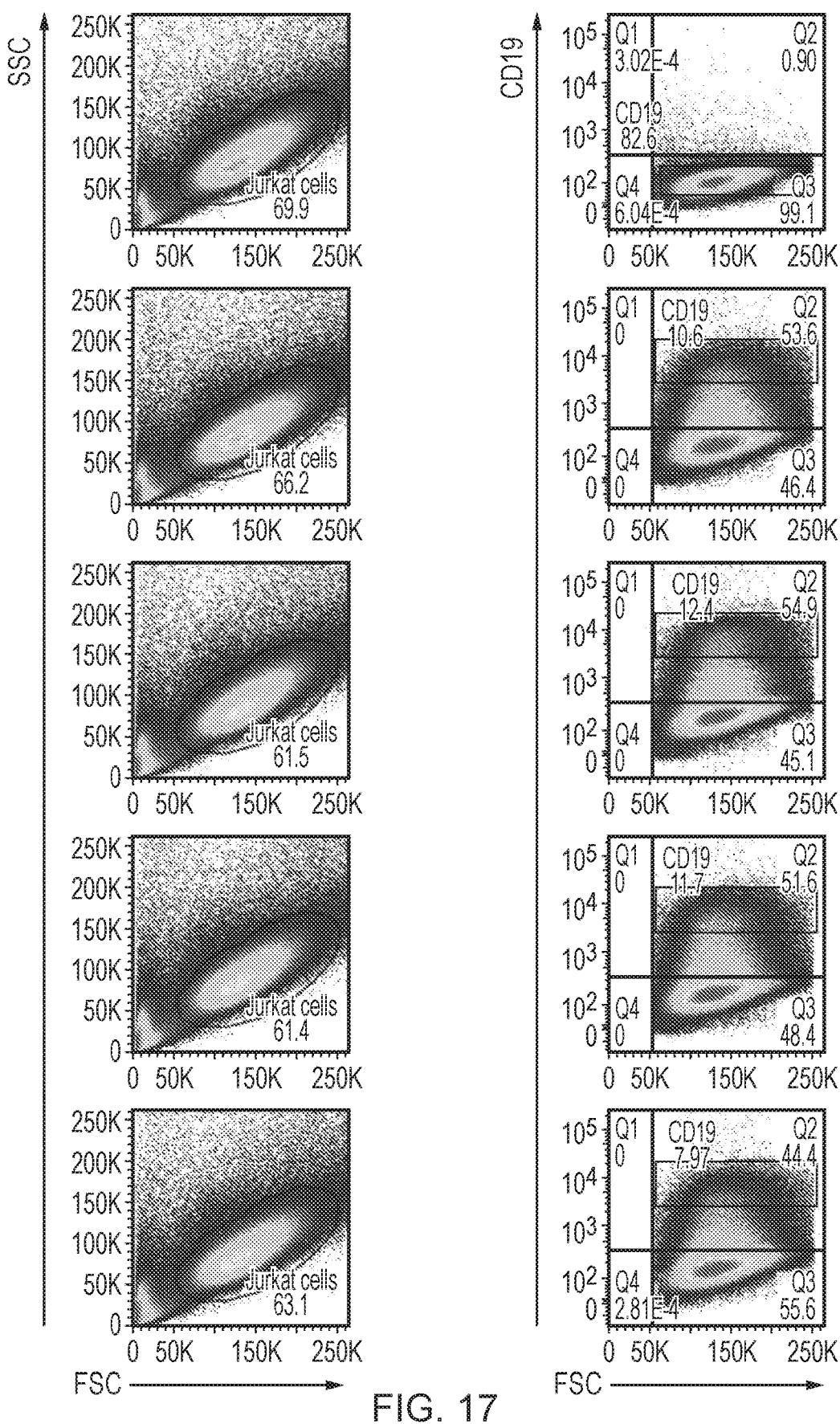
FIG. 17—Cells transduced with well expressed and poorly expressed TCRs contain similar amounts of TCR mRNA.
Figure 17:
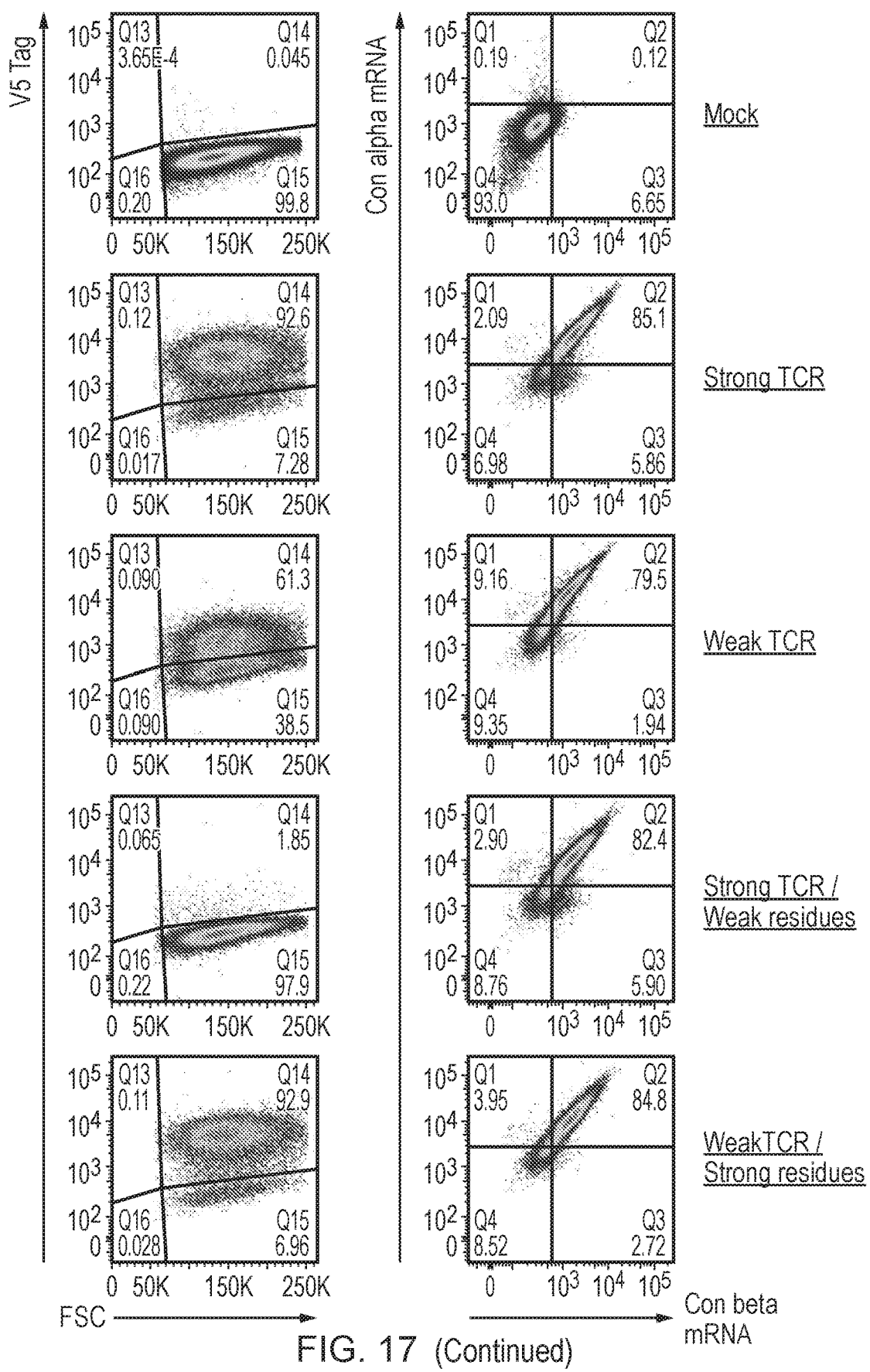

Cells Transduced with Well Expressed and Poorly Expressed TCRs Contain Similar Amounts of TCR mRNA Jurkat cells, without endogenous TCRs, were transduced with pMP71 vectors encoding either the generic strong TCR, or the generic weak TCR, or the generic strong TCR containing the predicted weak residues, or the generic weak TCR containing the predicted strong residues. The affymetrix primeflow RNA assay was used to determine the percentage of CD19+ high cells expressing the constant alpha mRNA and the constant beta mRNA. The MFI of the constant alpha and beta mRNA was determined for the four populations. In addition, the percentage of CD19+ high Jurkat cells expressing V5 Tag was also determined (FIG. 17).

Figures 1, 23:
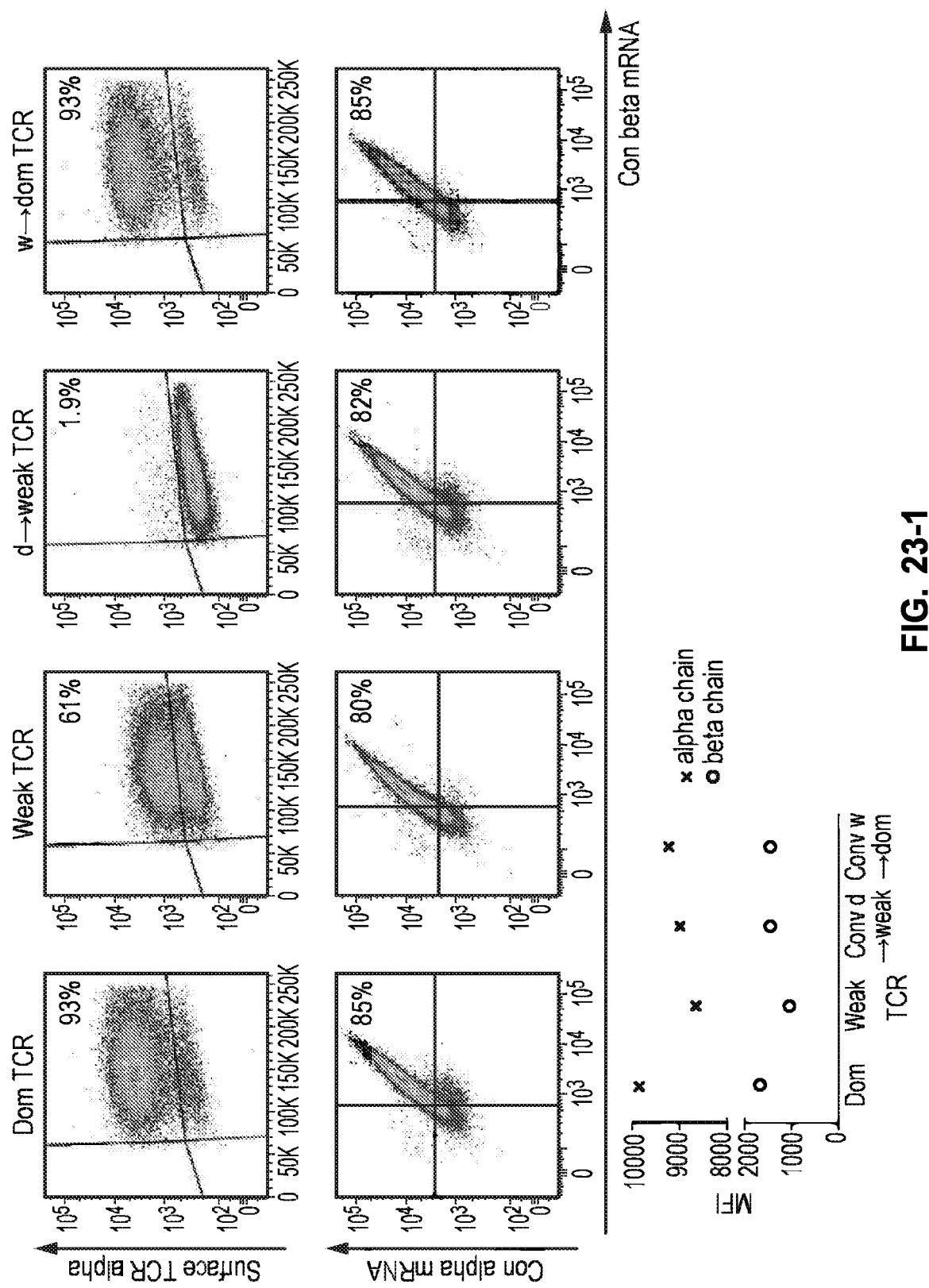
FIG. 23—Intracellular mRNA and protein levels are similar for TCR that are strongly and poorly expressed on the cell surface. Jurkat cells were transduced with 4 TCR constructs. (a) Anti-V5 surface staining was followed by cell permeabilisation and Affymetrix prime flow RNA staining to determine TCRα expression on the cell surface and intracellular TCRα/β mRNA, respectively. The dot plots show TCRα surface levels and intracellular TCRα/β mRNA levels of gated Jurkat cells expressing equivalent amounts of CD19. The diagram on the right shows the summary of TCRα/β mRNA expression levels of all 4 TCRs tested. (b) Jurkat cells were transduced with the w→domTCR and the w→domTCR followed by flow cytometry sorting to purify cells with high CD19 expression levels. These cells were permeabilised and stained with anti-CD19 antibodies (green) and anti-V5-antibodies for TCRα expression (red) followed by confocal microscopy. The bottom panel shows overlay of CD19 and V5/TCRα expression. (c) Single cell analysis of confocal data showing the quantification of CD19 and V5/TCRα expression of cells transduced with the w→domTCR (red) and the d→weakTCR (blue). (d) Cell surface levels of CD19 and V5/TCRα of the same TCR constructs was determined by flow cytometry of non-permeabilised cells.
Figures 2, 23:
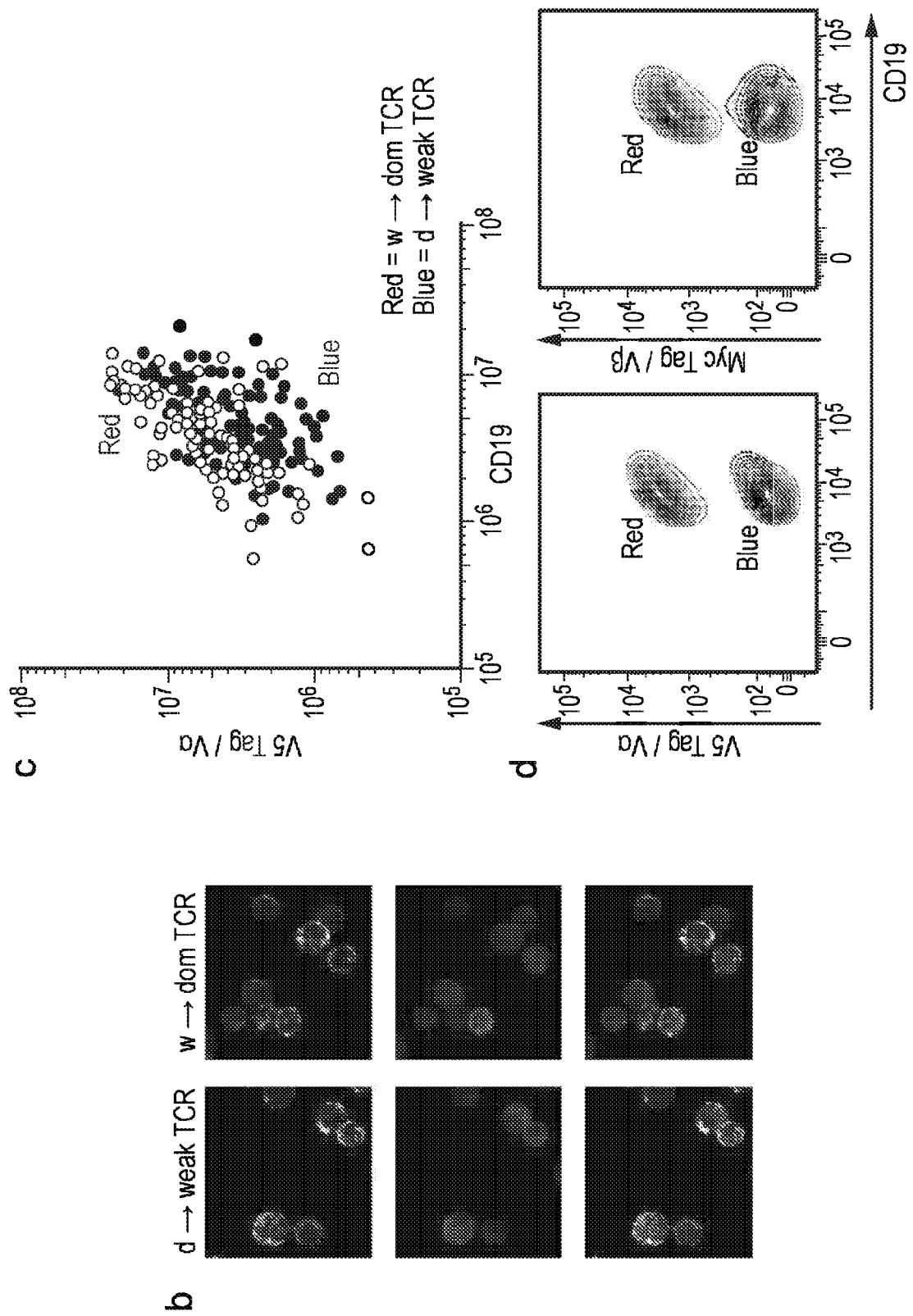

The level of α/β mRNA was similar for all TCRs analysed and did not correlate with the vastly different TCR surface expression levels (FIG. 23A). For example, a converted d→weakTCR was not detectable at the cell surface despite efficient mRNA expression.

Confocal microscopy was used to compare the level of intracellular protein with high TCR surface expression (w→domTCR) and low surface expression (d-weakTCR). Conformation independent antibodies specific for the V5 tag were used to asses the amount of intracellular α chain protein irrespective of TCR folding and pairing. Transduction of Jurkat cells with both TCRs demonstrated the presence of intracellular protein (FIG. 23B). Single cell quantification of the confocal data indicated a correlation between the intensity of CD19 and TCR staining and suggested that the amount of α chain was slightly higher for the TCR with efficient surface expression compared to the TCR with no surface expression (FIG. 9C).

However, comparison of the confocal TCR/CD19 profile and the cell surface expression profile determined by flowcytometry (FIG. 23D), demonstrated that the lack of TCR on the cell surface was not caused by a lack of intracellular TCR protein. This indicates that poor protein folding and inefficient TCR assembly was a major cause of poor expression of the d→weakTCR and was overcome by the use of dominant amino acid residues as identified herein.

Figure 20:
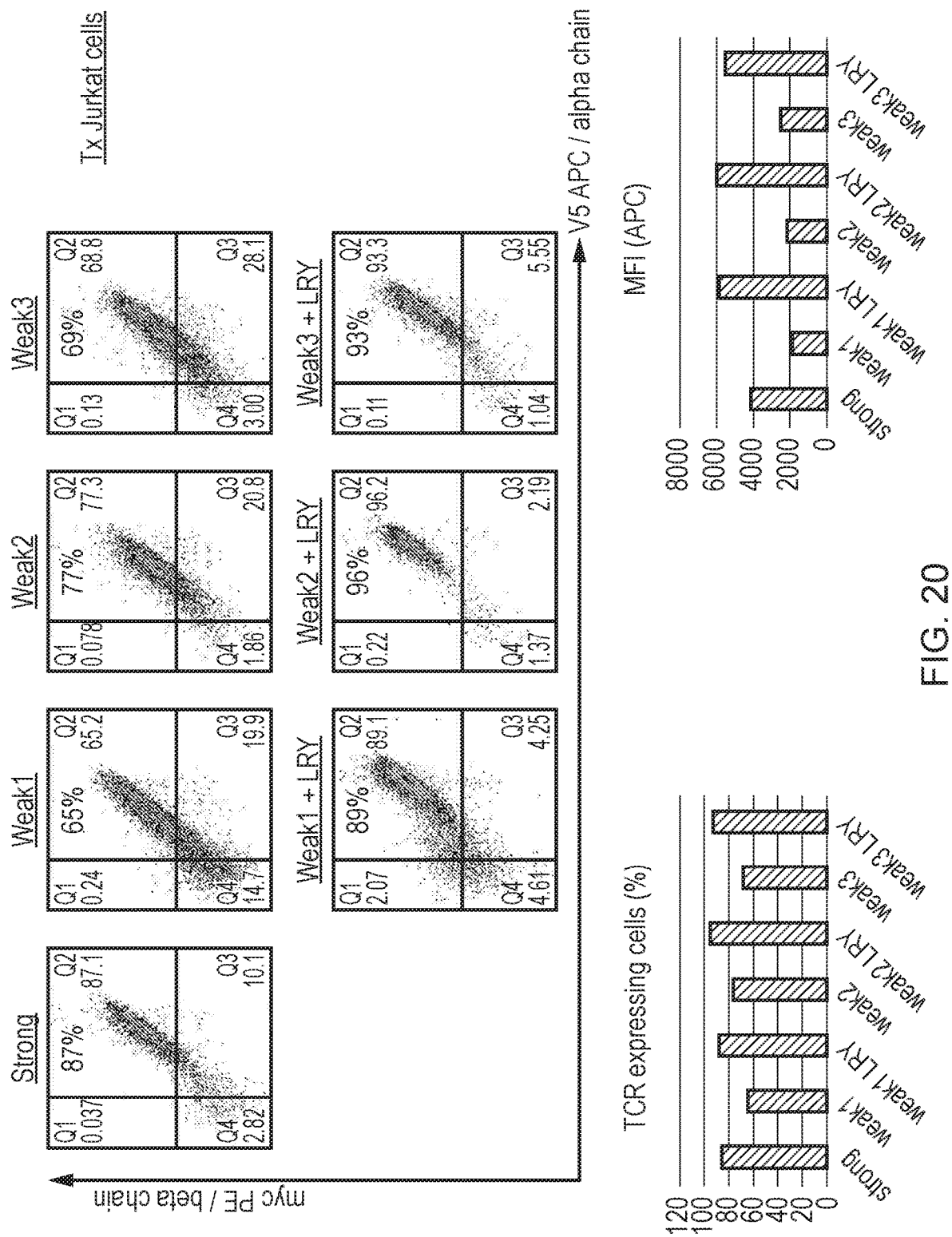
FIG. 20—Introduction of L96α, R9β and Y10β increases the cell surface expression of further weak TCR.

Further Exemplification of the Influence of L96α, R9β and Y10β on TCR Cell Surface Expression Two additional weak TCRs (weak 2 and 3) were investigated to determine the impact of introducing L96α, R9β and Y10β on the level of cell surface expression. The percentage of TCR expressing cells and the MFI of cell surface expression was increased for each weak TCR following the introduction of introducing L96α, R9β and Y10β (see FIG. 20).

Figure 21:
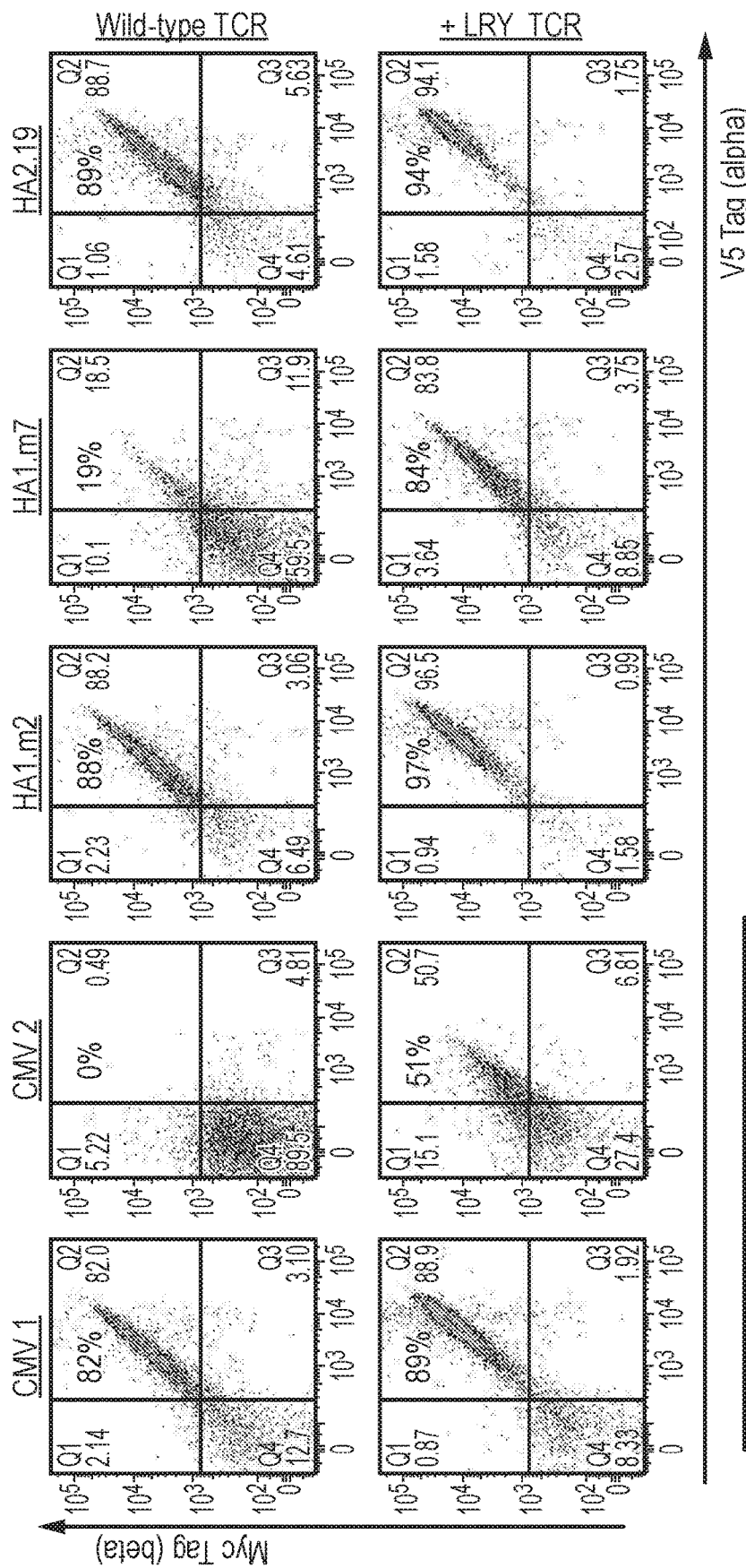
FIG. 21—Introduction of L96α, R9β and Y10β increases the cell surface expression of peptide specific TCRs in Jurkat cells with no endogenous TCR.
Figure 22:
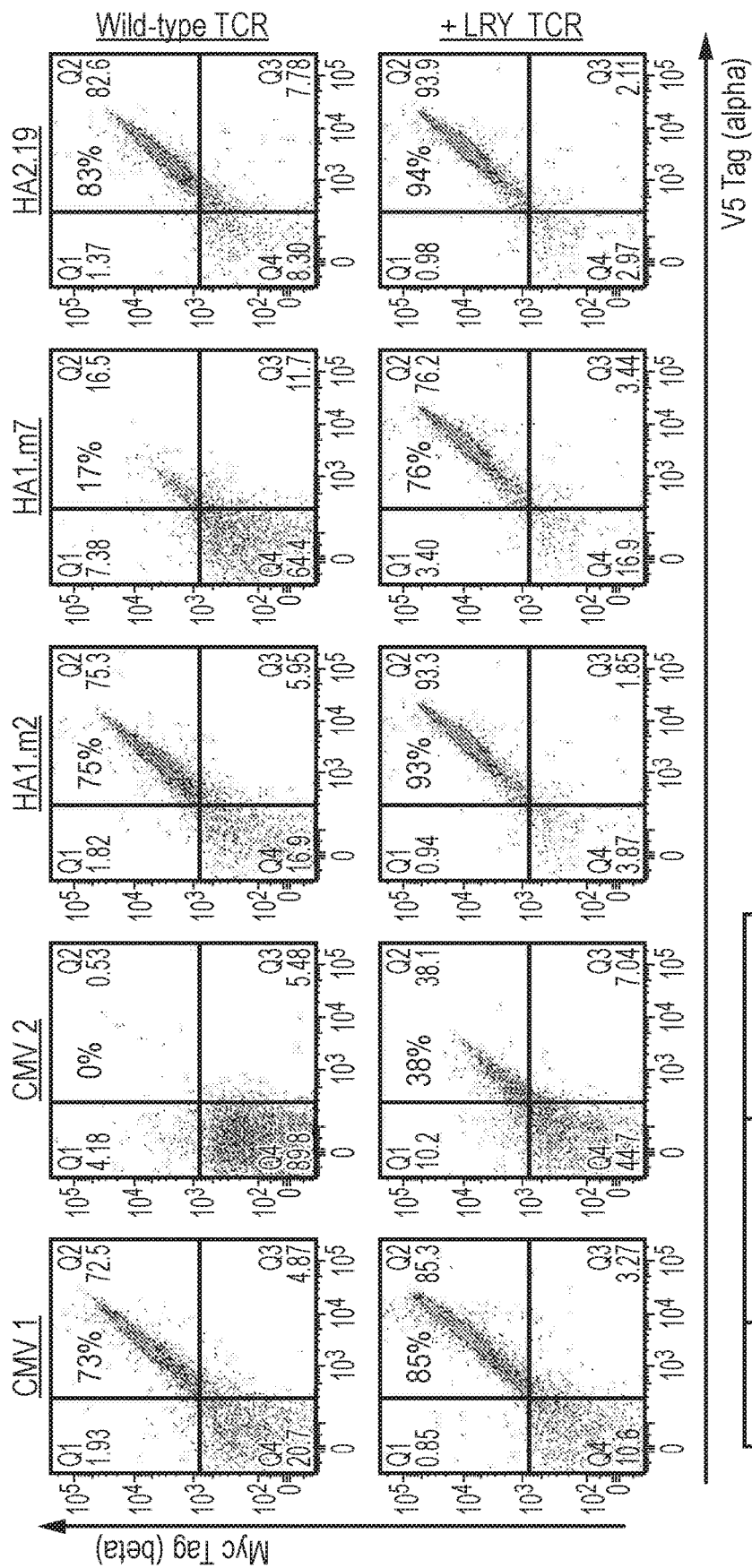
FIG. 22—Introduction of L96α, R9β and Y10β increases the cell surface expression of peptide specific TCRs in Jurkat cells also expressing an exogenous WT1 TCR.

In addition, the cell surface expression of four antigen-specific TCRs (CMV2, HA1.m2, HA1.m7, HA2.19) was enhanced by the introduction of only three amino acid changes (L96α, R9β and Y10β) (see FIGS. 21 and 22).

Example 7—Contribution of TCRα Vs TCRβ to TCR Cell Surface Expression

Figure 18:
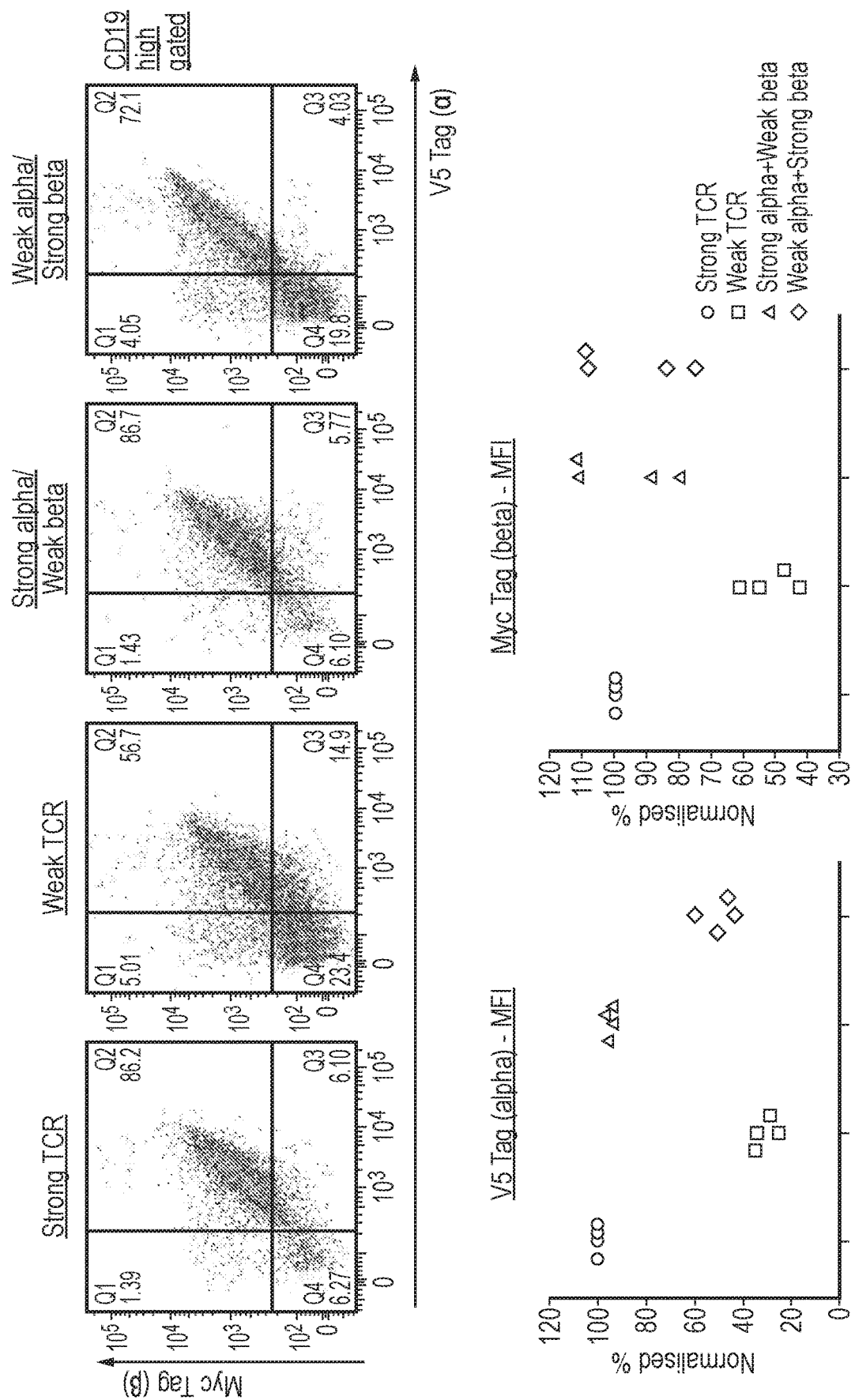
FIG. 18—Contribution of TCR alpha vs TCR beta to TCR expression.

Jurkat cells, without endogenous TCRs, were transduced with pMP71 vectors encoding either the strong TCR, or the weak TCR, or a TCR engineered to contain the strong alpha variable chain and the weak beta variable chain, or a TCR engineered to contain the weak alpha variable chain and the strong beta variable chain. 72 h after transduction, Jurkat cells were stained with anti-CD19, V5 Tag and Myc Tag antibodies. Jurkat cells were gated on high CD19 and the V5 Tag and Myc Tag expression was determined. The MFI of the V5 Tag and Myc Tag were also determined in the CD19+ high cells (FIG. 18).

Figure 24:
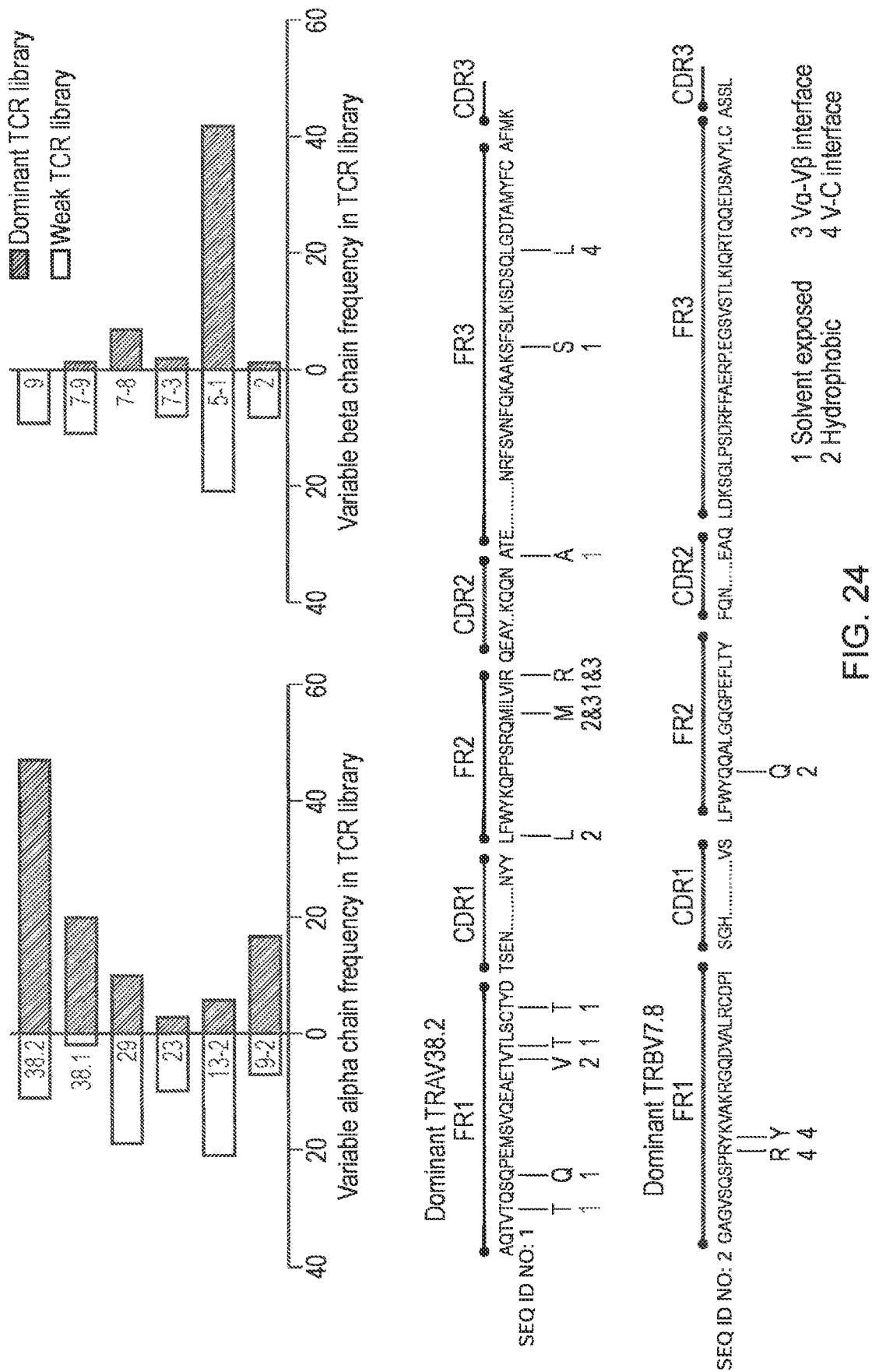
FIG. 24—Frequency of V-gene segment usage in the library of dominant/high expression TCRs (solid bars) and weak/low expression TCRs (open bars)
Based on their position within the 3D structure identified residues were broadly grouped in four classes of residues that differ between weak and strong TCR V domains and shown for TRAV38.2 and TRBV7.8:1. Solvent exposed (possible effects on folding); 2. Residues in hydrophobic core of domain (likely to affect V-domain stability); 3. Residues at interface between Vα and Vβ domains (ie potentially involved in interchain interactions); 4. Residues at interface between V and C domain of a single chain (ie potentially involved in intrachain interactions).

Example 8—Mapping of Residues Identified as Important in Cell Surface Expression Levels TCR structural modelling was used to determine how residues in the framework of the variable region may affect TCR stability. In particular, the molecular mechanism by which amino acid changes in a poorly expressed (weak) TCR resulted in enhanced surface expression was determined. The weak TCR that was most extensively tested in the present experiment consisted of TRAV13-2 and TRBV7-3 (see FIG. 24). Since the structure of the TRAV13-2 chain is yet to be determined, modelling using TRAV13-1 (PDB code 3PL6, Sethi et al.; 2011; J Exp Med; 208; 91-102), which is closely related to TRAV13-2, was used. The 3PL6 TCR structure consists of the TRAV13-1 chain paired with TRBV7-3, the same chain as the present weak TCR. 14 of the variable domain residues that were analysed in the present study were mapped on the weak TCR structure (FIG. 25A).

The change of P96α to L96α resulted in 3-fold increase in TCR expression (FIG. 4). This residue protrudes from the short helix that precedes strand F and packs against the Cα domain. Modelling of L96α in TRAV13-1 reveals additional hydrophobic packing interactions with non-polar residues of the Cα interface (e.g. V161α and P112α) relative to weak TCR (FIG. 25b). Thus, the improved TCR expression achieved with L96α is most likely due to enhanced stability of the Vα-Cα interface. Substitutions at position 9 and 10 of the β chain also enhanced TCR expression (FIG. 4). In TRBV7-3 the S9β and N10β residues mediate minimal interactions at the Vβ-Cβ interface (FIG. 25c). Modelling the replacement of S9β with R9β shows that it could form a potential salt bridge with neighboring E159β (CP domain) (FIG. 25c). Also, Y10β is predicted to form stacking interactions with residues that protrude from the Cβ domain (Y218β and H157β), which is likely to increase the stability of the Vβ-Cβ interface relative to the native TRBV7-3 (FIG. 25c). Thus, the improved TCR expression achieved by the introduction of R9β and Y10β is likely caused by the enhanced stability of the Vβ-Cβ interactions. The positive effect of V19α on TCR expression can be explained by its protrusion from strand B into the hydrophobic core. Replacing S19α with V19α shows that the side chain of valine could stabilise the hydrophobic core by mediating multiple non-polar interactions with L11α (strand A), V13α (strand A), I21α (strand B) and I91α (strand E) (FIG. 25d). Therefore, the V19α substitution enhances the stabilisation of the hydrophobic core of the Vα domain. Finally, A24α is a solvent exposed residue that protrudes from strand B. Modelling the replacement of A24α with T24α suggests that this residue is likely to mediate a hydrogen bonding interaction with the imidazole ring nitrogen of H86α (strand E) (FIG. 25e). Thus the generation of a new hydrogen bond can provide a molecular explanation of the improved TCR expression mediated by T24α (FIG. 4).

Based on their position within the 3D structure the identified residues were broadly grouped in four classes of residues that differ between weak and strong TCR V domains:
1. Solvent exposed (possible effects on folding)
2. Residue in hydrophobic core of domain (likely to affect V-domain stability)
3. Residue at interface between Vα and Vβ domains (ie potentially involved in interchain interactions)
4. Residue at interface between V and C domain of a single chain (ie potentially involved in intrachain interactions)

For example:

| Residue Class | Examples of residues |
| --- | --- |
| 1 | T5α/Q8α/T20α/T24α/R55α/A66α/S86α |
| 2 | V19α/L39α/M50α/Q43β |
| 3 | M50α/R55α |
| 4 | L96α/R9α/Y10α |

The identified residues affect structural features of the TCR. Hence, it is expected that conserved residues with similar properties will have similar structural effects. In particular, the residues found in homologous proteins with conserved function as defined by the Blosum62 score are expected to have similar effects on TCR strength.

For example, the residues L96α, R9α and Y10α affect the interface between V and C domain. As exemplified herein (see Example 6), these three residues consistently enhance the surface expression of TCR. Conserved amino acids and respective amino acids with a Blosum62 score greater than 0 are therefore also expected to enhance TCR expression.

Figure 26A:
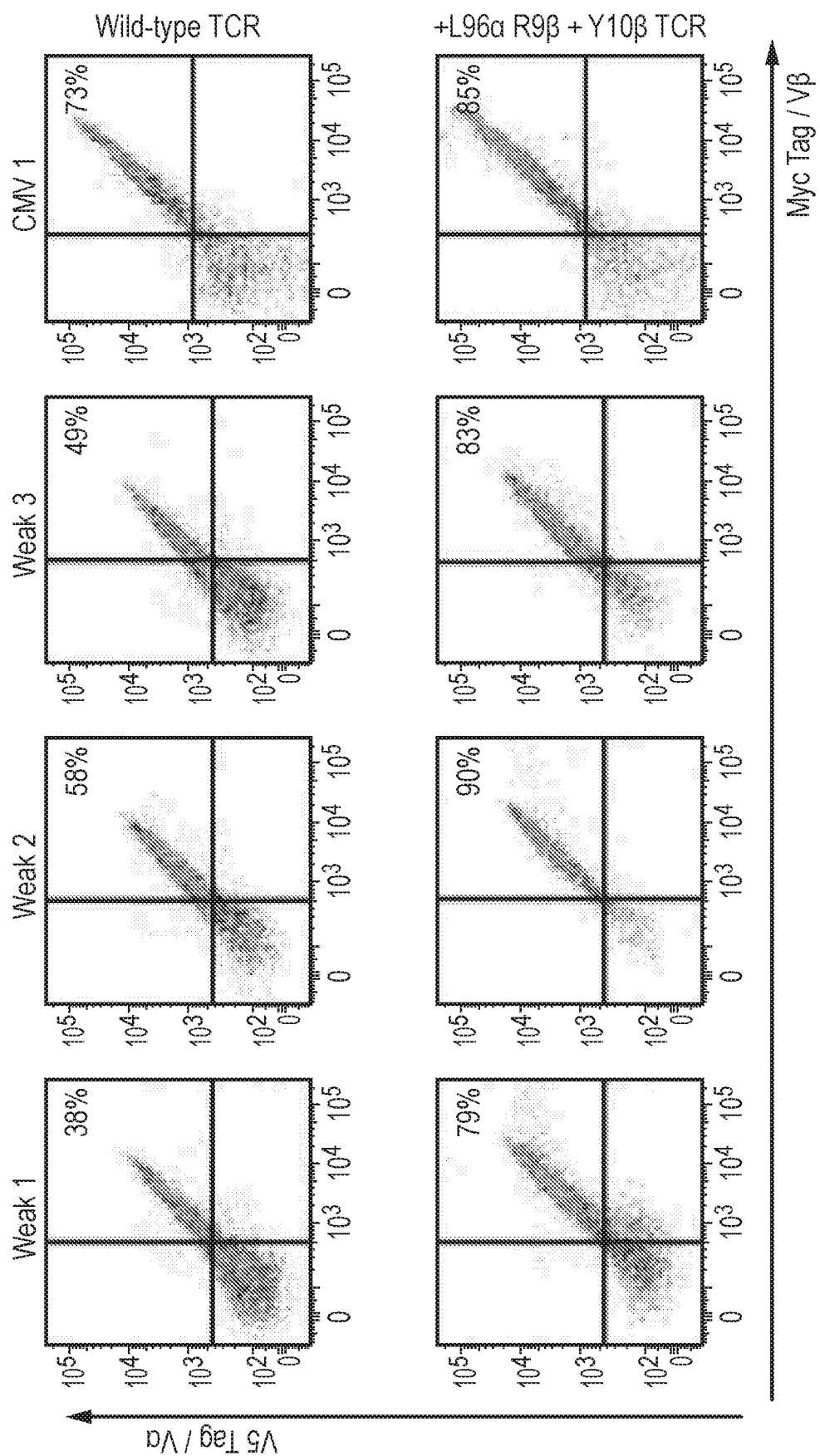
FIG. 26—Replacement of 3 framework residues consistently enhances TCR expression while reducing TCR mispairing. The role of L96α and R9β/Y10β was tested in 3 low expression TCRs selected from the low expression TCR library, and in 5 antigen-specific TCRs (2 TCRs specific for CMV-pp65, 2 TCRs specific for the HA1 minor histocompatibility antigen 27 and 1 TCR specific for the HA2 minor histocompatibility antigen). (a) Jurkat cells were transduced with the indicated wild-type TCRs (top row) or the modified TCR containing L96α, R9β, Y10β. α/β surface expression of gated cells expressing equivalent levels of CD19. (b) Summary of TCR α/β expression of all 8 wild type TCRs and LRY-modified TCRs. Representative of 3 separate experiments. (c) Human peripheral blood T cells were transduced with the indicated wild type TCRs and the LRY-modified variants. The dot plots show the expression of the introduced TCR α and β chain in gated T cells expressing equivalent levels of CD19.
Figure 26A:
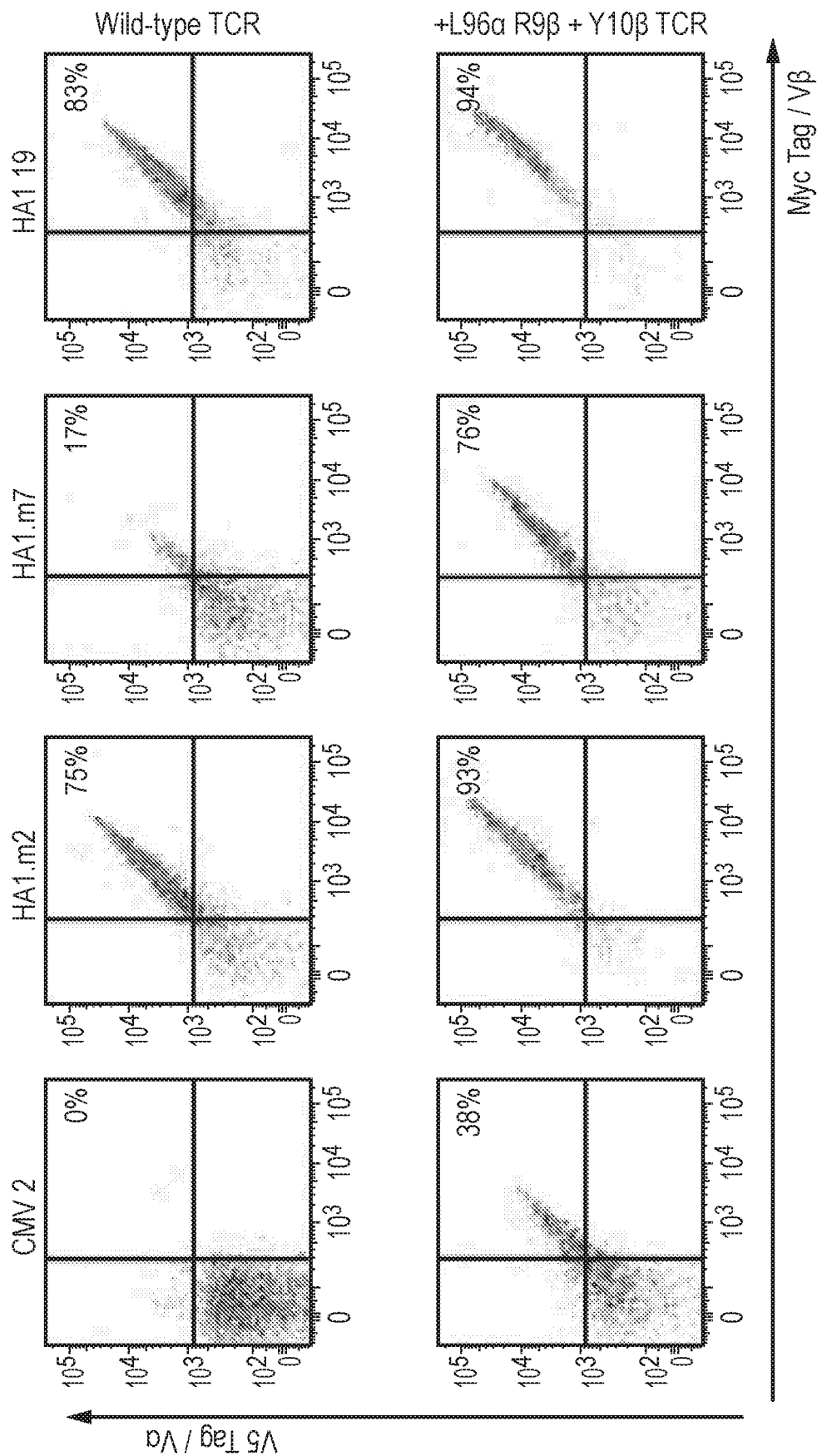
Figure 26B:
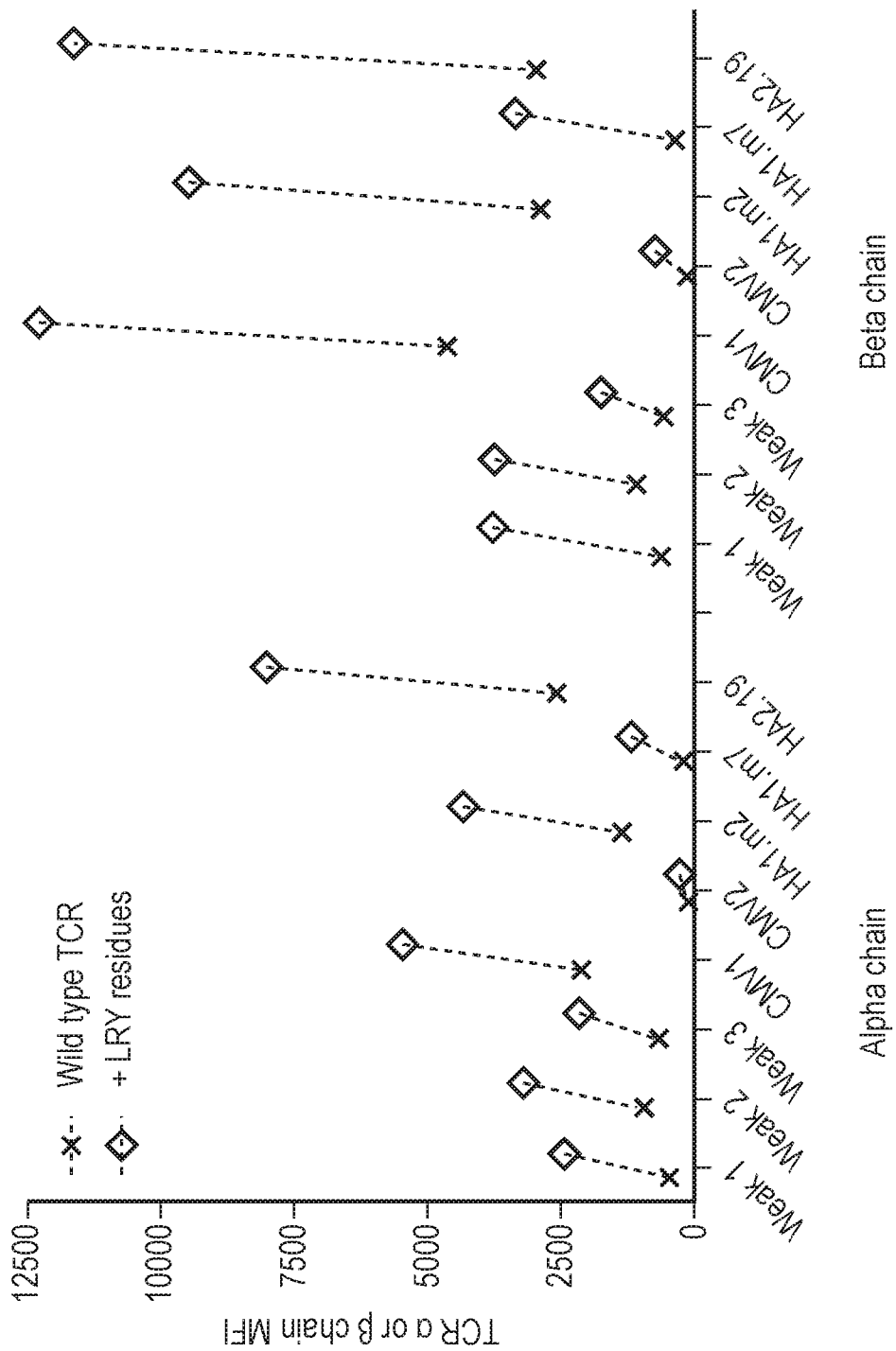
Figure 26C:
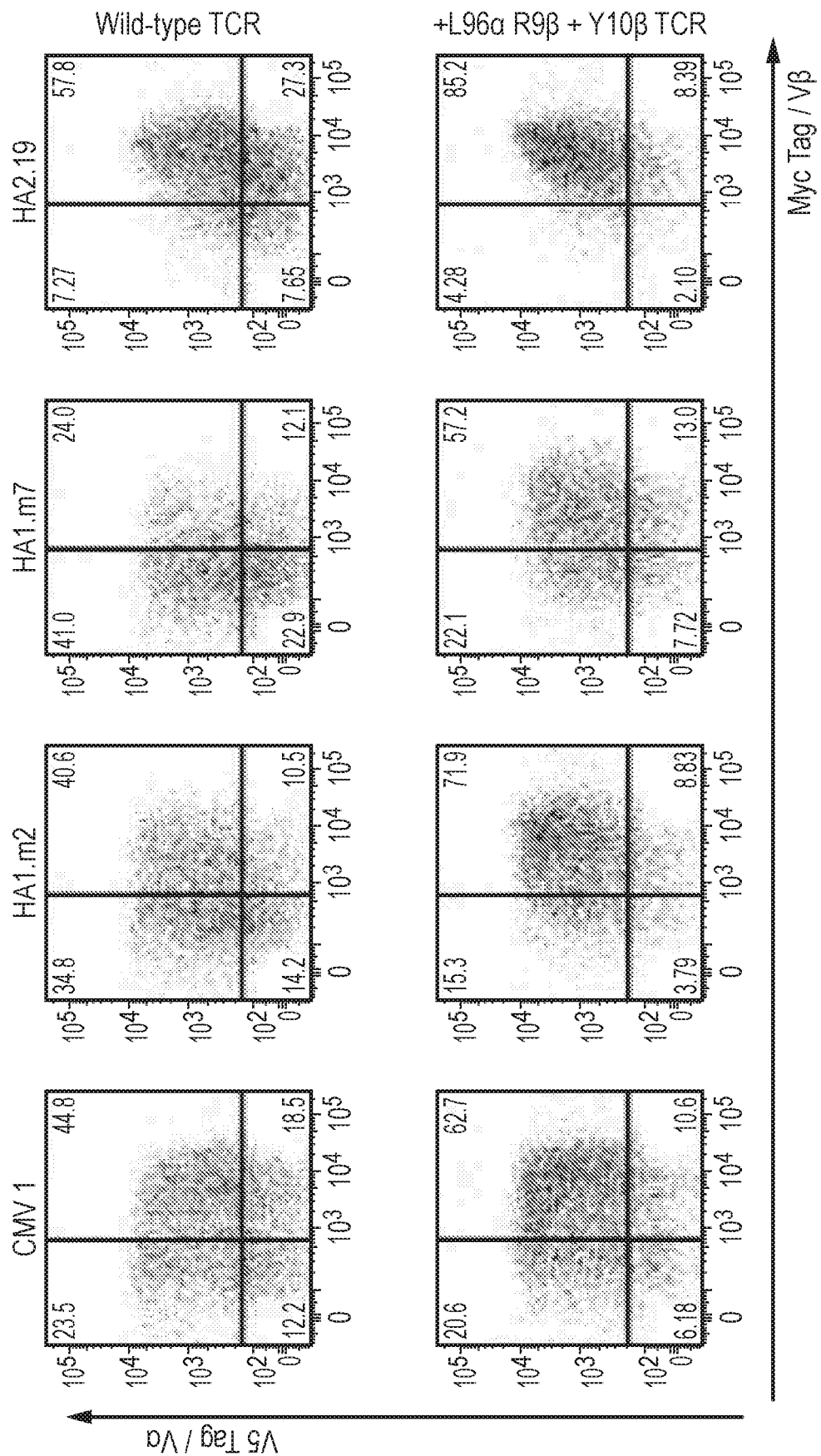

The modelling data above indicated that efficient interactions between the variable and constant domains in the α and β chain were particularly important for high-level expression. We therefore used 8 different TCRs to test whether improving the variable/constant interaction consistently enhanced expression of TCRs irrespective of V-region usage and specificity. The data showed that the combination of L96α, R9β and Y10β did indeed enhance the expression of all TCRs tested (FIG. 26a, b). Consistent with previous reports the wild type CMV2-TCR was an extreme case of a poorly expressed TCR that was undetectable on the cell surface, which was similar to the profile observed when the dominant TCR was converted into the poorly expressed d→weakTCR (FIG. 2d). The triple LRY modification of the CMV2-TCR resulted in surface expression, although at lower levels than the other TCRs. Comparison of all wild type and LRY-modified TCRs indicated that the replacement of three amino acids consistently increased surface expression in Jurkat cells by approximately 3 fold (FIG. 26 a,b), irrespective of the presence or absence of endogenous TCR. Next, we analysed in detail the expression and function of 4 antigen-specific TCRs (specific for CMV and minor histocompatibility antigens HA1 and HA2) in primary human T cells. The presence of the V5 and myc tags provided a powerful tool to distinguish the introduced TCR chains from the endogenous human TCR. More importantly, the V5/myc staining profile enabled us to identify double-positive T cells expressing both introduced TCR chains, and also single-positive T cells expressing only one of the introduced chains mis-paired with an endogenous TCR chain. Interestingly, there is a clear correlation between the level of TCR expression in Jurkat cells (FIG. 26a) and the frequency of primary human T cells expressing both TCR chains (FIG. 26c). For example, the unmodified HA1m7 TCR is poorly expressed in Jurkat cells and displays high levels of mis-pairing in primary T cells, as 41% of cells express only the introduced α chain, 12% only the β chain, and 24% both α and β chains. The analysis of all four TCRs showed that the LRY modification increased the frequency of primary T cells expressing both TCR chains from a range of 24-58% to 57-85%. For the LRY modified HA2.19 TCR, which is most strongly expressed in Jurkat cells, the majority of primary T cells expressed both introduced TCR chains on the cell surface.

Example 9—Demonstration of Cell Surface Expression with Further Amino Acid Residues Blosum62 classifications were used to determine conserved amino acids for a subset of the previously identified strong residues. A series of TCR constructs was generated using QuikChange mutagenesis, using the generic weak TCR described herein as the DNA template.

Figure 27:
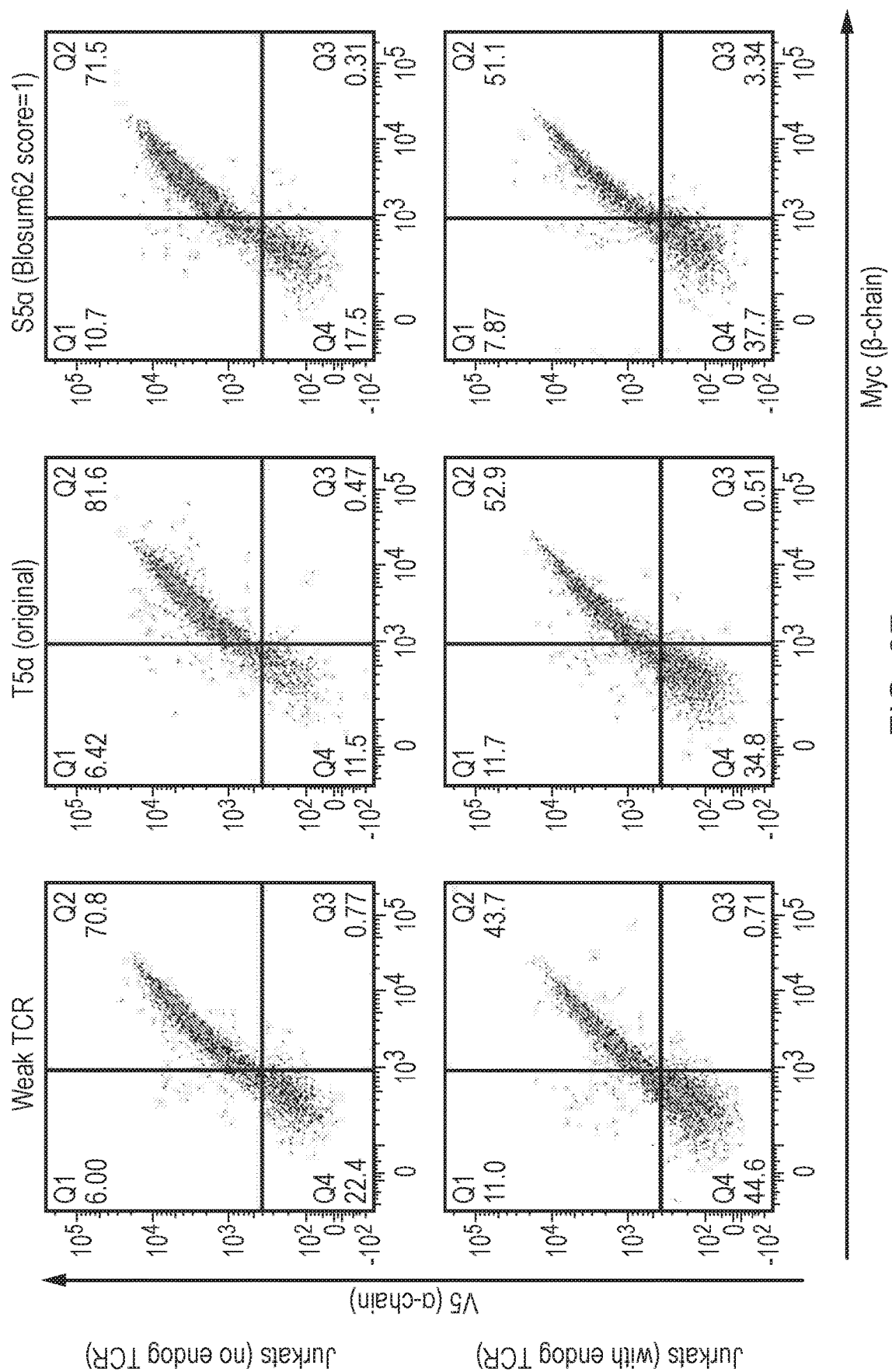
FIG. 27—Demonstration of cell surface expression with further amino acid residues. Blosum62 classifications were used to determine conserved amino acids for a subset of the previously identified strong residues. A series of TCR constructs was generated using QuikChange mutagenesis, using the generic weak TCR described herein as the DNA template. Constructs were transfected into Phoenix-Ampho cells and transduction into Jurkat cells that (i) do not or (ii) do have an endogenous TCR was performed. The expression of each TCR on Jurkat cells with/without endogenous TCR was performed, using the originally identified strong amino acid residues for comparison.
Figure 27:
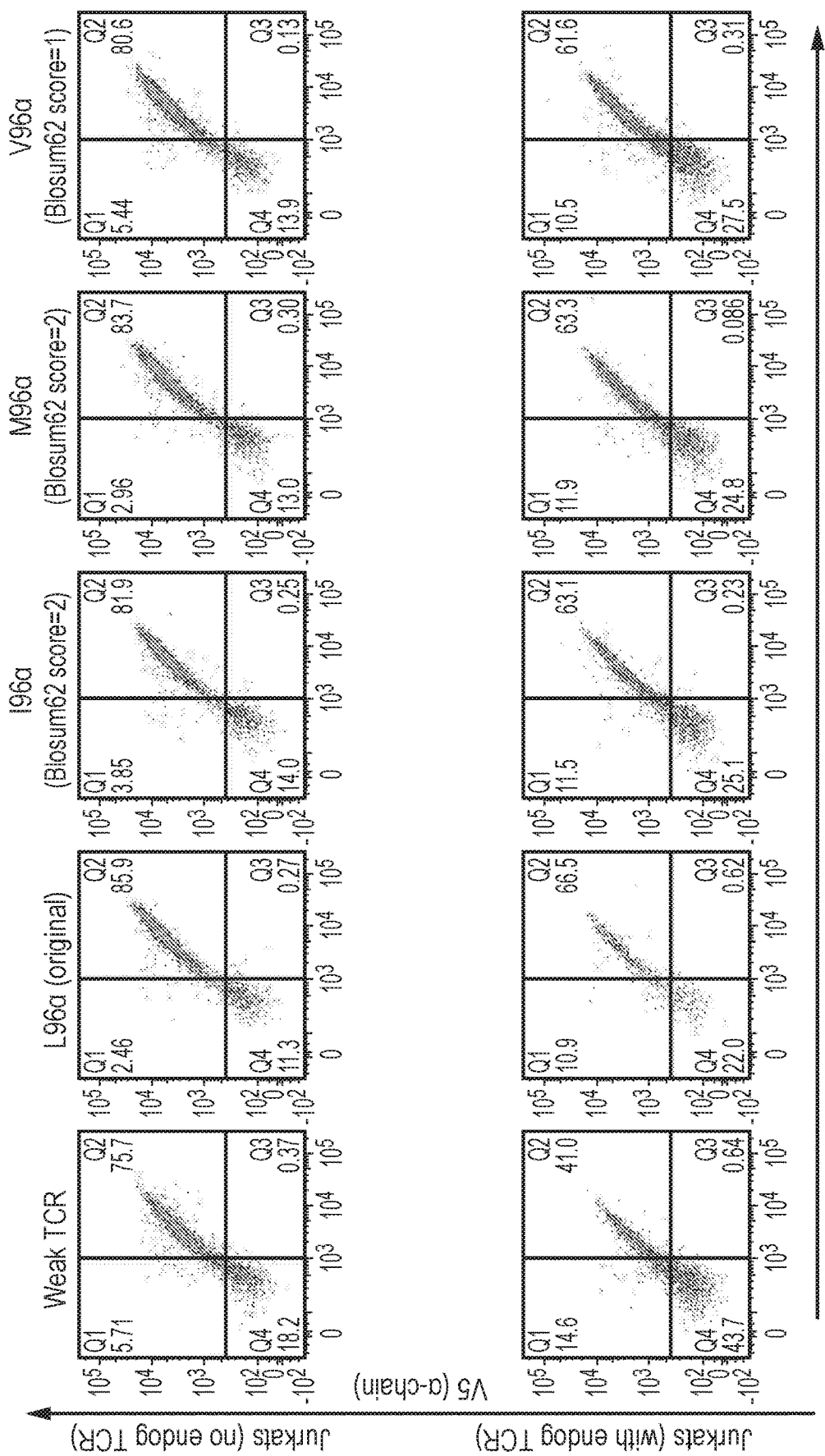
Figure 27:
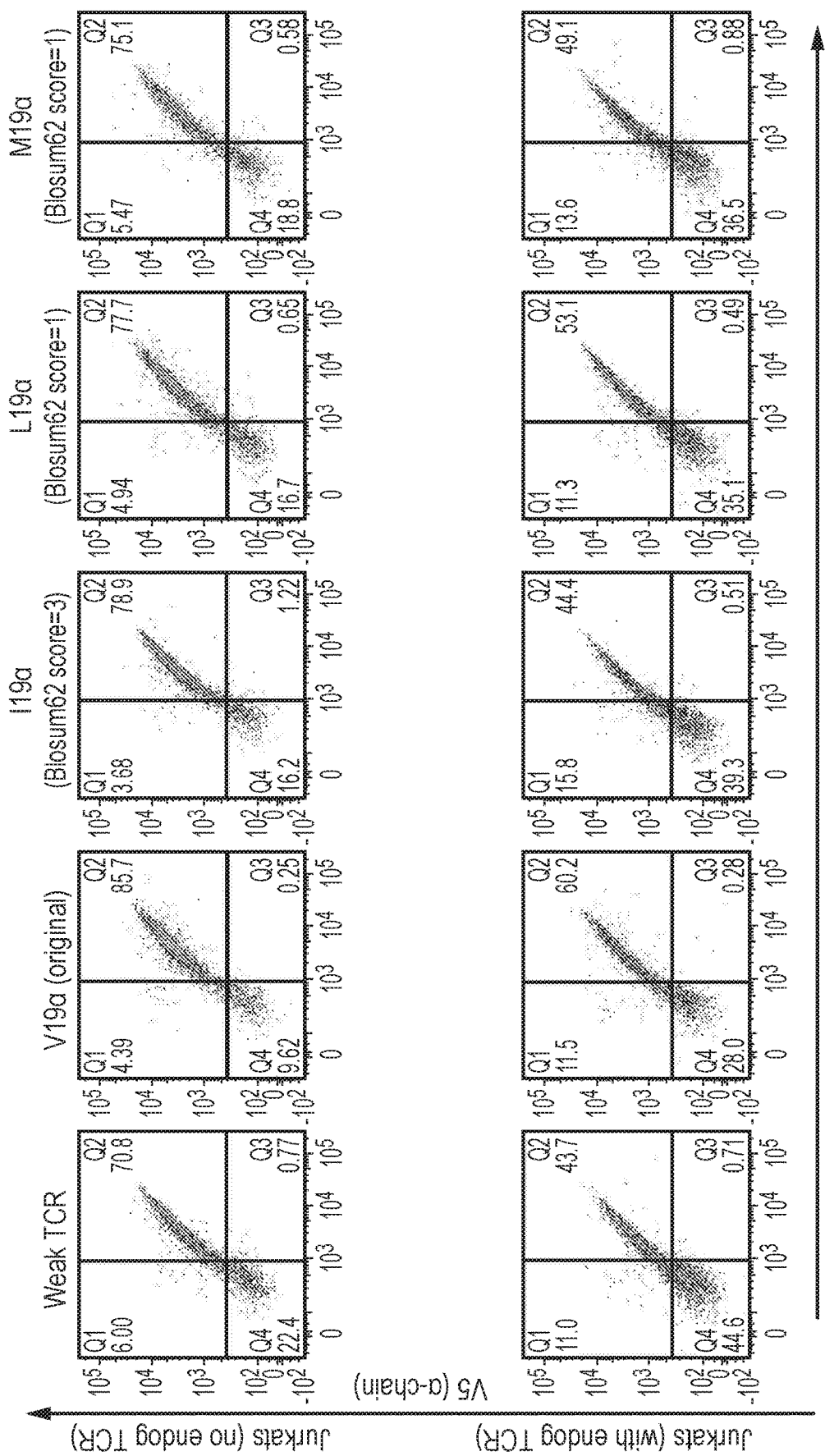
Figure 27:
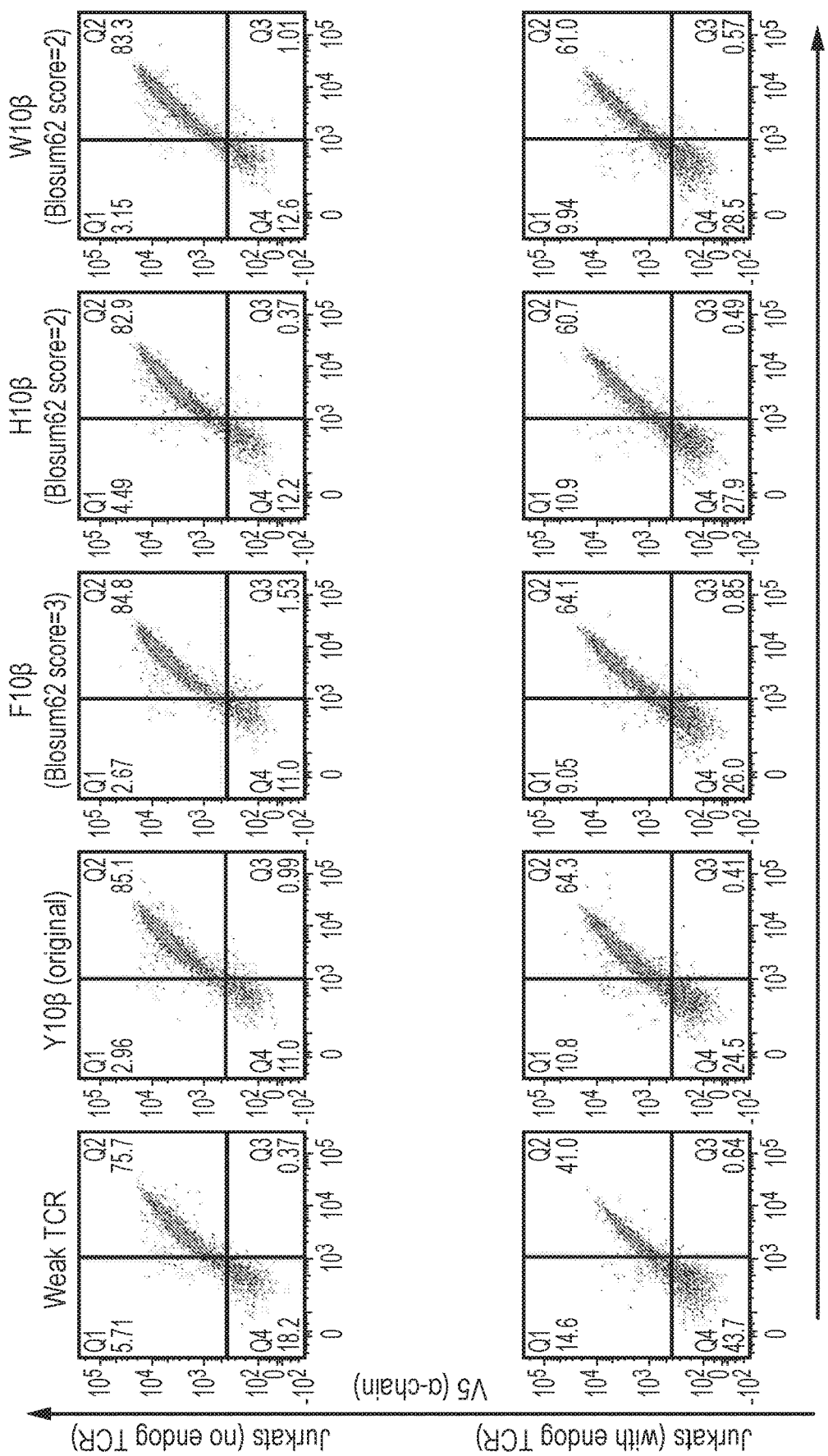

Constructs were transfected into Phoenix-Ampho cells and transduction into Jurkat cells that (i) do not or (ii) do have an endogenous TCR was performed. The expression of each TCR on Jurkat cells with/without endogenous TCR was performed, using the originally identified strong amino acid residues for comparison. The results shown in FIG. 27 demonstrate that at least conservative substitutions at position 5, 96 and 19 of the alpha chain and position 10 of the beta chain recapitulated the increased expression provided by the original dominant amino acid at the same position.

Figure 28:
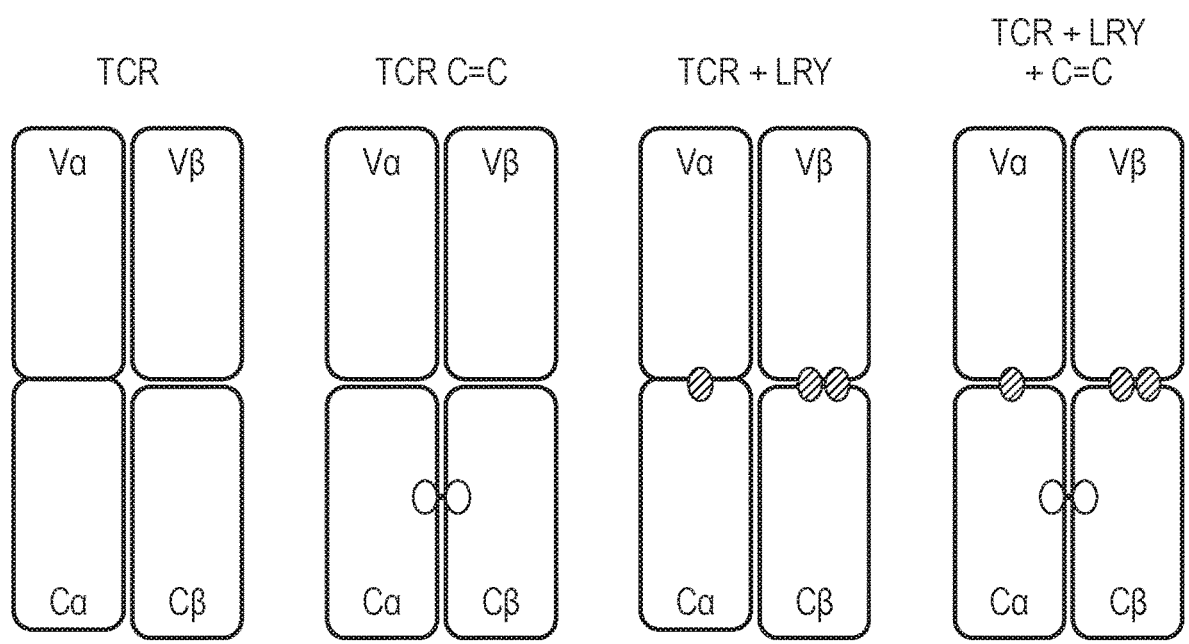
FIG. 28—Schematic of TCR constructs containing the C═C modification, the dominance (LRY) modification or both.
Figure 29:
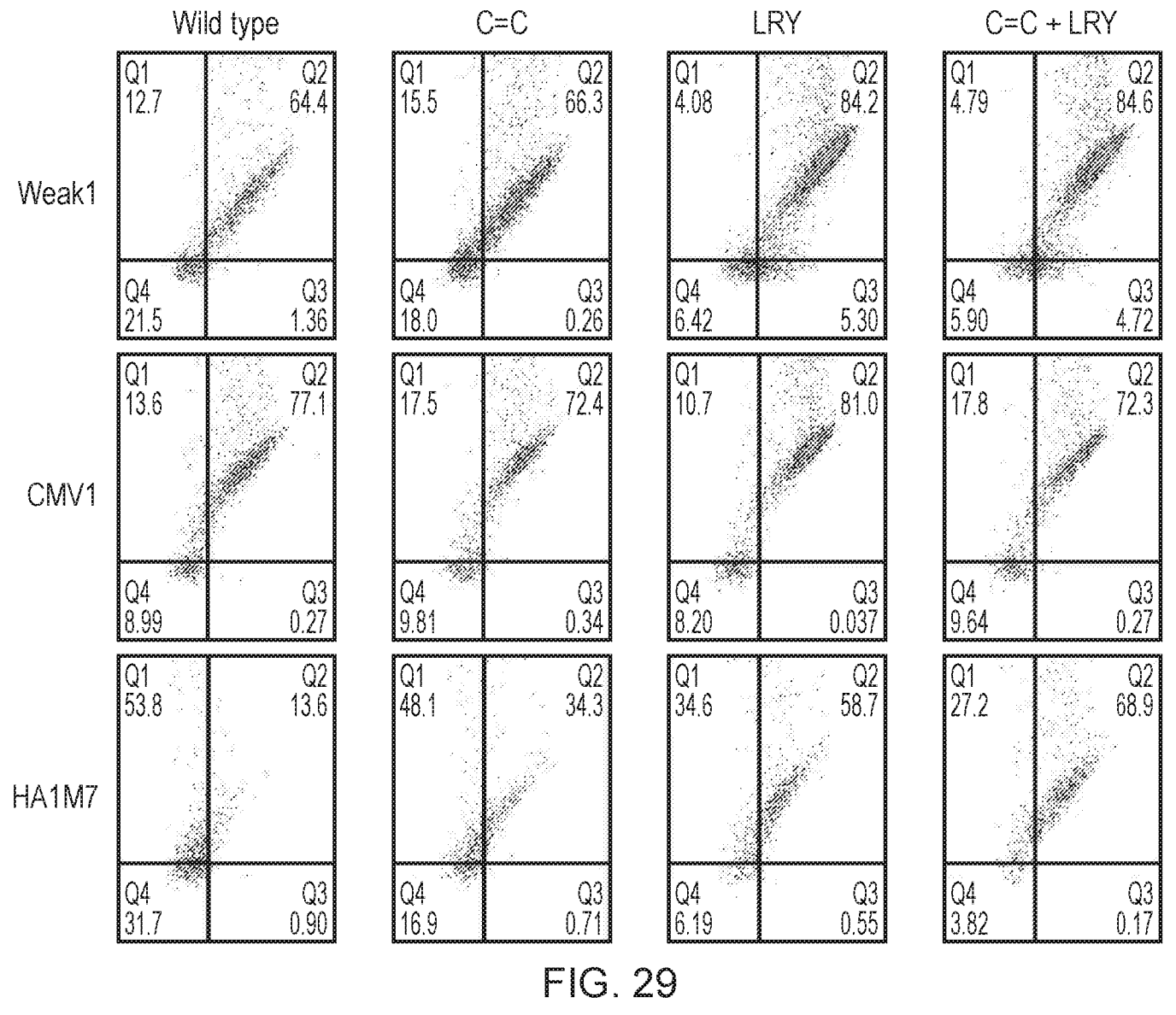
Figure 30:
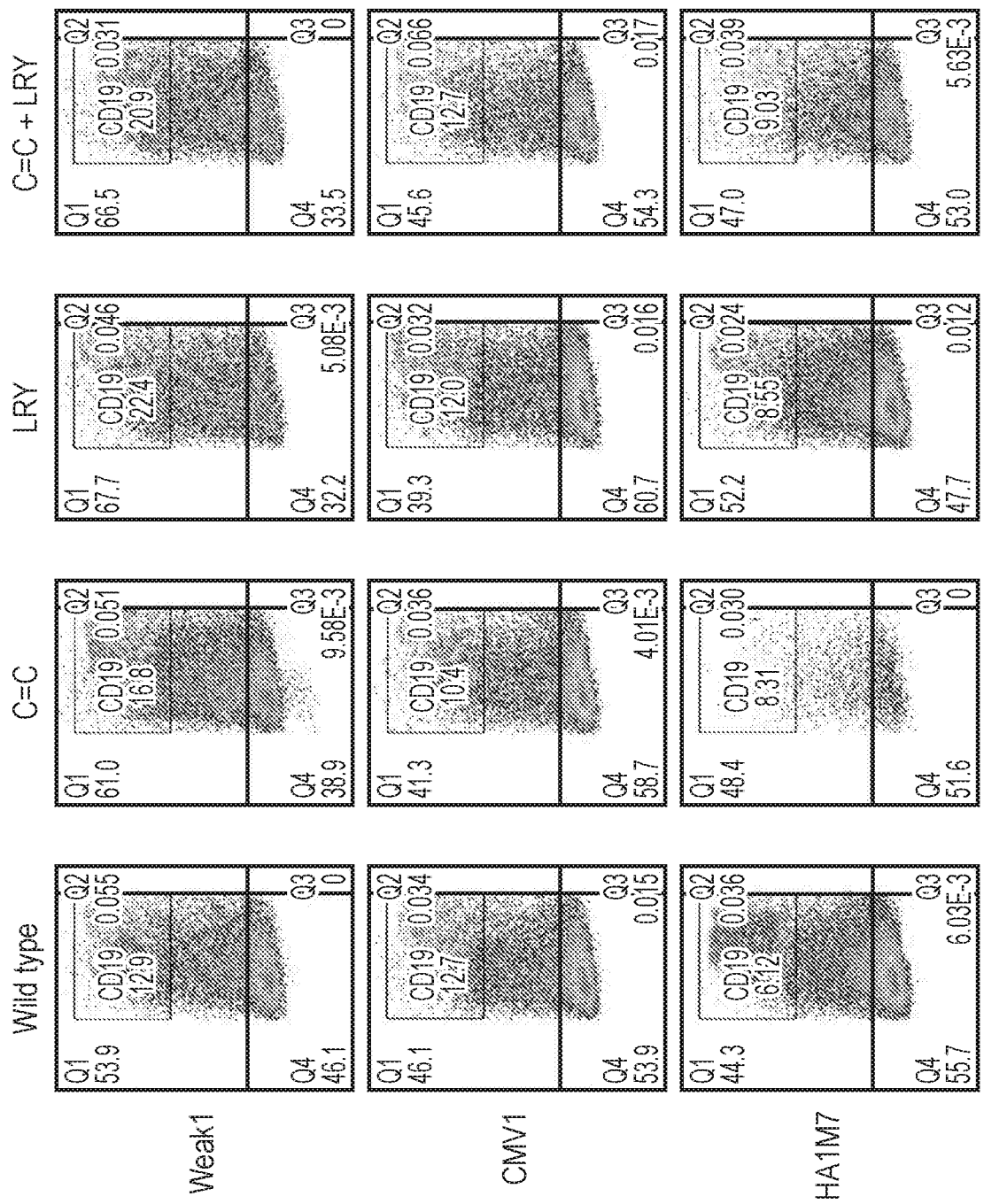
FIG. 30—Analysis of the three TCRs with appropriate modifications in human Jurkat cells that do express an endogenous TCR. Shown is the transduction efficacy as measured by percentage and MFI of CD19 expression. Gated CD19-high cells were analysed for levels of TCR expression.
Figure 31:
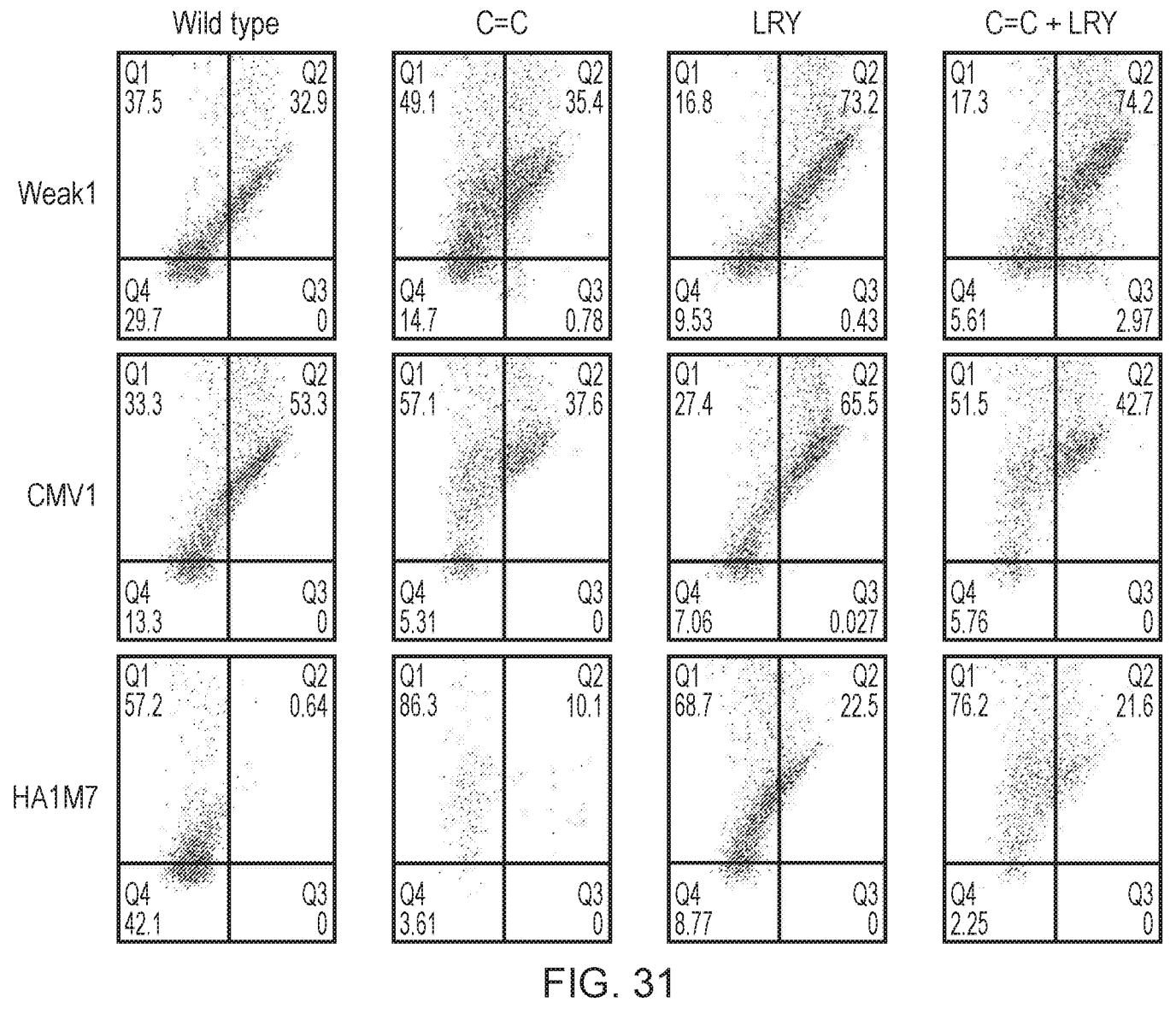

Example 10—Comparison of the Effects of C═C Modifications and the Present Modifications on the TCR Expression Levels Schematic of TCR constructs containing the C═C modification, the dominance (modified to include leucine at position 96 of the α chain; arginine at position 9 of the β chain; and tyrosine at position 10 of the β chain) modification or both are shown in FIG. 28. All of these modifications were tested in three TCRs: generic weak TCR, CMV-TCR and HA1m7-TCR in human Jurkat cells that do not express an endogenous TCR. Transduction efficacy as measured by percentage and MFI of CD19 expression and gated CD19-high cells were analysed for levels of TCR expression (FIG. 29-31).

The data indicate that the LRY modification is more efficient than the C═C modification in enhancing human TCR alpha/beta chain expression in Jurkat cells with or without endogenous TCR.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology, cellular immunology or related fields are intended to be within the scope of the following claims.

The invention claimed is:

1. A method which comprises the steps of:
(i) providing a TCR α chain and/or β chain sequence;
(ii) determining an amino acid residue of the TCR α chain and/or β chain at one or more positions selected from: 96 of the α chain; 9 of the β chain; 10 of the β chain; 24 of the α chain; 19 of the α chain; 20 of the α chain; 50 of the α chain; 5 of the α chain; 8 of the α chain; 86 of the α chain; 39 of the α chain; 55 of the α chain; 43 of the β chain; 66 of the α chain; 19 of the β chain; 21 of the β chain; 103 of the β chain; 3 of the α chain; 7 of the α chain; 9 of the α chain; 11 of the α chain; 16 of the α chain; 18 of the α chain; 21 of the α chain; 22 of the α chain; 26 of the α chain; 40 of the α chain; 47 of the α chain; 48 of the α chain; 49 of the α chain; 51 of the α chain; 52 of the α chain; 53 of the α chain; 67 of the α chain; 68 of the α chain; 74 of the α chain; 76 of the α chain; 79 of the α chain; 81 of the α chain; 83 of the α chain; 90 of the α chain; 92 of the α chain; 93 of the α chain; and 101 of the α chain; and
(iii) altering the amino acid residue at one or more of the positions listed in step (ii) to an amino acid residue selected from:
an aliphatic, non-polar amino acid or a methionine at position 96 of the α chain;
an aliphatic, polar charged amino acid or a glutamine at position 9 of the β chain;
an aromatic amino acid at position 10 of the β chain;
an aliphatic, polar uncharged amino acid at position 24 of the α chain;
an aliphatic, non-polar amino acid or a methionine at position 19 of the α chain;
an aliphatic, polar uncharged amino acid at position 20 of the α chain;
an aliphatic, polar uncharged amino acid or a isoleucine, leucine or valine at position 50 of the α chain;
an aliphatic, polar uncharged amino acid at position 5 of the α chain;
an aliphatic, polar uncharged amino acid, a glutamic acid, lysine or arginine at position 8 of the α chain;
an aliphatic, polar uncharged amino acid or alanine at position 86 of the α chain;
an aromatic amino acid at position 39 of the α chain;
an aliphatic, polar charged amino acid or asparagine at position 55 of the α chain;
an aliphatic, polar charged amino acid or a glutamine at position 43 of the β chain;
an aliphatic, non-polar amino acid or a serine at position 66 of the α chain;
an aliphatic, non-polar amino acid or a methionine at position 19 of the β chain;
an aliphatic, non-polar amino acid or a methionine at position 21 of the β chain;
an aliphatic, non-polar amino acid or a methionine at position 103 of the β chain;
an aliphatic, polar uncharged amino acid at position 3 of the α chain;
an aliphatic, polar uncharged amino acid or alanine at position 7 of the α chain;
an aliphatic, non-polar amino acid at position 9 of the α chain;
an aliphatic, non-polar amino acid or a isoleucine, leucine or valine at position 11 of the α chain;
an aliphatic, non-polar amino acid or a serine at position 16 of the α chain;
an aliphatic, polar uncharged amino acid at position 18 of the α chain;
an aliphatic, non-polar amino acid or a methionine at position 21 of the α chain;
an aliphatic, polar uncharged amino acid or alanine at position 22 of the α chain;
an aliphatic, polar charged amino acid or asparagine at position 26 of the α chain;
an aromatic amino acid at position 40 of the α chain;
an aliphatic, polar uncharged amino acid or alanine at position 47 of the α chain;
an aliphatic, polar charged amino acid or a glutamine at position 48 of the α chain;
an aliphatic, polar uncharged amino acid, glutamic acid, lysine or arginine at position 49 of the α chain;
an aliphatic, non-polar amino acid or a methionine at position 51 of the α chain;
an aliphatic, non-polar amino acid or a methionine at position 52 of the α chain;
an aliphatic, non-polar amino acid or a methionine at position 53 of the α chain;
an aliphatic, polar uncharged amino acid at position 67 of the α chain;
an aliphatic, polar charged amino acid or a glutamine at position 68 of the α chain;
an aliphatic, polar uncharged amino acid or an aspartic acid or histidine at position 74 of the α chain;
an aromatic amino acid at position 76 of the α chain;
an aliphatic, polar uncharged amino acid or an aspartic acid or histidine at position 79 of the α chain;
an aliphatic, polar uncharged amino acid, glutamic acid, lysine or arginine at position 81 of the α chain;
an aliphatic, non-polar amino acid or a serine at position 83 of the α chain;
an aliphatic, polar charged amino acid or a glutamine at position 90 of the α chain;
an aliphatic, polar uncharged amino acid or alanine at position 92 of the α chain;
an aliphatic, polar charged amino acid or asparagine at position 93 of the α chain; and an aliphatic, non-polar amino acid or a isoleucine, leucine or valine at position 101 of the α chain;
with the proviso that when only one amino acid is altered in step (iii) the altered amino acid generated does not consist of an amino acid residue specified for the given position selected from group (I):
(I) L96 of the α chain; R9 of the β chain; Y10 of the β chain; T24 of the α chain; V19 of the α chain; T20 of the α chain; M50 of the α chain; T5 of the α chain; Q8 of the α chain; S86 of the α chain; F39 of the α chain; D55 of the α chain; R43 of the β chain; A66 of the α chain; V19 of the β chain; L21 of the β chain; L103 of the β chain; T3 of the α chain; S7 of the α chain; P9 of the α chain; M11 of the α chain; A16 of the α chain; T18 of the α chain; L21 of the α chain; S22 of the α chain; D26 of the α chain; F40 of the α chain; S47 of the α chain; R48 of the α chain; Q49 of the α chain; I51 of the α chain; L52 of the α chain; V53 of the α chain; T67 of the α chain; E68 of the α chain; N74 of the α chain; F76 of the α chain; N79 of the α chain; Q81 of the α chain; A83 of the α chain; K90 of the α chain; S92 of the α chain; D93 of the α chain; and M101 of the α chain; and
when two or more amino acid residues are altered in step (iii) at least one of the altered amino acid residues generated is not an amino acid residue specified for the given position selected from group (I).

2. A method according to claim 1 wherein the one or more altered amino acid residues generated in step (iii) are selected from:
an aliphatic, non-polar amino acid at position 96 of the α chain;
an aliphatic, polar charged amino acid at position 9 of the β chain;
an aromatic amino acid at position 10 of the β chain;
an aliphatic, polar uncharged amino acid at position 24 of the α chain;
an aliphatic, non-polar amino acid at position 19 of the α chain;
an aliphatic, polar uncharged amino acid at position 20 of the α chain;
an aliphatic, polar uncharged amino acid at position 50 of the α chain;
an aliphatic, polar uncharged amino acid at position 5 of the α chain;
an aliphatic, polar uncharged amino acid at position 8 of the α chain;
an aliphatic, polar uncharged amino acid at position 86 of the α chain;
an aromatic amino acid at position 39 of the α chain;
an aliphatic, polar charged amino acid at position 55 of the α chain;
an aliphatic, polar charged amino acid at position 43 of the β chain;
an aliphatic, non-polar amino acid at position 66 of the α chain;
an aliphatic, non-polar amino acid at position 19 of the β chain;
an aliphatic, non-polar amino acid at position 21 of the β chain;
an aliphatic, non-polar amino acid at position 103 of the β chain;
an aliphatic, polar uncharged amino acid at position 3 of the α chain;
an aliphatic, polar uncharged amino acid at position 7 of the α chain;
an aliphatic, non-polar amino acid at position 9 of the α chain;
an aliphatic, polar uncharged amino acid at position 11 of the α chain;
an aliphatic, non-polar amino acid at position 16 of the α chain;
an aliphatic, polar uncharged amino acid at position 18 of the α chain;
an aliphatic, non-polar amino acid at position 21 of the α chain;
an aliphatic, polar uncharged amino acid at position 22 of the α chain;
an aliphatic, polar charged amino acid at position 26 of the α chain;
an aromatic amino acid at position 40 of the α chain;
an aliphatic, polar uncharged amino acid at position 47 of the α chain;
an aliphatic, polar charged amino acid at position 48 of the α chain;
an aliphatic, polar uncharged amino acid at position 49 of the α chain;
an aliphatic, non-polar amino acid at position 51 of the α chain;
an aliphatic, non-polar amino acid at position 52 of the α chain;
an aliphatic, non-polar amino acid at position 53 of the α chain;
an aliphatic, polar uncharged amino acid of the α chain;
an aliphatic, polar charged amino acid at position 68 of the α chain;
an aliphatic, polar uncharged amino acid at position 74 of the α chain;
an aromatic amino acid at position 76 of the α chain;
an aliphatic, polar uncharged amino acid at position 79 of the α chain;
an aliphatic, polar uncharged amino acid at position 81 of the α chain;
an aliphatic, non-polar amino acid at position 83 of the α chain;
an aliphatic, polar charged amino acid at position 90 of the α chain;
an aliphatic, polar uncharged amino acid at position 92 of the α chain;
an aliphatic, polar charged amino acid at position 93 of the α chain; and an aliphatic, polar uncharged amino acid at position 101 of the α chain.

3. A method according to claim 1 wherein the one or more altered amino acid residues generated in step (iii) are selected from:
leucine, isoleucine, valine or methionine at position 96 of the α chain;
arginine, lysine or glutamine at position 9 of the β chain;
tyrosine, phenylalanine, histidine or tryptophan at position 10 of the β chain;
threonine or serine at position 24 of the α chain;
valine, isoleucine, leucine or methionine at position 19 of the α chain;
threonine or serine at position 20 of the α chain;
methionine, isoleucine, leucine or valine at position 50 of the α chain;
threonine or serine at position 5 of the α chain;
glutamine, glutamic acid, lysine or arginine at position 8 of the α chain;
serine, alanine, asparagine or threonine at position 86 of the α chain;
phenylalanine, tyrosine, histidine or tryptophan at position 39 of the α chain;
aspartic acid, glutamic acid or asparagine at position 55 of the α chain;
arginine, lysine or glutamine at position 43 of the β chain;
alanine or serine at position 66 of the α chain;
valine, isoleucine, leucine or methionine at position 19 of the β chain;
leucine, isoleucine, valine or methionine at position 21 of the β chain;
leucine, isoleucine, valine or methionine at position 103 of the β chain;
threonine or serine at position 3 of the α chain;
serine, alanine, asparagine or threonine at position 7 of the α chain;
methionine, isoleucine, leucine or valine at position 11 of the α chain;
alanine or serine at position 16 of the α chain;
threonine or serine at position 18 of the α chain;
leucine, isoleucine, methionine or valine at position 21 of the α chain;
serine, alanine, asparagine or threonine at position 22 of the α chain;
aspartic acid, glutamic acid or asparagine at position 26 of the α chain;
phenylalanine, tyrosine or tryptophan at position 40 of the α chain;

serine, alanine, asparagine or threonine at position 47 of the α chain;
arginine, lysine or glutamine at position 48 of the α chain;
glutamine, glutamic acid, lysine or arginine at position 49 of the α chain;
isoleucine, leucine, valine or methionine at position 51 of the α chain;
leucine, isoleucine, methionine or valine at position 52 of the α chain;
valine, isoleucine, leucine, methionine at position 53 of the α chain;
threonine, serine at position 67 of the α chain;
glutamic acid, aspartic acid, glutamine or lysine at position 68 of the α chain;
asparagine, aspartic acid, histidine or serine at position 74 of the α chain;
phenylalanine, tyrosine or tryptophan at position 76 of the α chain;
asparagine, aspartic acid, histidine or serine at position 79 of the α chain;
glutamine, glutamic acid, lysine or arginine at position 81 of the α chain;
alanine or serine at position 83 of the α chain;
lysine, arginine, glutamic acid or glutamine at position 90 of the α chain;
serine, alanine, asparagine or threonine at position 92 of the α chain;
aspartic acid, glutamic acid or asparagine at position 93 of the α chain; and
methionine, isoleucine, leucine or valine at position 101 of the α chain.

4. A method according to claim 1 wherein the one or more altered amino acid residues generated in step (iii) are selected from one or more of:
an aliphatic, non-polar amino acid or a methionine at position 96 of the α chain;
an aliphatic, polar charged amino acid or a glutamine at position 9 of the β chain;
an aromatic amino acid at position 10 of the β chain;
an aliphatic, polar uncharged amino acid at position 24 of the α chain;
an aliphatic, non-polar amino acid or a methionine at position 19 of the α chain;
an aliphatic, polar uncharged amino acid at position 20 of the α chain;
an aliphatic, polar uncharged amino acid or a isoleucine, leucine or valine at position 50 of the α chain;
an aliphatic, polar uncharged amino acid at position 5 of the α chain;
an aliphatic, polar uncharged amino acid, a glutamic acid, lysine or arginine at position 8 of the α chain;
an aliphatic, polar uncharged amino acid or alanine at position 86 of the α chain;
an aromatic amino acid at position 39 of the α chain;
an aliphatic, polar charged amino acid or asparagine at position 55 of the α chain; and an aliphatic, polar charged amino acid or a glutamine at position 43 of the β chain.

5. A method according to claim 2 wherein the one or more altered amino acid residues generated in step (iii) are selected from one or more of:
an aliphatic, non-polar amino acid at position 96 of the α chain;
an aliphatic, polar charged amino acid at position 9 of the β chain;
an aromatic amino acid at position 10 of the β chain;
an aliphatic, polar uncharged amino acid at position 24 of the α chain;
an aliphatic, non-polar amino acid at position 19 of the α chain;
an aliphatic, polar uncharged amino acid at position 20 of the α chain;
an aliphatic, polar uncharged amino acid at position 50 of the α chain;
an aliphatic, polar uncharged amino acid at position 5 of the α chain;
an aliphatic, polar uncharged amino acid at position 8 of the α chain;
an aliphatic, polar uncharged amino acid at position 86 of the α chain;
an aromatic amino acid at position 39 of the α chain;
an aliphatic, polar charged amino acid at position 55 of the α chain; and an aliphatic, polar charged amino acid at position 43 of the β chain.

6. A method according to claim 3 wherein the one or more altered amino acid residues generated in step (iii) are selected from one or more of:
leucine, isoleucine, valine or methionine at position 96 of the α chain;
arginine, lysine or glutamine at position 9 of the β chain;
tyrosine, phenylalanine, histidine or tryptophan at position 10 of the β chain;
threonine or serine at position 24 of the α chain;
valine, isoleucine, leucine or methionine at position 19 of the α chain;
threonine or serine at position 20 of the α chain;
methionine, isoleucine, leucine or valine at position 50 of the α chain;
threonine or serine at position 5 of the α chain;
glutamine, glutamic acid, lysine or arginine at position 8 of the α chain;
serine, alanine, asparagine or threonine at position 86 of the α chain;
phenylalanine, tyrosine, histidine or tryptophan at position 39 of the α chain;
aspartic acid, glutamic acid or asparagine at position 55 of the α chain; and arginine, lysine or glutamine at position 43 of the β chain.

7. A method according to claim 1 wherein the one or more altered amino acid residues generated in step (iii) comprises:
(a) an aliphatic, non-polar amino acid or a methionine at position 96 of the α chain; or
(b) isoleucine, valine or methionine at position 96 of the α chain.

8. A method according to claim 1 wherein the one or more altered amino acid residue produced in step (iii) comprises:
(a) an aliphatic, polar charged amino acid or a glutamine at position 9 of the β chain; or
(b) lysine or glutamine at position 9 of the β chain.

9. A method according to claim 1 wherein the one or more altered amino acid residue produced in step (iii) comprises:
(a) an aromatic amino acid at position 10 of the β chain; or
(b) phenylalanine, histidine or tryptophan at position 10 of the β chain.

10. A method according to claim 1, wherein the one or more altered amino acid residue produced in step (iii) comprises:
(a) an aliphatic, polar uncharged amino acid at position 24 of the α chain; or
(b) serine at position 24 of the α chain.

11. A method according to claim 1, wherein the one or more altered amino acid residues produced in step (iii) comprises isoleucine, valine or methionine at position 96 of the α chain; lysine or glutamine at position 9 of the β chain; and phenylalanine, histidine or tryptophan at position 10 of the β chain.

\* \* \* \* \*